US008324186B2

(12) United States Patent
Zhang et al.

(10) Patent No.: US 8,324,186 B2
(45) Date of Patent: *Dec. 4, 2012

(54) 4-AZETIDINYL-1-HETEROATOM LINKED-CYCLOHEXANE ANTAGONISTS OF CCR2

(75) Inventors: Xuqing Zhang, Audubon, PA (US); Heather Rae Hufnagel, Glenmoore, PA (US); Zhihua Sui, Spring House, PA (US)

(73) Assignee: Janssen Pharmaceutica N.V., Beerse (BE)

( * ) Notice: Subject to any disclaimer, the term of this patent is extended or adjusted under 35 U.S.C. 154(b) by 41 days.

This patent is subject to a terminal disclaimer.

(21) Appl. No.: 12/760,855

(22) Filed: Apr. 15, 2010

(65) Prior Publication Data

US 2010/0267668 A1    Oct. 21, 2010

Related U.S. Application Data

(60) Provisional application No. 61/170,225, filed on Apr. 17, 2009.

(51) Int. Cl.
*A61K 31/695* (2006.01)
*A61K 31/4025* (2006.01)
*C07D 413/02* (2006.01)
*C07D 239/20* (2006.01)
*C07D 401/02* (2006.01)
*C07D 231/10* (2006.01)

(52) U.S. Cl. ............... 514/63; 514/210.19; 514/210.2; 544/238; 544/316; 544/319; 546/268.1; 548/110; 548/240; 548/364.1

(58) Field of Classification Search ........... 514/63, 514/210.19, 210.2; 544/238, 316, 319; 546/268.1; 548/110, 240, 364.1
See application file for complete search history.

(56) References Cited

U.S. PATENT DOCUMENTS

| 6,245,799 | B1 | 6/2001 | Asselin et al. |
| 6,255,315 | B1 | 7/2001 | Patane et al. |
| 2003/0004151 | A1 | 1/2003 | Cherney et al. |
| 2006/0069123 | A1 | 3/2006 | Xia et al. |
| 2006/0135502 | A1 | 6/2006 | Cherney et al. |
| 2006/0252751 | A1 | 11/2006 | Xue et al. |
| 2010/0144695 | A1 | 6/2010 | Zhang et al. |
| 2010/0267688 | A1 | 10/2010 | Zhang et al. |
| 2010/0267689 | A1 | 10/2010 | Zhang et al. |

FOREIGN PATENT DOCUMENTS

| EP | 1201239 | 5/2002 |
| WO | WO 9857641 | 12/1998 |
| WO | WO 0134598 | 5/2001 |
| WO | WO 2004/050024 | 6/2004 |
| WO | WO 2006/073592 | * 7/2006 ............. 514/210.2 |
| WO | WO 2007003965 | 1/2007 |
| WO | WO 2007/053498 | 5/2007 |
| WO | WO 2007/130712 | 11/2007 |
| WO | WO 2010/068663 | 6/2010 |
| WO | WO 2010/121011 | 10/2010 |
| WO | WO 2010/121036 | 10/2010 |
| WO | WO 2010/121046 | 10/2010 |

OTHER PUBLICATIONS

Morissette et al. Advanced Drug Delivery Reviews 2004, 56, 275-300.*
Vippagunta et al., abstract, Vippagunta, Sudha R. "Crystalline Solids." Advanced Drug Delivery Reviews 48(2001): 3-26.*
Thornber, C.W. Isosterism and Molecular Modification in Drug Design. Royal Society of Chemistry. 1979, pp. 563-580.*
Golub et al. Science (1999), vol. 286 531-537.*
Lala et al. Cancer and Metastasis Reviews (1998), 17(1), 91-106.*
Dawson, et al, "Targeting Monocyte Chemoattractant Protein-1 Signalling in Disease", Expert Opin. Ther. Targets, 2003, vol. 7(1), pp. 35-48.
Seebach, et al, "Safe One-Pot Carbon-Carbon Bond Formation with Lithiated Nitrosamines Including Denitrosation by Sequential Reduction with Lithium a Aluminium Hydride and Raney-Nickel", Synthesis, 1979, vol. 6, pp. 423-424.
Gdaniec, et al., "Conformation and Stereodynamics of N,N-Dinitroso-2,4,6,8-tetraaryl-3,7-diazabicyclo [3.3.1] nonanes", J. Org. Chem., 1997 vol. 62, pp. 5619-5622.
Abdel-Magid, et al., "Reductive Amination of Aldehydes and Ketones with Sodium Triacetoxyborohydride. Studies on Direct and Indirect Reductive Amination Procedures", J. Org. Chem, 1996, vol. 61, pp. 3849-3862.
Chan, et al., "1,5-Bis (Trimethylsiloxy)-1,5-Dimethoxy-1-4-Pentadienes. Cyclopropance Synthesis Via Intramolecular Coupling", Tetrahedron Letters, 1982 vol. 23, No. 8, pp. 799-802.
Rollins, "Monocyte chemoattractant protein 1: a potential regulator of monocyte recruitment in inflammatory disease", 89Mol. Med. Today, 1996 vol. 2, pp. 198.
Das, B. et al. "A Highly Chemoselective Boc Protection of Amines using Sulfonic-Acid-Functionalized Silica As an Efficient Heterogeneous Recyclable Catalyst", Tetrahedron Lett. 2006, 47, 7551-7556.
Ingersoll, A. W. et. al., "Hippuric Acid", Organic Syntheses 1932, *XII*, vol. 12. pp. 40.

(Continued)

*Primary Examiner* — Joseph K. McKane
*Assistant Examiner* — Samantha Shterengarts
(74) *Attorney, Agent, or Firm* — Mary A. Appollina

(57) ABSTRACT

The present invention comprises compounds of Formula (I).

Formula (I)

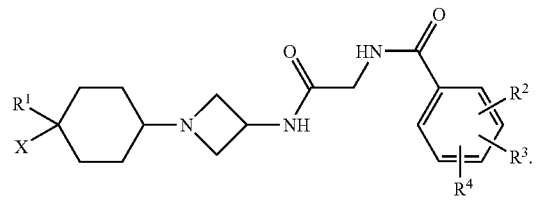

wherein: X, $R^1$, $R^2$, $R^3$, and $R^4$ are as defined in the specification. The invention also comprises a method of preventing, treating or ameliorating a syndrome, disorder or disease, wherein said syndrome, disorder or disease is type II diabetes, obesity and asthma. The invention also comprises a method of inhibiting CCR2 activity in a mammal by administration of a therapeutically effective amount of at least one compound of Formula (I).

16 Claims, No Drawings

OTHER PUBLICATIONS

Xia M, Sui Z, "Recent Developments in CCR2 Antagonists", *Expert Opin. Ther. Patents*, 2009, 19(3), 295-303.
Bundgaard, et al., "Design of Prodrugs: Bioreversible Derivatives for Various Functional Groups and Chemical Entities", Elsevier Science Publishers, 1985, pp. 1-4, Chapter 1.
Bryn, et al., "Hydrates and Solvates", Solid State Chemistry of Drugs, $2^{nd}$ Edition, 1999, pp. 232-247, Chapter 10, Polymorphs.
Han, et al., "Targeted Prodrug Design to Optimize Drug Delivery", AAPS PHARMSCI, 2000, vol. 2 (1) pp. 1-11.
International Search Report, PCT/US2010/031255, Oct. 18, 2011.
International Search Report, PCT/US2009/067307, Aug. 2, 2010.
International Search Report, PCT/US2010/031265, Oct. 18, 2011.
International Search Report, PCT/US2010/031212, Oct. 18, 2011.
International Search Report, PCT/US2011/039724, Jul. 19, 2011.
International Search Report, PCT/US2011/040610, Aug. 29, 2011.
U.S. Appl. No. 12/760,832, filed Apr. 15, 2010.
U.S. Appl. No. 12/633,861, filed Dec. 9, 2009.
U.S. Appl. No. 12/761,080, filed Apr. 15, 2010.
U.S. Appl. No. 13/161,572, filed Jun. 16, 2011.
U.S. Appl. No. 13/156,450, filed Jun. 9, 2011.
PCT/US2009/067307 International Search Report, Aug. 2, 2010.
Havlioglu, et al., " Slit Proteins potential endogenous modulators of inflammation" Neurovirology, vol. 8, pp. 486-495, 2002.
Banker, et al., Modern Pharmaceutics, Third edition revised and Expanded, pp. 451 and 596, 1996.
Wolff, et al., some consideration for prodrug design, Burger's Medicinal Chemistry and Drug Discovery $5^{th}$ edition, vol. 1: Principles and Practice pp. 975-977, 1995.
Damasio, et al. Alzheimer's Disease and related dementias, Cecil textbook of Medicine, $20^{th}$ edition, vol. 2 pp. 1992-1996.
Simone, Oncology: Introduction, Cecil textbook of Medicine, $20^{th}$ edition vol. 1 pp. 1004-1010, 1996.
Gura, et al., Systems for identifying new drugs are often faulty, Science, 278: pp. 1041-1042, 1997.
Johnson, et al., Relationships between drug activity in NCI preclinical in vitro and in vivo models and early clinical trials, British Journal of Cancer, 84 (10): 1424-1431, 2001.
Ulrich, et al., Chapter 4: Crystallization, Kirk-Othmer Encyclopedia of Chemical Technology, Aug. 2002.
West, Solid Solutions, Solid State chemistry and its applications, pp. 358-365, 1988.
Barnes, New Drugs for Asthma, 2004, Nature Reviews: Drug Discovery, vol. 3 pp. 831-844.
Horuk, Chemokine receptor antagonists: overcoming developmental hurdles, 2009, Nature Reviews: Drug discovery vol. 8 pp. 23-33.
Kang, CCR2 antagonism improves insulin resistance, lipid metabolism, and diabetic nephropathy in type 2 diabetic mice, 2010, Kidney Internation, vol. 78, pp. 883-894.
Palmqvist, Chemokines and their receptor as potential targets for the treatment of asthma, 2007, British Journal of Pharmacology, vol. 151, pp. 725-726.
Tamura, Inhibition of CCR2 Ameloiorates Insulin resistance and Hepatic Steatosis in db/db Mice, 2008, Arterioscler Thromb Vasc Biol. pp. 2195-2201.
Silva, Mini-rev. Med. Chem. 2005, vol. 5 pp. 893-914.

* cited by examiner

4-AZETIDINYL-1-HETEROATOM LINKED-CYCLOHEXANE ANTAGONISTS OF CCR2

CROSS-REFERENCE TO RELATED APPLICATIONS

This application claims priority from U.S. Provisional Application Ser. No. 61/170,225 filed Apr. 17, 2009, the contents of each of which are hereby incorporated by reference in their entirety.

FIELD OF THE INVENTION

The invention is directed to substituted dipiperidine compounds, which are antagonists to the chemoattractant cytokine receptor 2 (CCR2), pharmaceutical compositions, and methods for use thereof. More particularly, the CCR2 antagonists are substituted piperidyl acrylamide compounds useful for preventing, treating or ameliorating a CCR2 mediated syndrome, disorder or disease.

BACKGROUND OF THE INVENTION

CCR2 is a member of the GPCR family of receptors, as are all known chemokine receptors, and are expressed by monocytes and memory T-lymphocytes. The CCR2 signaling cascade involves activation of phospholipases (PLCβ2), protein kinases (PKC), and lipid kinases (PI-3 kinase).

Chemoattractant cytokines (i.e., chemokines) are relatively small proteins (8-10 kD), which stimulate the migration of cells. The chemokine family is divided into four subfamilies based on the number of amino acid residues between the first and second highly conserved cysteines.

Monocyte chemotactic protein-1 (MCP-1) is a member of the CC chemokine subfamily (wherein CC represents the subfamily having adjacent first and second cysteines) and binds to the cell-surface chemokine receptor 2 (CCR2). MCP-1 is a potent chemotactic factor, which, after binding to CCR2, mediates monocyte and lymphocyte migration (i.e., chemotaxis) toward a site of inflammation. MCP-1 is also expressed by cardiac muscle cells, blood vessel endothelial cells, fibroblasts, chondrocytes, smooth muscle cells, mesangial cells, alveolar cells, T-lymphocytes, marcophages, and the like. After monocytes enter the inflammatory tissue and differentiate into macrophages, monocyte differentiation provides a secondary source of several proinflammatory modulators, including tumor necrosis factor-α (TNF-α), interleukin-1 (IL-1), IL-8 (a member of the CXC chemokine subfamily, wherein CXC represents one amino acid residue between the first and second cysteines), IL-12, arachidonic acid metabolites (e.g., $PGE_2$ and $LTB_4$), oxygen-derived free radicals, matrix metalloproteinases, and complement components.

Animal model studies of chronic inflammatory diseases have demonstrated that inhibition of binding between MCP-1 and CCR2 by an antagonist suppresses the inflammatory response. The interaction between MCP-1 and CCR2 has been implicated (see Rollins B J, Monocyte chemoattractant protein 1: a potential regulator of monocyte recruitment in inflammatory disease, *Mol. Med. Today*, 1996, 2:198; and Dawson J, et al., Targeting monocyte chemoattractant protein-1 signaling in disease, *Expert Opin. Ther. Targets*, 2003 Feb. 7 (1):35-48) in inflammatory disease pathologies such as psoriasis, uveitis, atherosclerosis, rheumatoid arthritis (RA), multiple sclerosis, Crohn's Disease, nephritis, organ allograft rejection, fibroid lung, renal insufficiency, type II diabetes and diabetic complications, diabetic nephropathy, diabetic retinopathy, diabetic retinitis, diabetic microangiopathy, tuberculosis, sarcoidosis, invasive staphylococcia, inflammation after cataract surgery, allergic rhinitis, allergic conjunctivitis, chronic urticaria, Chronic Obstructive Pulmonary Disease (COPD), allergic asthma, periodontal diseases, periodonitis, gingivitis, gum disease, diastolic cardiomyopathies, cardiac infarction, myocarditis, chronic heart failure, angiostenosis, restenosis, reperfusion disorders, glomerulonephritis, solid tumors and cancers, chronic lymphocytic leukemia, chronic myelocytic leukemia, multiple myeloma, malignant myeloma, Hodgkin's disease, and carcinomas of the bladder, breast, cervix, colon, lung, prostate, and stomach. Monocyte migration is inhibited by MCP-1 antagonists (either antibodies or soluble, inactive fragments of MCP-1), which have been shown to inhibit the development of arthritis, asthma, and uveitis. Both MCP-1 and CCR2 knockout (KO) mice have demonstrated that monocyte infiltration into inflammatory lesions is significantly decreased. In addition, such KO mice are resistant to the development of experimental allergic encephalomyelitis (EAE, a model of human MS), cockroach allergen-induced asthma, atherosclerosis, and uveitis. Rheumatoid arthritis and Crohn's Disease patients have improved during treatment with TNF-α antagonists (e.g., monoclonal antibodies and soluble receptors) at dose levels correlated with decreases in MCP-1 expression and the number of infiltrating macrophages.

MCP-1 has been implicated in the pathogenesis of seasonal and chronic allergic rhinitis, having been found in the nasal mucosa of most patients with dust mite allergies. MCP-1 has also been found to induce histamine release from basophils in vitro. During allergic conditions, both allergens and histamines have been shown to trigger (i.e., to up-regulate) the expression of MCP-1 and other chemokines in the nasal mucosa of people with allergic rhinitis, suggesting the presence of a positive feedback loop in such patients. There remains a need for small molecule CCR2 antagonists for preventing, treating or ameliorating a CCR2 mediated inflammatory syndrome, disorder or disease resulting from MCP-1 induced monocyte and lymphocyte migration to a site of inflammation. All documents cited herein are incorporated by reference.

SUMMARY OF THE INVENTION

The present invention comprises compounds of Formula (I).

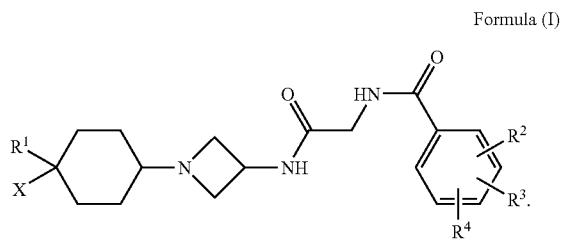

Formula (I)

wherein:

X is H, F, OH, or $NH_2$;

$R^1$ is

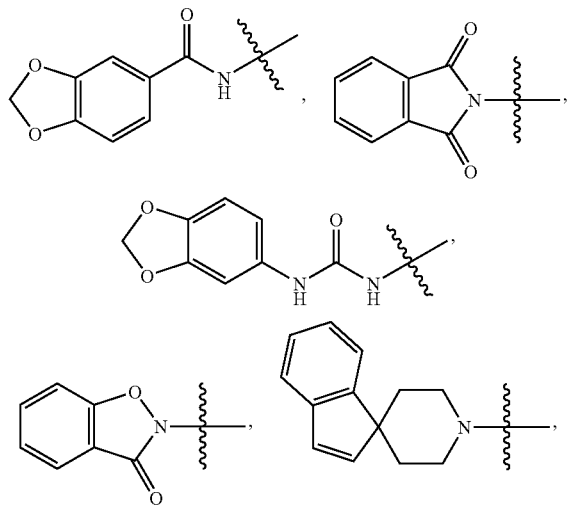

—O-benzoisothiazol-3-yl, —O-benzoisoxazolyl, —O-benzothiazolyl, —O-benzoxazolyl, —O-benzofuryl, —O-indolyl, —O-benzoimidazolyl, —O-indazolyl, —O-furyl, —O-imidazolyl, —O-oxazolyl, —O-isoxazolyl, —O-thiophenyl, —O-benzothiophenyl, —O-thiazolyl, —O-isothiazolyl, —O-pyridazyl, —O-pyrazolyl, —O-pyrrolyl, —O-benzo[1,3]dioxolyl, —O-pyrimidyl, indazol-1-yl, —O-pyridyl, imidazol-1-yl, pyridon-1-yl, pyrimidon-1-yl, pyrazol-1-yl, indol-1-yl, pyridaz-1-yl, or pyrrol-1-yl; alternatively, both $R^1$ and X can be taken together with their attached carbon to form a ring selected from the group consisting of:

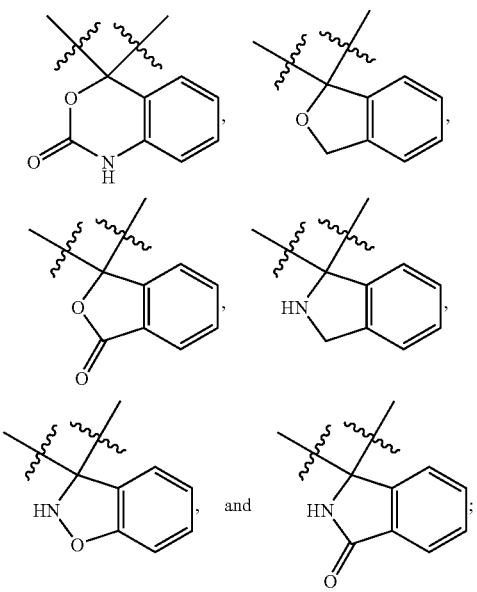

and wherein any $R^1$ group may be substituted with up to two methyl groups, or one substituent selected from the group consisting of: $OC_{(1-4)}$alkyl, $OC_{(3-6)}$cycloalkyl, $OCH_2CF_3$, $OCH_2Ph$, F, I, CN, Cl, $OCF_3$, $CF_3$, $CH_2CN$, $C_{(1-4)}$alkyl, $CH_2CF_3$, $N(C_{1-4})$alkyl)$_2$, $C_{(1-4)}$alkylOH, $Si(CH_3)_3$,

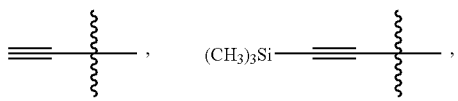

$SCH_3$, $S(O)CH_3$, $SO_2CH_3$, pyrrolidinyl, OH, $NH_2$, NHCN, $CO_2H$, $CONH_2$, $NHCO_2C_{(1-4)}$alkyl, $N(SO_2CH_3)_2$, $NHSO_2CH_3$, $NHC(O)CF_3$, $NHC_{(1-4)}$alkyl, $NHCO_2H$, $NHCO_2C_{(1-4)}$alkyl, $NHCOC_{(1-4)}$alkyl, $NHCONH_2$, $NHCONHC_{(1-4)}$alkyl, and Br;

$R^2$ is $C_{(1-4)}$alkyl, $NH_2$, $NO_2$, $NHCH_2CH_2OH$, $N(C_{(1-4)}$alkyl)$_2$, $N(SO_2CH_3)_2$, CN, F, Cl, Br, $CF_3$, cycloalkyl, heterocyclyl, $OCF_3$, $OCF_2H$, $CF_2H$, or $OC_{(1-4)}$alkyl;

$R^3$ is H, F, Cl, $CF_3$, or $OC_{(1-4)}$alkyl; alternatively, $R^2$ and $R^3$ may be taken together with their attached phenyl to form a benzo[1,3]dioxolyl, 2,3-dihydro-benzofuranyl, or 2,3-dihydro-benzo[1,4]dioxinyl group;

$R^4$ is H, $OC_{(1-4)}$alkyl, or F;

and solvates, hydrates, tautomers, and pharmaceutically acceptable salts thereof.

DETAILED DESCRIPTION OF THE INVENTION

The present invention comprises compounds of Formula (I):

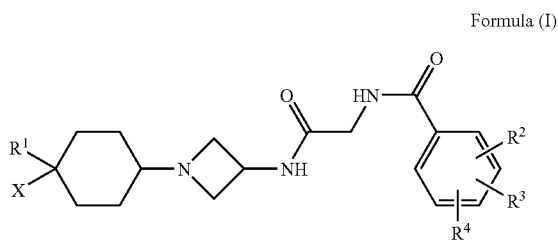

Formula (I)

Formula (I)
wherein X, $R^1$, $R^2$, $R^3$ and $R^4$ are as defined above;

and solvates, hydrates, tautomers, and pharmaceutically acceptable salts thereof.

Another embodiment of the invention comprises the compounds of Formula (Ia):

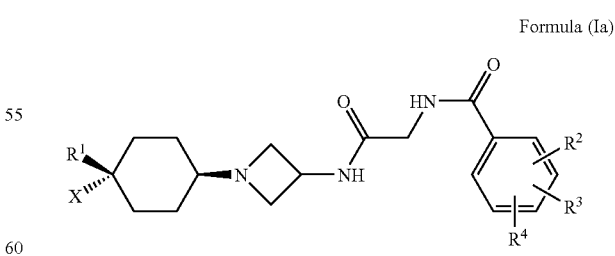

Formula (Ia)

wherein X, $R^1$, $R^2$, $R^3$ and $R^4$ are as defined above for Formula (I).

Another embodiment of the invention comprises compounds of Formula (I) and/or Formula (Ia) wherein:

X is H, F, or OH;

$R^1$ is

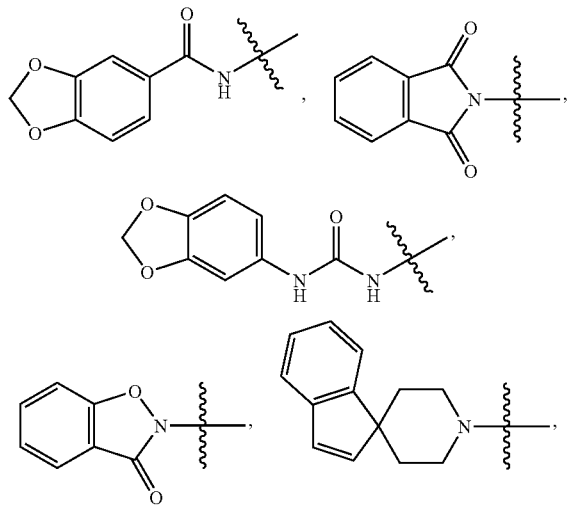

—O-benzoisothiazol-3-yl, —O-benzoisoxazolyl, —O-benzothiazolyl, —O-benzoxazolyl, —O-benzofuryl, —O-indolyl, —O-benzoimidazolyl, —O-indazolyl, —O-furyl, —O-imidazolyl, —O-oxazolyl, —O-isoxazolyl, —O-thiophenyl, —O-benzothiophenyl, —O-thiazolyl, —O-isothiazolyl, —O-pyridazyl, —O-pyrazolyl, —O-pyrrolyl, —O-benzo[1,3]dioxolyl, —O-pyrimidyl, indazol-1-yl, —O-pyridyl, imidazol-1-yl, pyridon-1-yl, pyrimidon-1-yl, pyrazol-1-yl, indol-1-yl, pyridaz-1-yl, or pyrrol-1-yl; wherein said —O-pyridyl is optionally substituted with Br, F, Cl, OH, CN, $OCF_3$, $CF_3$, $OC_{(1-4)}$alkyl, or $C_{(1-4)}$alkyl; wherein said imidazol-1-yl is optionally substituted with up to two $CH_3$ groups; wherein said pyridon-1-yl or said —O-pyrimidyl is optionally substituted with Cl, OH, CN, $OCF_3$, $CF_3$, $C_{(1-4)}$alkyl, F, I or $OC_{(1-4)}$alkyl; wherein said pyrimidon-1-yl is optionally substituted with Br, F, Cl, OH, CN, $OCF_3$, $CF_3$, $OC_{(1-4)}$alkyl, or $C_{(1-4)}$alkyl; and wherein said pyrazol-1-yl is optionally substituted with F, I,

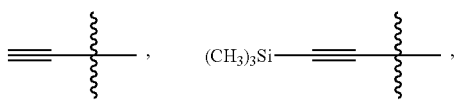

or $C_{(1-4)}$alkyl;

alternatively, both $R^1$ and X can be taken together with their attached carbon to form a ring selected from the group consisting of:

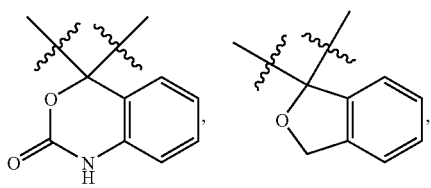

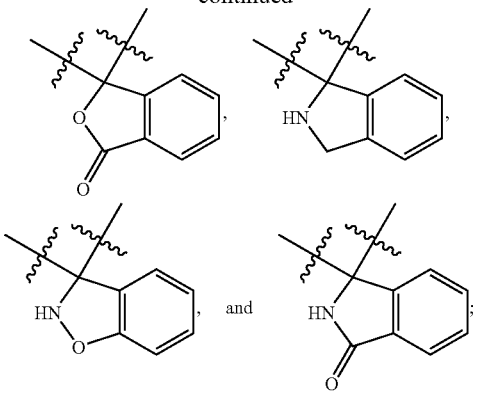

$R^2$ is $C_{(1-4)}$alkyl, $NH_2$, $NO_2$, $NHCH_2CH_2OH$, $N(C_{(1-4)}$alkyl$)_2$, $N(SO_2CH_3)_2$, CN, F, Cl, Br, $CF_3$, pyrrolidinyl, $OCF_3$, $OCF_2H$, $CF_2H$, or $OC_{(1-4)}$alkyl;

$R^3$ is H, F, Cl, $CF_3$, or $OC_{(1-4)}$alkyl; alternatively, $R^2$ and $R^3$ may be taken together with their attached phenyl to form a benzo[1,3]dioxolyl group;

$R^4$ is H, $OCH_3$, or F;

and solvates, hydrates, tautomers, and pharmaceutically acceptable salts thereof.

Another embodiment of the invention comprises compounds of Formula (I) and/or Formula (Ia) wherein:

X is H, or F;

$R^1$ is

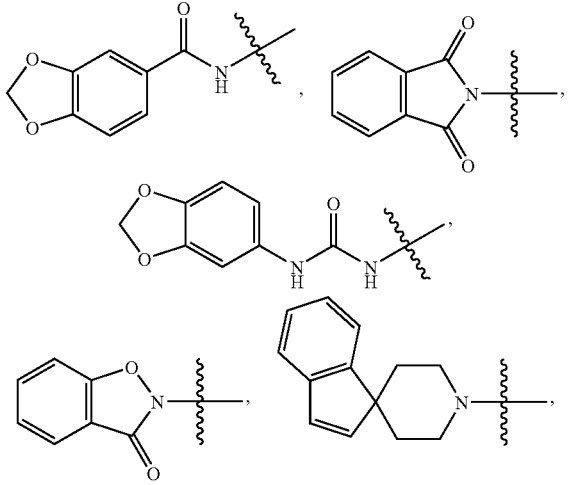

—O-benzoisothiazol-3-yl, —O-benzoisoxazolyl, —O-benzo[1,3]dioxolyl, —O-pyrimidyl, indazol-1-yl, —O-pyridyl, imidazol-1-yl, pyridon-1-yl, pyrimidon-1-yl, or pyrazol-1-yl, wherein said —O-pyridyl is optionally substituted with Br, F, Cl, OH, CN, $OCF_3$, $CF_3$, $OC_{(1-4)}$alkyl, or $C_{(1-4)}$alkyl; wherein said imidazol-1-yl is optionally substituted with up to two $CH_3$ groups; wherein said pyridon-1-yl is optionally substituted with Cl, OH, CN, $OCF_3$, $CF_3$, $C_{(1-4)}$alkyl, F, or $OC_{(1-4)}$alkyl; wherein said pyrimidon-1-yl or said —O-pyrimidyl is optionally substituted with Br, F, Cl, OH, CN, $OCF_3$, $CF_3$, $OC_{(1-4)}$alkyl, or $C_{(1-4)}$alkyl; and wherein said pyrazol-1-yl is optionally substituted with F,

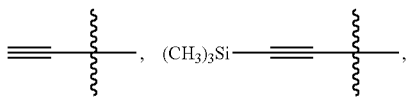

or C$_{1-4}$)alkyl;

alternatively, both R$^1$ and X can be taken together with their attached carbon to form a ring selected from the group consisting of:

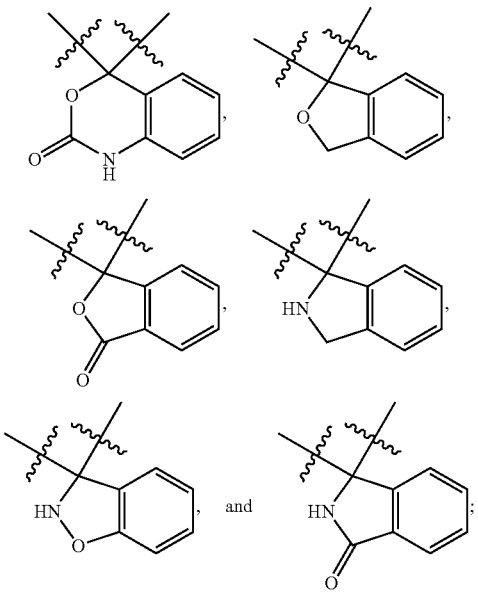

R$^2$ is NH$_2$, NO$_2$, NHCH$_2$CH$_2$OH, N(CH$_3$)$_2$, N(SO$_2$CH$_3$)$_2$, CN, F, Cl, Br, CF$_3$, pyridinyl, pyrrolidinyl, or OCH$_3$;

R$^3$ is H, F, Cl, CF$_3$, or OCH$_3$; alternatively, R$^2$ and R$^3$ may be taken together with their attached phenyl to form a benzo[1,3]dioxolyl group;

R$^4$ is H, or F;

and solvates, hydrates, tautomers, and pharmaceutically acceptable salts thereof.

Another embodiment of the invention comprises compounds of Formula (I) and/or Formula (Ia) wherein:

X is H;

R$^1$ is

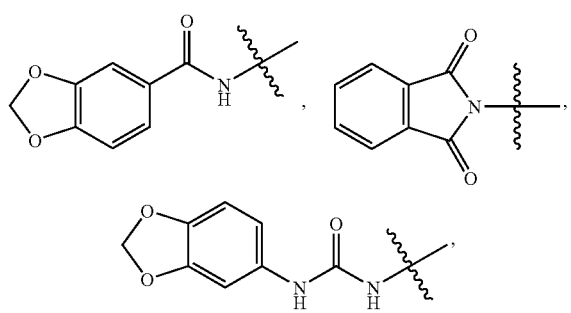

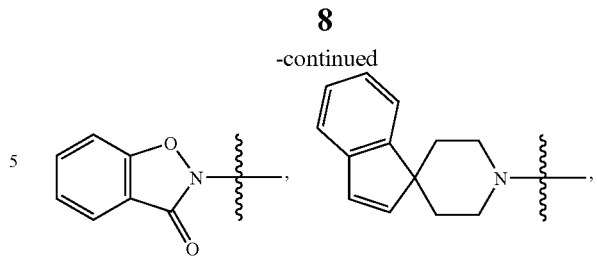

—O-benzoisothiazol-3-yl, —O-benzoisoxazolyl, —O-benzo[1,3]dioxolyl, —O-pyrimidyl, indazol-1-yl, —O-pyridyl, imidazol-1-yl, pyridon-1-yl, pyrimidon-1-yl, or pyrazol-1-yl, wherein said —O-pyridyl is optionally substituted with OC$_{(1-4)}$alkyl, or C$_{(1-4)}$alkyl; wherein said imidazol-1-yl is optionally substituted with up to two CH$_3$ groups; wherein said pyridon-1-yl is optionally substituted with Cl, OH, CN, CF$_3$, C$_{(1-4)}$alkyl, F, or OC$_{(1-4)}$alkyl; wherein said pyrimidon-1-yl or said —O-pyrimidyl is optionally substituted with Br; and wherein said pyrazol-1-yl is optionally substituted with F,

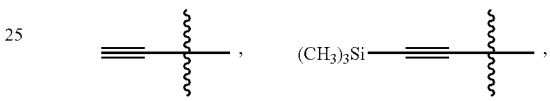

or C$_{(1-4)}$alkyl; alternatively, both R$^1$ and X can be taken together with their attached carbon to form a ring selected from the group consisting of:

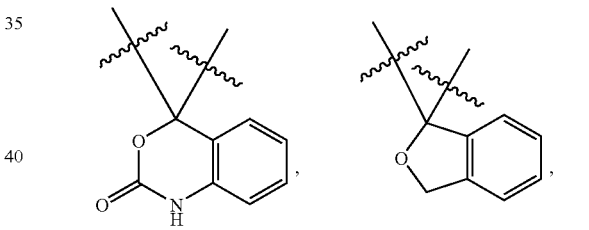

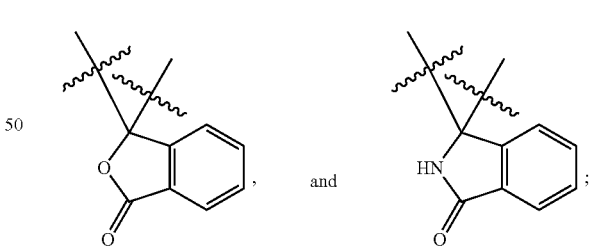

R$^2$ is F, Br, CF$_3$, NO$_2$, NH$_2$, NHCH$_2$CH$_2$OH, N(CH$_3$)$_2$, N(SO$_2$CH$_3$)$_2$, pyrolidinyl, pyridinyl, OCH$_3$;

R$^3$ is H;

R$^4$ is H;

and solvates, hydrates, tautomers, and pharmaceutically acceptable salts thereof.

Another embodiment of the invention comprises compounds of Formula (I) and/or Formula (Ia) wherein:

X is H;

R¹ is

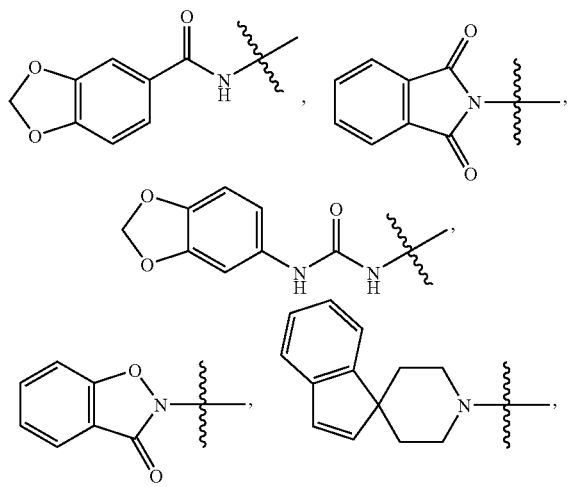

—O-benzoisothiazol-3-yl, —O-benzoisoxazolyl, —O-benzo[1,3]dioxolyl, —O-pyrimidyl, indazol-1-yl, —O-pyridyl, imidazol-1-yl, pyridon-1-yl, pyrimidon-1-yl, or pyrazol-1-yl, wherein said —O-pyridyl is optionally substituted with OCH₃, or CH₃; wherein said imidazol-1-yl is optionally substituted with up to two CH₃ groups; wherein said pyridon-1-yl is optionally substituted with Cl, OH, CN, CF₃, CH₃, F, or OCH₃; wherein said pyrimidon-1-yl or said —O-pyrimidyl is optionally substituted with Br; and wherein said pyrazol-1-yl is optionally substituted with F,

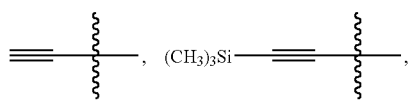

or CH₃;

alternatively, both R¹ and X can be taken together with their attached carbon to form a ring selected from the group consisting of:

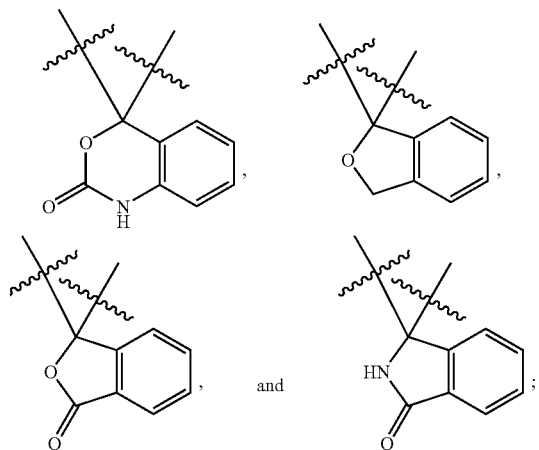

R² is CF₃;
R³ is H;
R⁴ is H;

and solvates, hydrates, tautomers, and pharmaceutically acceptable salts thereof.

Another embodiment of the invention is a compound which is selected from the group consisting of:

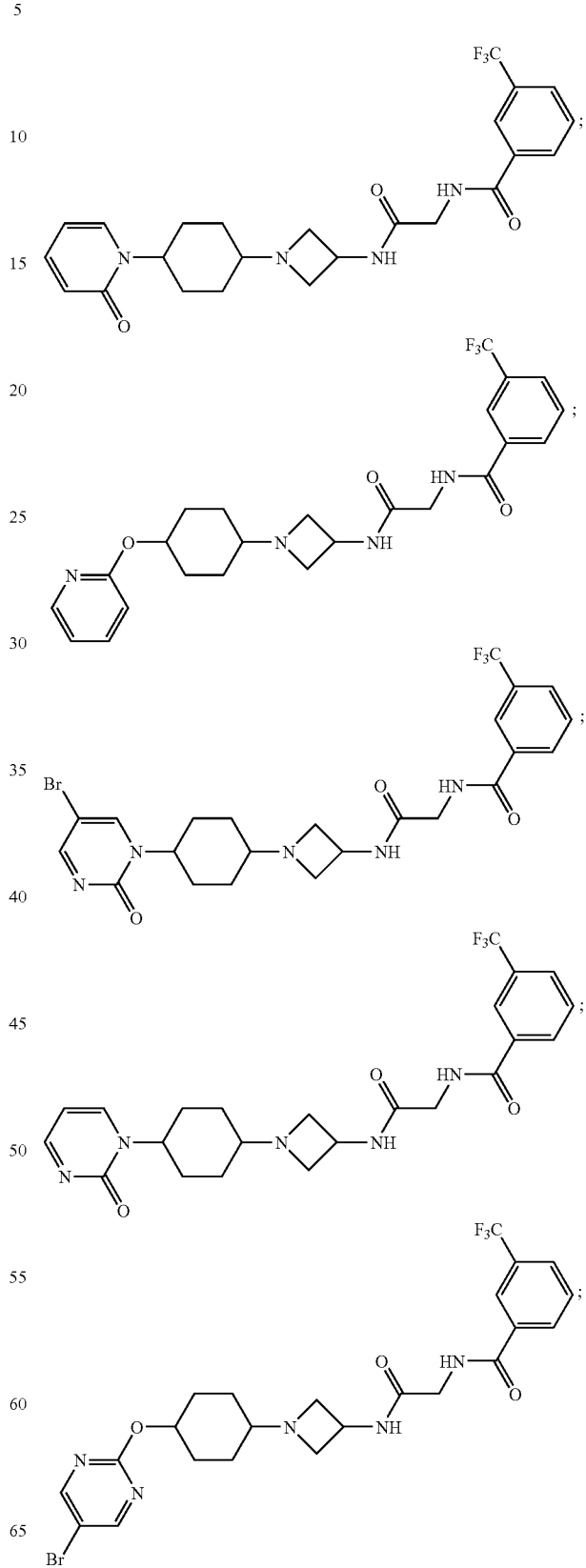

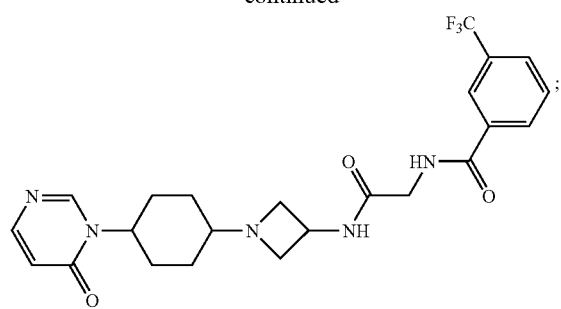
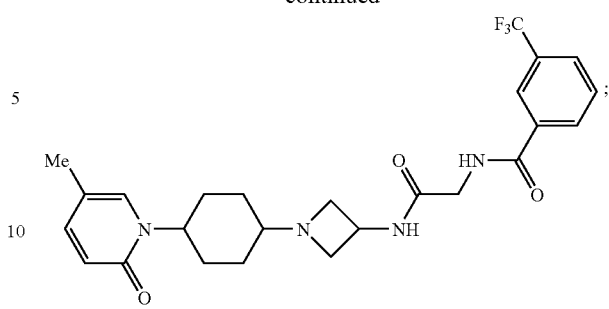
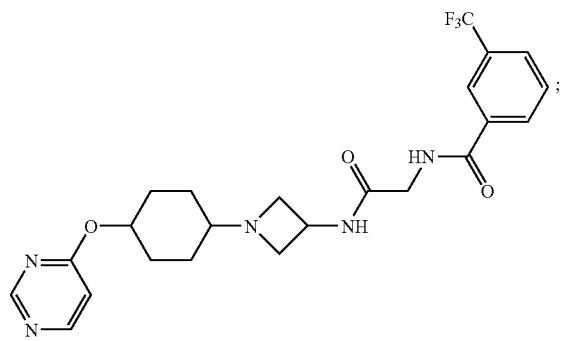
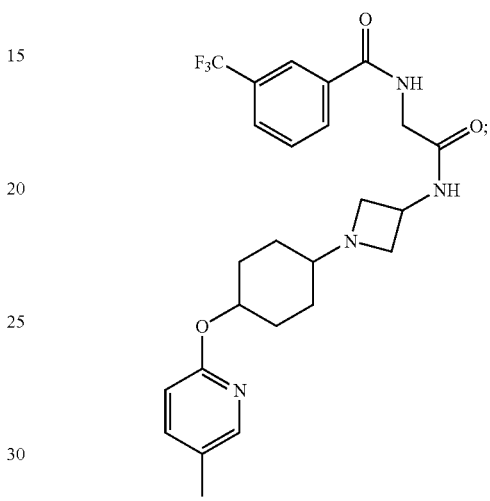
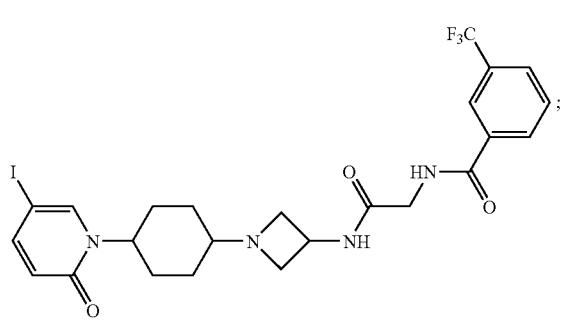
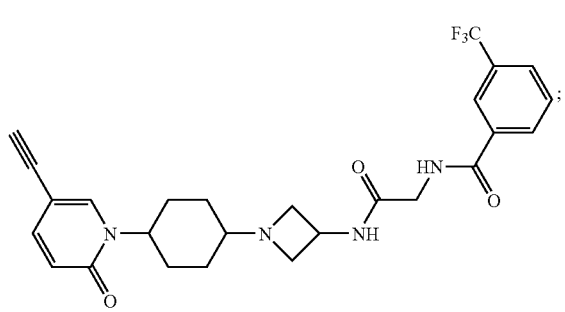
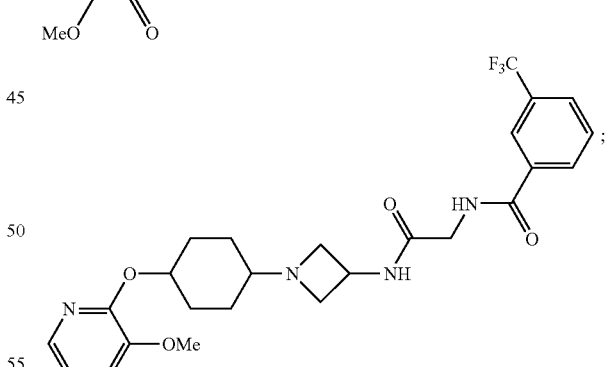
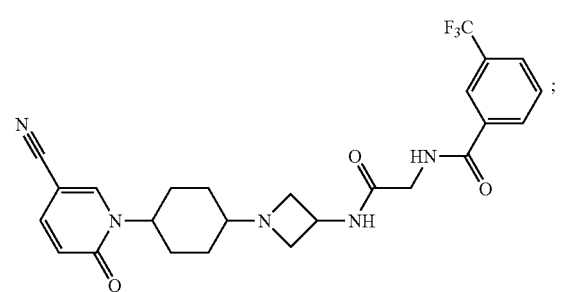
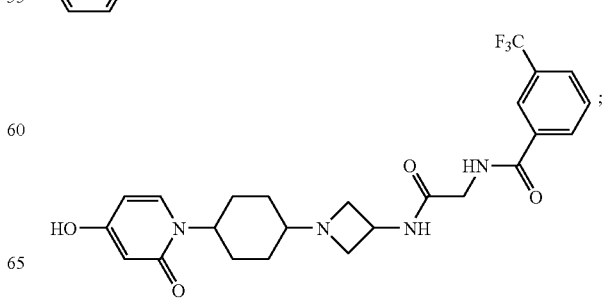

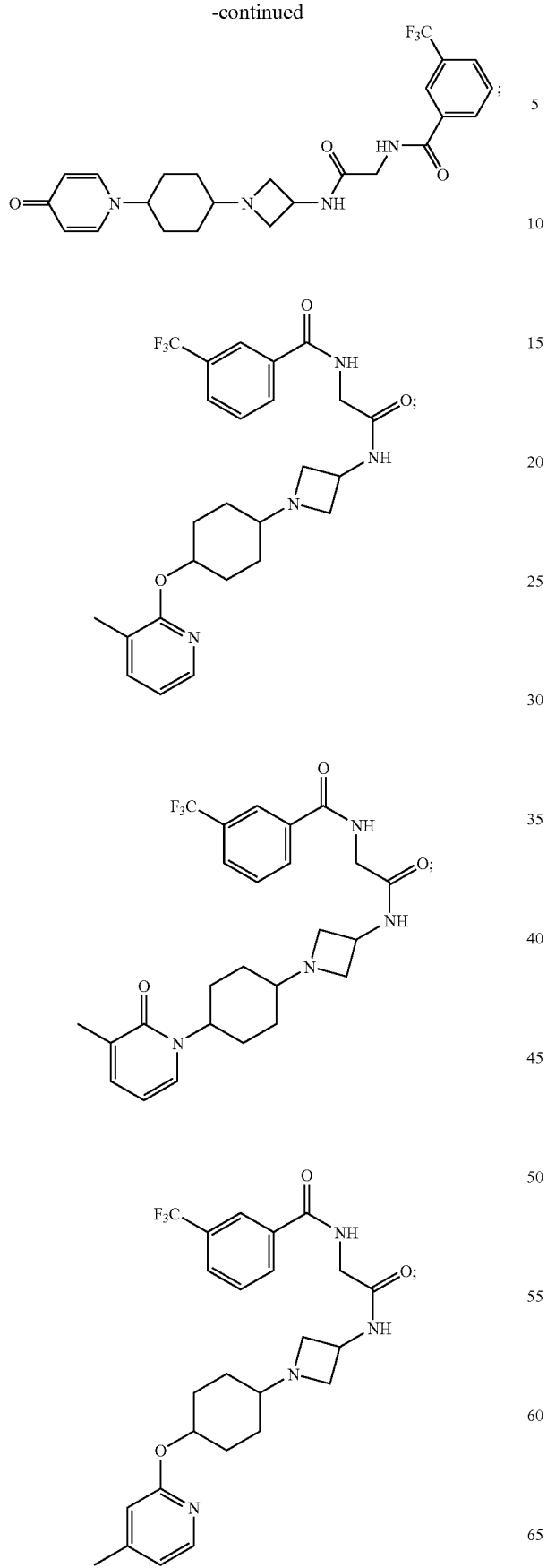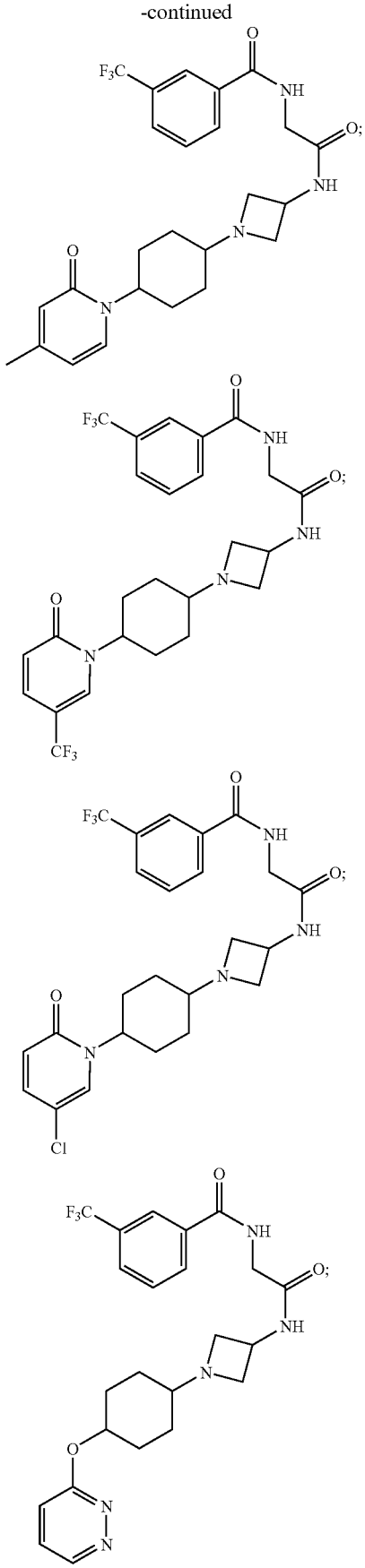

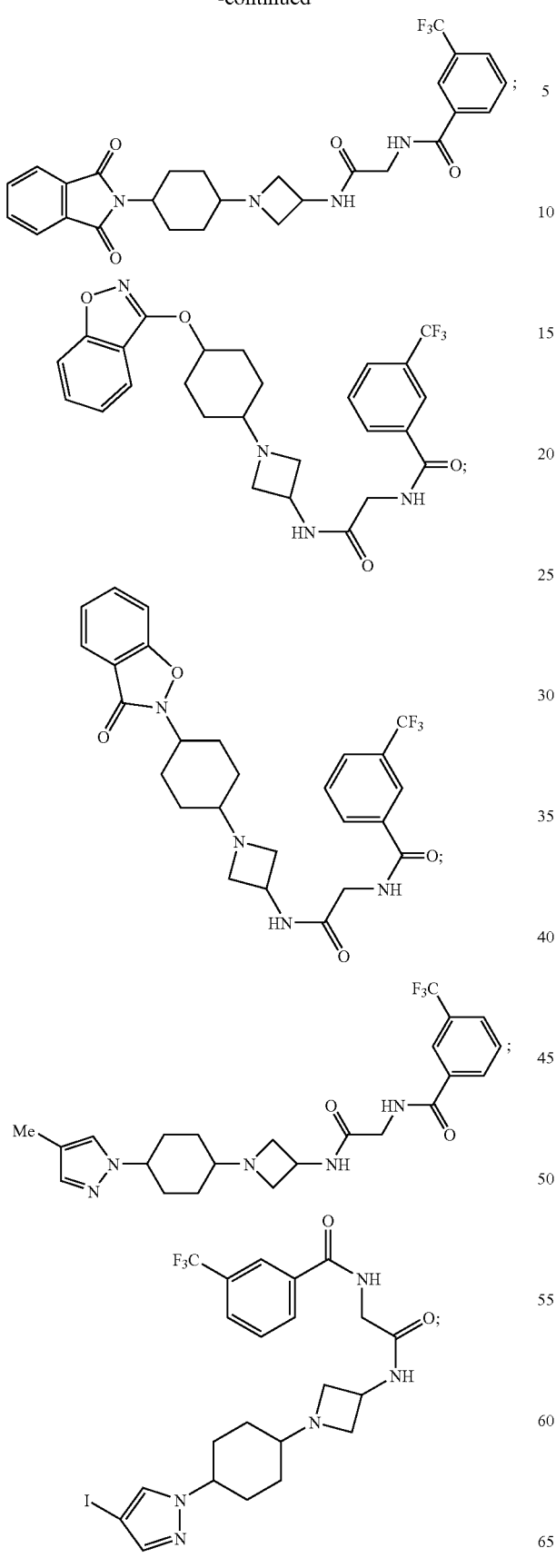
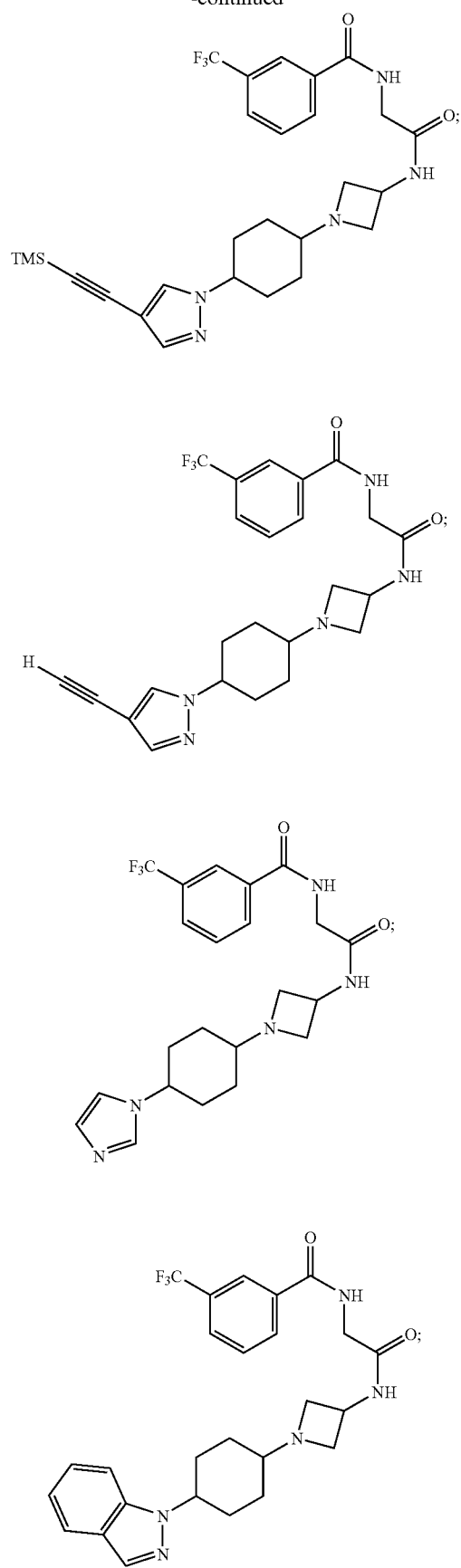

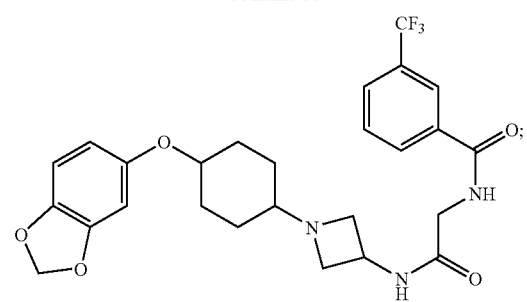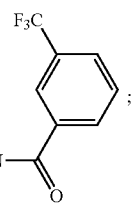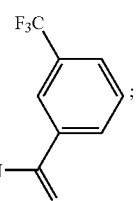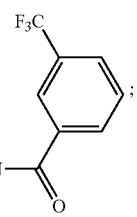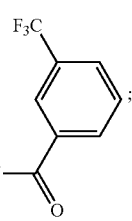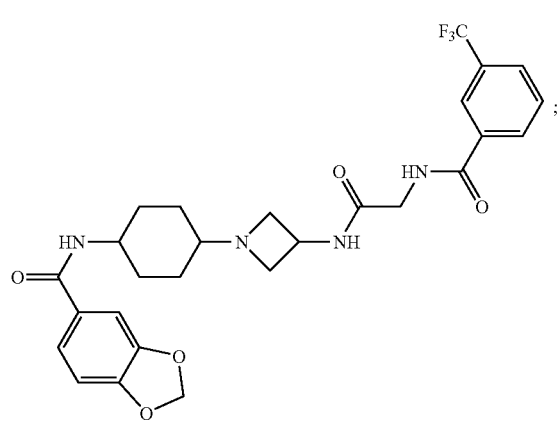

-continued

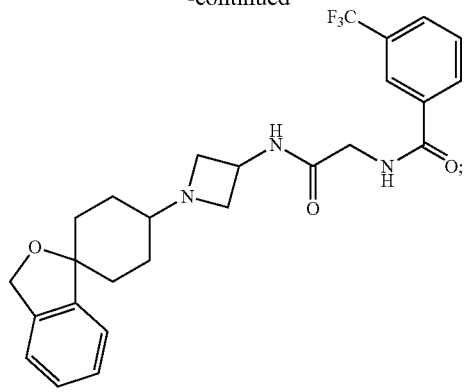

and solvates, hydrates, tautomers, prodrugs, and pharmaceutically acceptable salts thereof.

Another embodiment of the invention is a compound which is compound selected from the group consisting of:

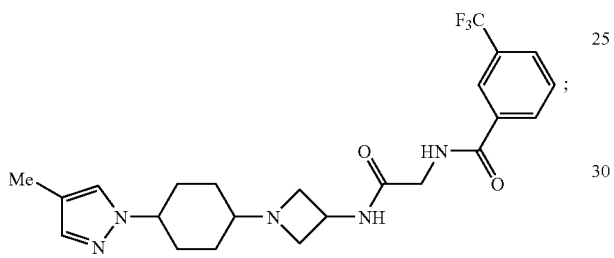

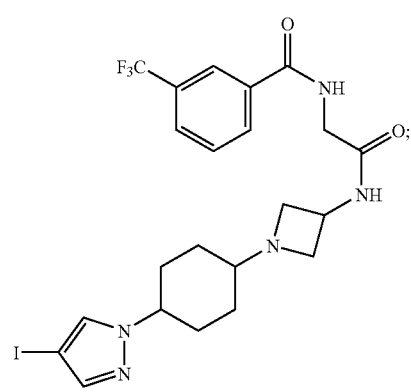

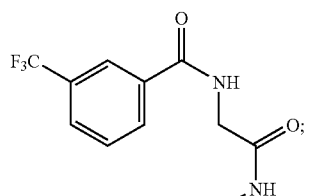

-continued

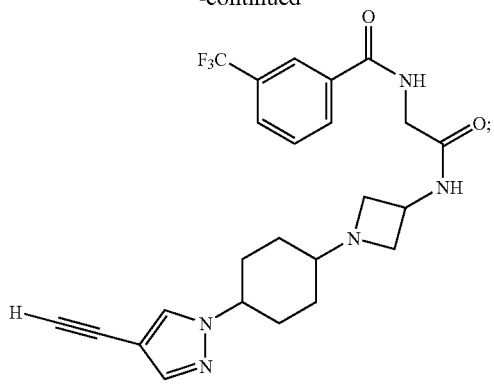

and solvates, hydrates, tautomers, prodrugs, and pharmaceutically acceptable salts thereof.

Another embodiment of the invention is a compound which is

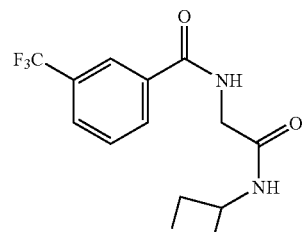

and solvates, hydrates, tautomers, prodrugs, and pharmaceutically acceptable salts thereof.

Another embodiment of the invention is a compound which is selected from the group consisting of:

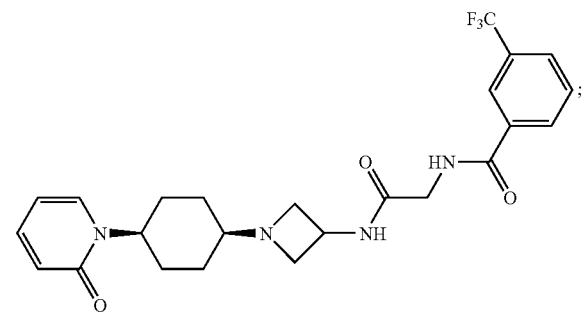

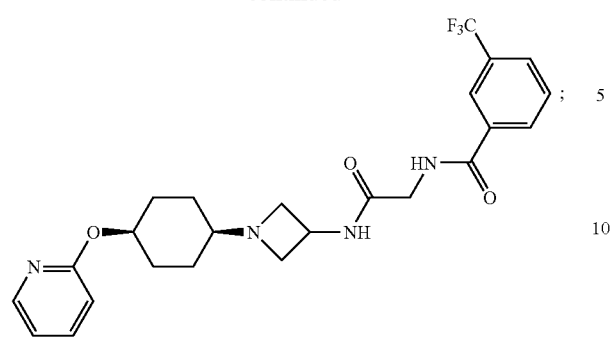
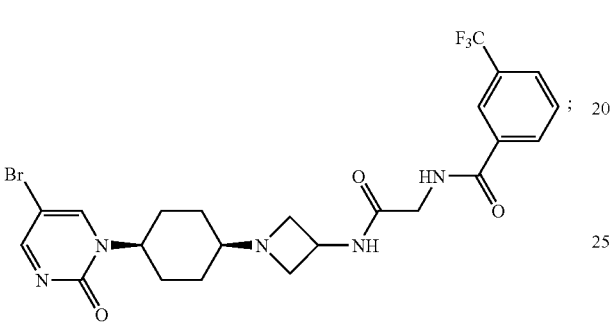
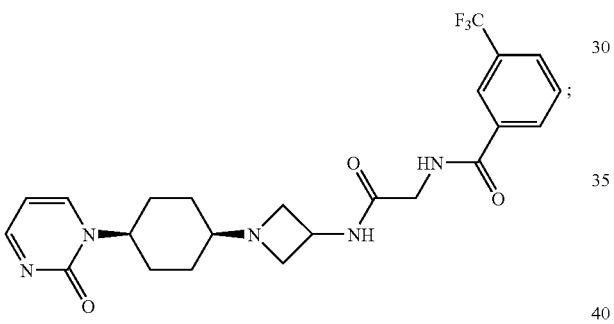
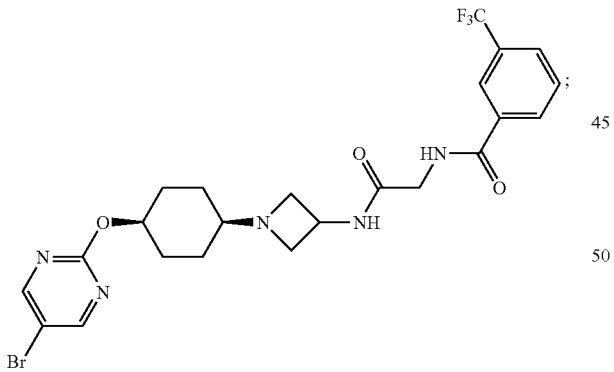
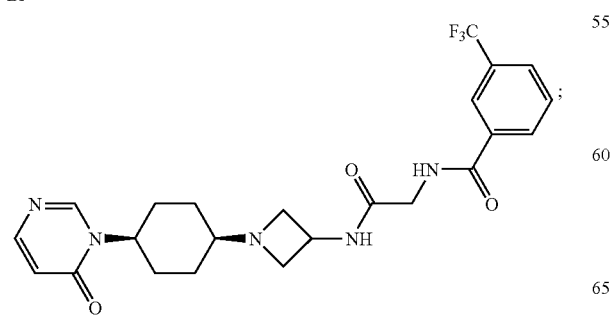
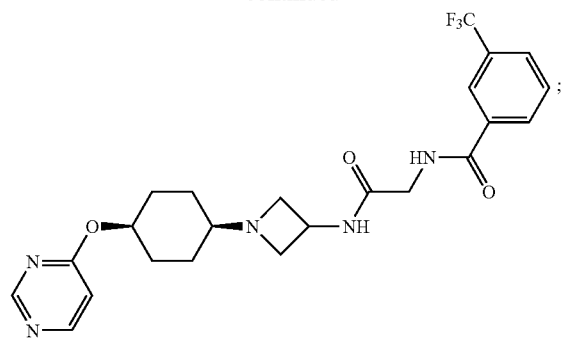
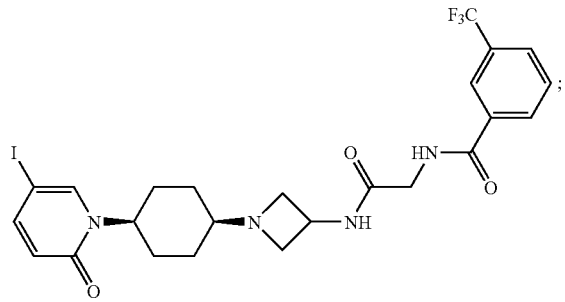
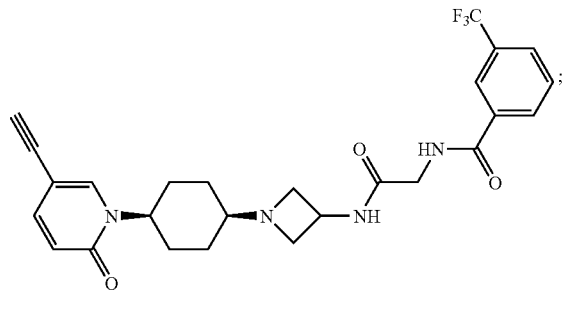
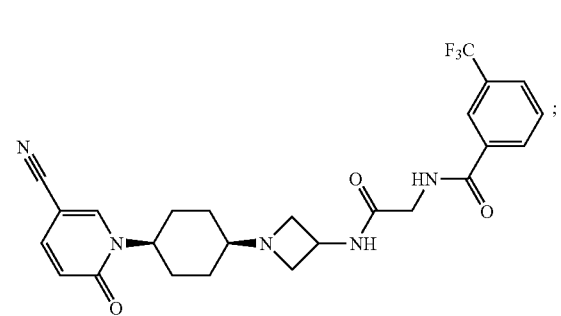
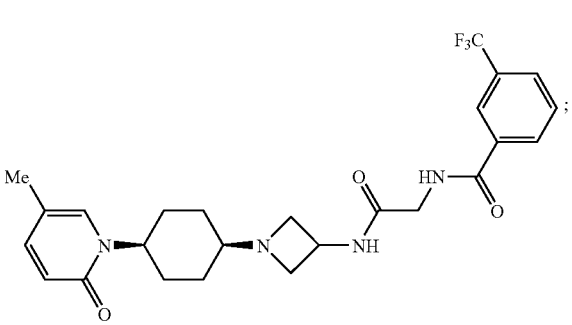

-continued
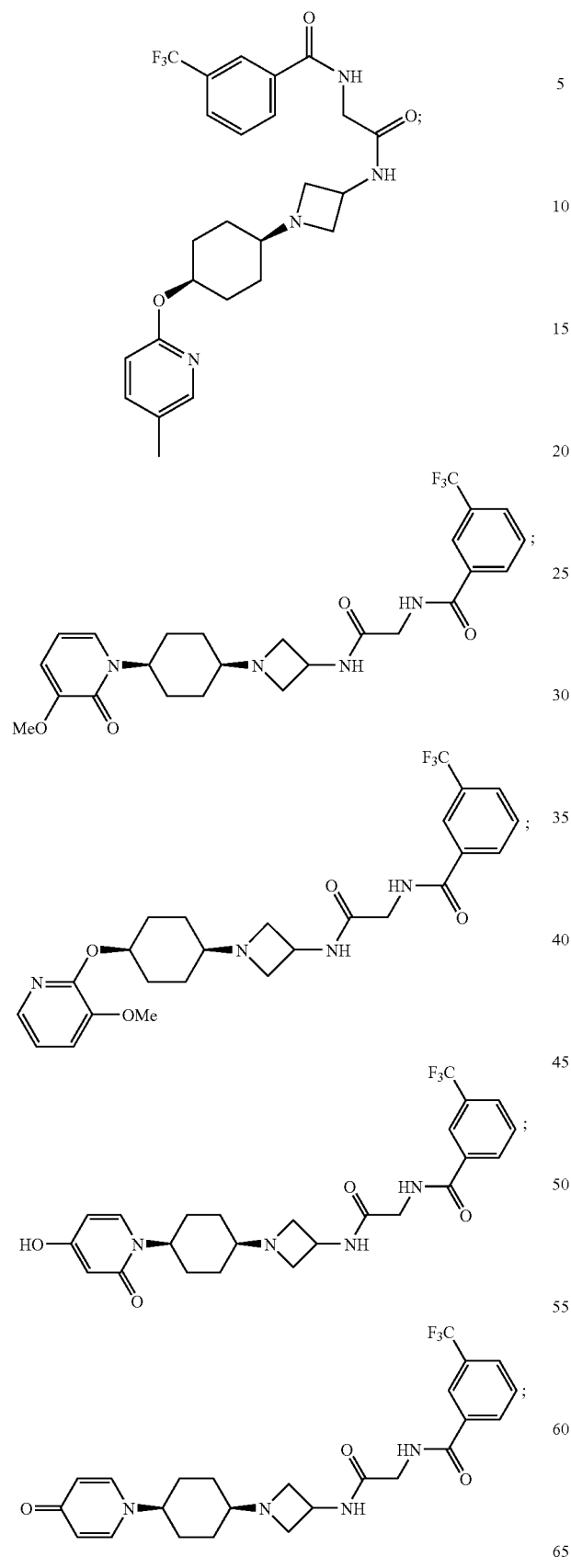
-continued
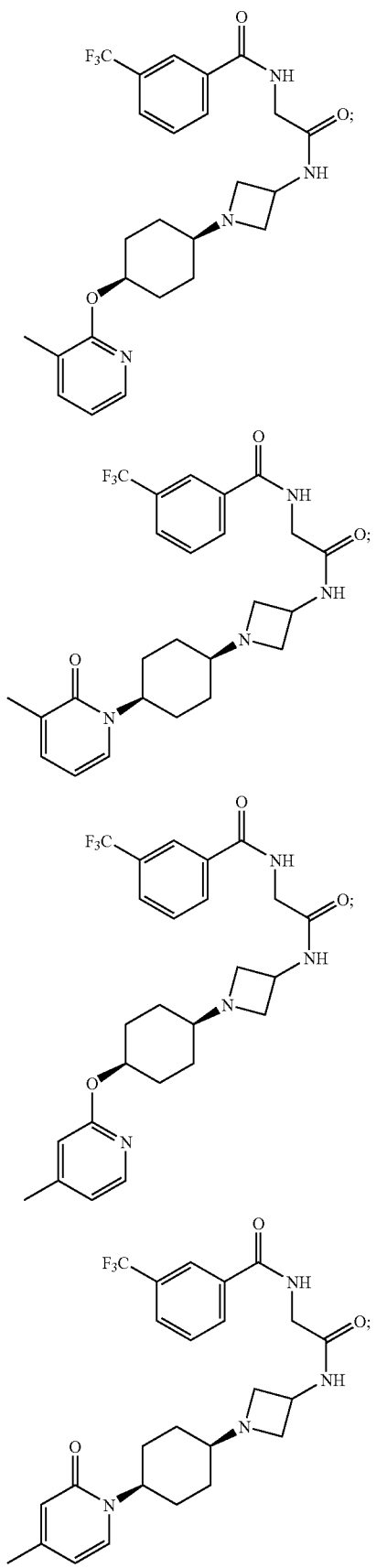

25
-continued
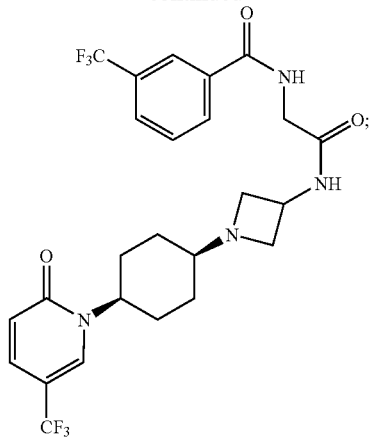
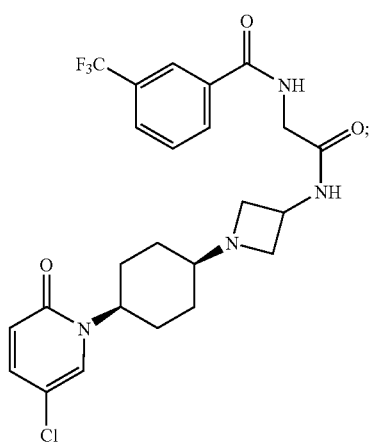
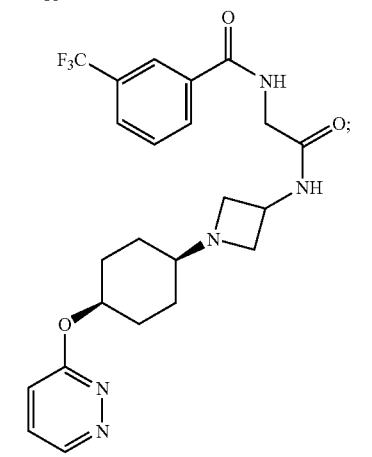
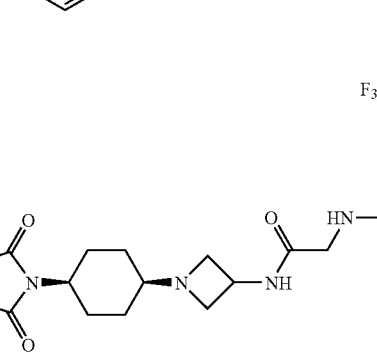
26
-continued
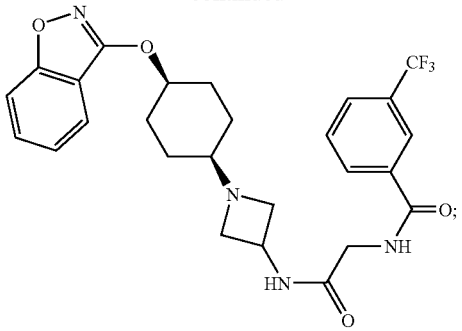
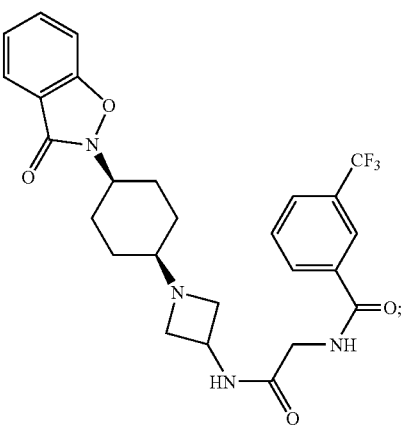
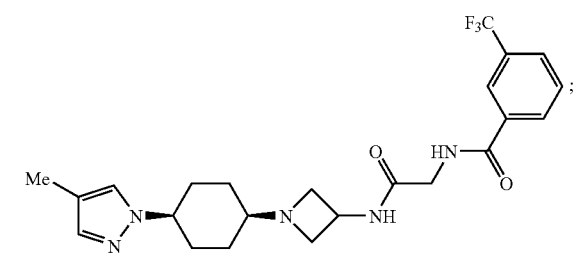
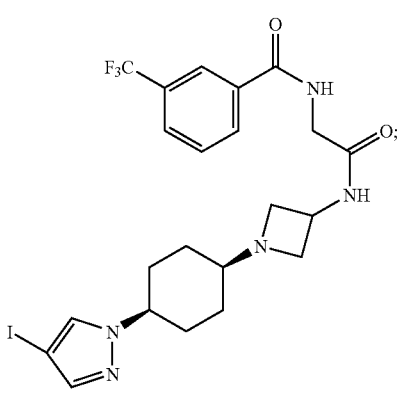

27
-continued
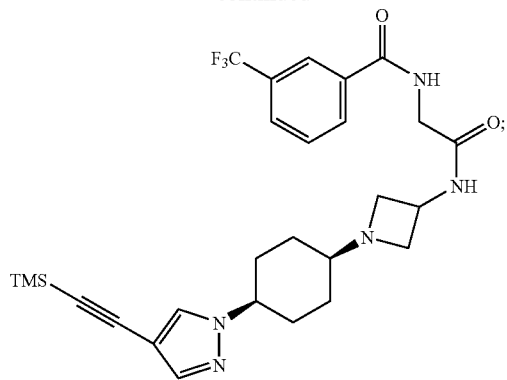
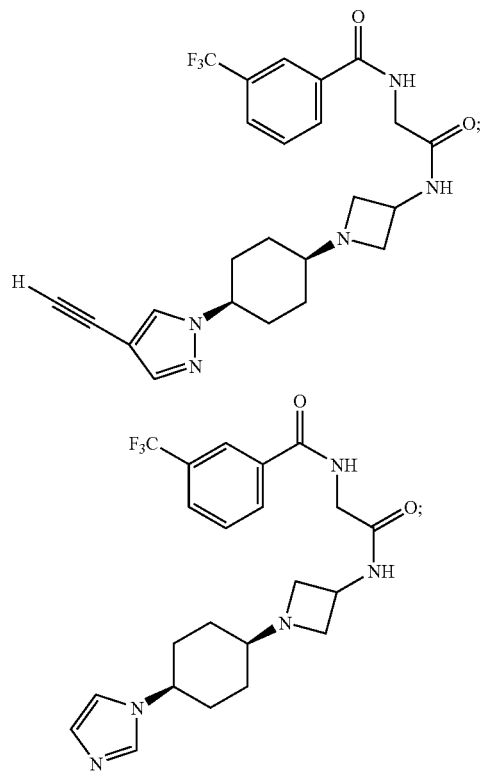
28
-continued
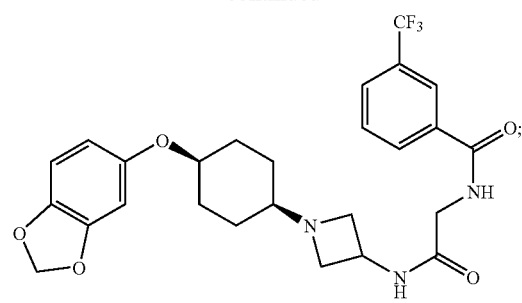
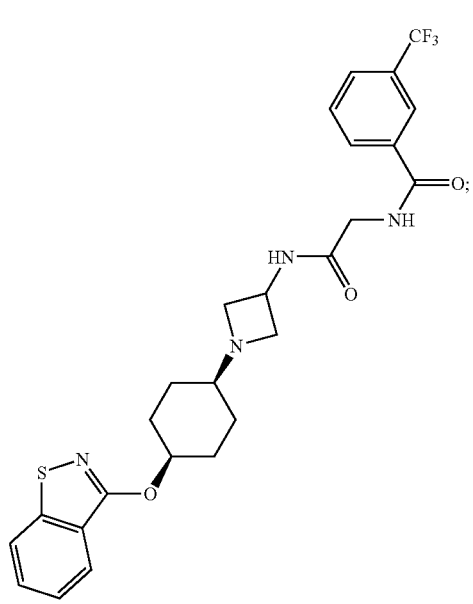
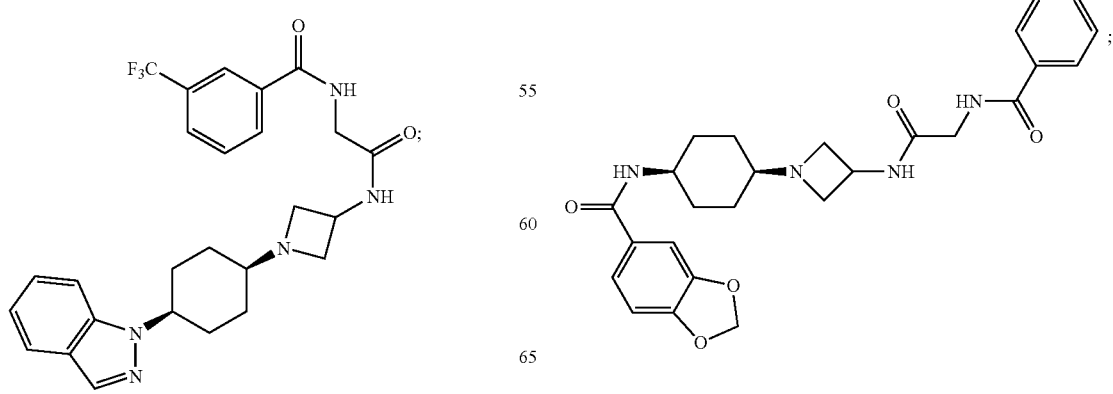

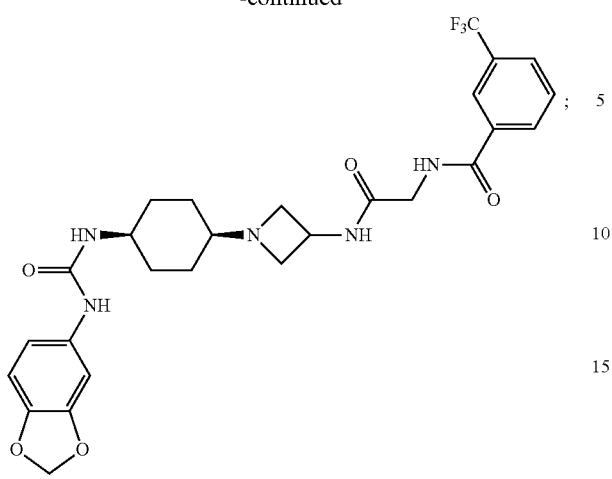
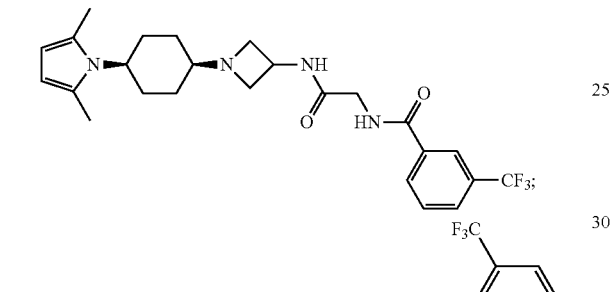
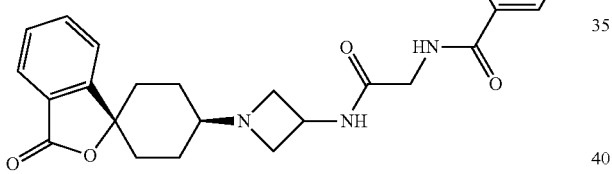
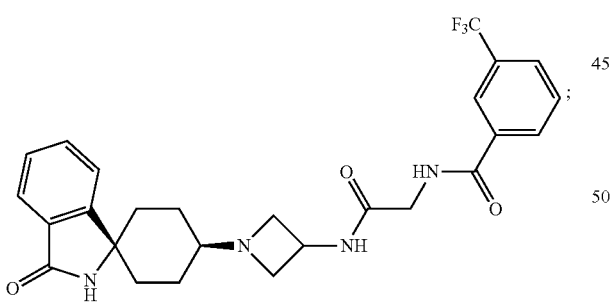
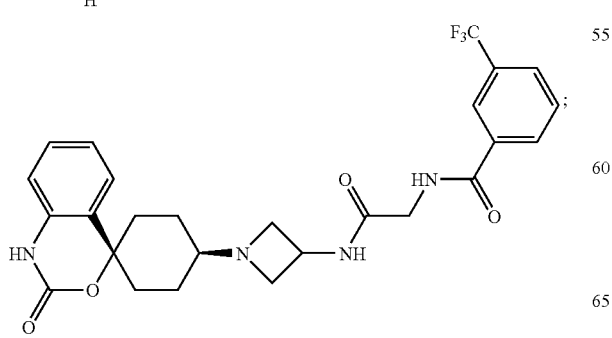
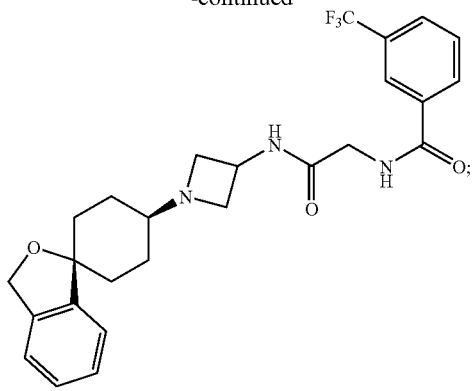
and solvates, hydrates, tautomers, prodrugs, and pharmaceutically acceptable salts thereof.
Another embodiment of the invention is a compound which is compound selected from the group consisting of:
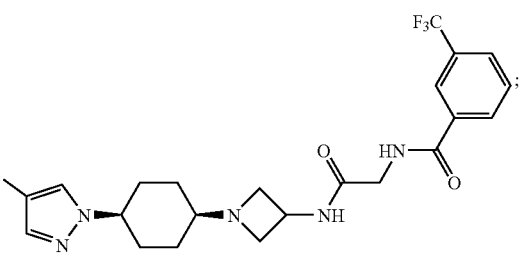
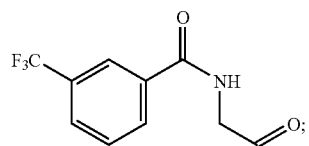
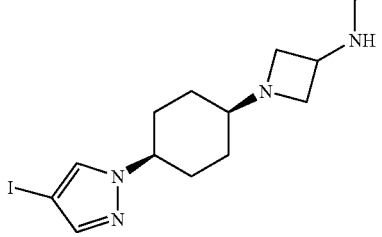
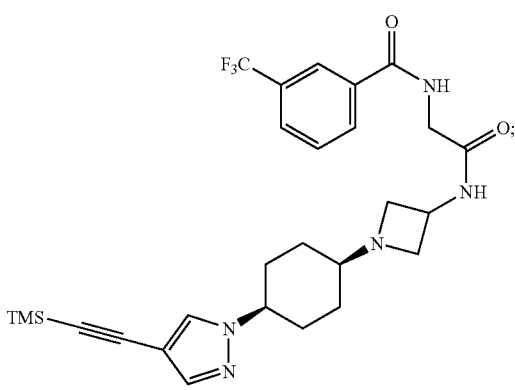

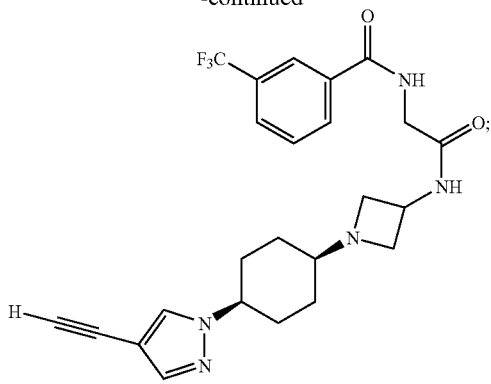

and solvates, hydrates, tautomers, prodrugs, and pharmaceutically acceptable salts thereof Another embodiment of the invention is a compound which is

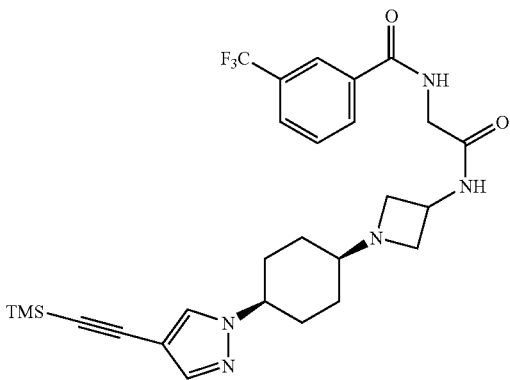

and solvates, hydrates, tautomers, prodrugs, and pharmaceutically acceptable salts thereof.

Another embodiment of the invention is a pharmaceutical composition, comprising a compound of Formula (I) and/or Formula (Ia) and a pharmaceutically acceptable carrier.

Another embodiment of the invention is a pharmaceutical composition, comprising a compound listed in the Examples section of this specification and a pharmaceutically acceptable carrier.

The present invention also provides a method for preventing, treating or ameliorating a CCR2 mediated syndrome, disorder or disease comprising administering to a subject in need thereof a therapeutically effective amount of a compound of Formula (I) and/or Formula (Ia) or a form, composition or medicament thereof. In one embodiment of the present invention, the CCR2 mediated syndrome, disorder or disease is an inflammatory syndrome, disorder or disease.

The present invention also provides a method for preventing, treating or ameliorating a CCR2 mediated inflammatory syndrome, disorder or disease wherein the syndrome, disorder or disease is associated with elevated MCP-1 expression or MCP-1 overexpression, or is an inflammatory condition that accompanies syndromes, disorders or diseases associated with elevated MCP-1 expression or MCP-1 overexpression comprising administering to a subject in need thereof a therapeutically effective amount of a compound of Formula (I) and/or Formula (Ia) or a form, composition or medicament thereof.

The present invention also provides a method of preventing, treating or ameliorating a syndrome, disorder or disease, wherein said syndrome, disorder or disease is selected from the group consisting of: Chronic Obstructive Pulmonary Disease (COPD), ophthalmic disorders, uveitis, atherosclerosis, rheumatoid arthritis, psoriasis, psoriatic arthritis, atopic dermatitis, multiple sclerosis, Crohn's Disease, ulcerative colitis, nephritis, organ allograft rejection, fibroid lung, renal insufficiency, type II diabetes and diabetic complications, diabetic nephropathy, obesity, weight disorders, diabetic retinopathy, diabetic retinitis, diabetic microangiopathy, tuberculosis, chronic obstructive pulmonary disease, sarcoidosis, invasive staphylococcia, inflammation after cataract surgery, allergic rhinitis, allergic conjunctivitis, chronic urticaria, asthma, allergic asthma, periodontal diseases, periodonitis, gingivitis, gum disease, diastolic cardiomyopathies, cardiac infarction, myocarditis, chronic heart failure, angiostenosis, restenosis, reperfusion disorders, glomerulonephritis, solid tumors and cancers, chronic lymphocytic leukemia, chronic myelocytic leukemia, multiple myeloma, malignant myeloma, Hodgkin's disease, and carcinomas of the bladder, breast, cervix, colon, lung, prostate, or stomach comprising administering to a subject in need thereof a therapeutically effective amount of a compound of Formula (I) and/or Formula (Ia) or a form, composition or medicament thereof In one embodiment, the present invention provides a method of treating or ameliorating a syndrome, disorder or disease, wherein said syndrome, disorder or disease is selected from the group consisting of: ophthalmic disorders, rheumatoid arthritis, psoriasis, psoriatic arthritis, atopic dermatitis, chronic obstructive pulmonary disease, allergic rhinitis, asthma, allergic asthma, and periodontal diseases comprising administering to a subject in need thereof a therapeutically effective amount of a compound of Formula (I) and/or Formula (Ia) or a form, composition or medicament thereof.

The invention also relates to methods of inhibiting CCR2 activity in a mammal by administration of an effective amount of at least one compound of Formula (I) and/or Formula (Ia).

In another embodiment, the invention relates to a product made by the process of any of Examples from Example 1 to Example 41.

In another embodiment, the invention relates to a compound which is the less polar isomer of any of Examples #1-41.

In another embodiment, the invention relates to a compound which is the less polar isomer of Example #29.

In another embodiment, the invention relates to a process for the preparation of a compound of Formula (I), comprising reacting a compound of Formula (V)

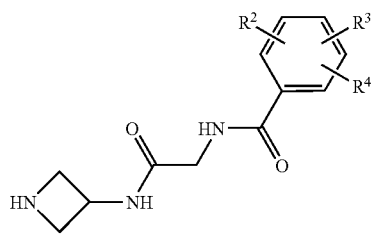

with a compound of Formula (VI)

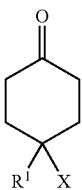

in the presence of a reducing agent to provide the compound of Formula (I).

In another embodiment, the invention relates to a product made by the above process.

In another embodiment, the invention relates to a process for the preparation of a compound of Formula (I), comprising reacting a compound of Formula (XIII)

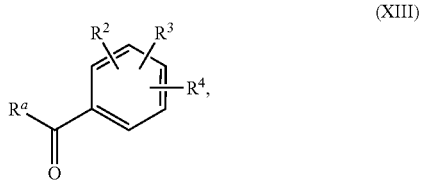

where $R_a$ is OH or Cl, with a compound of Formula (XII)

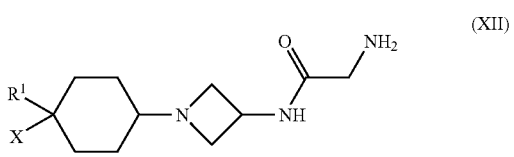

in the presence of HOBt/EDCI or $Et_3N$ to provide the compound of Formula (I).

In another embodiment, the invention relates to a product made by the above process.

In another embodiment, the invention relates to the use of hCCR2 knock-in mice to assess small molecule antagonists of CCR2 for use in the treatment of asthma.

In another embodiment, the invention relates to the use of hCCR2 knock-in mice to assess small molecule antagonists of CCR2 for use in the treatment of obesity.

In another embodiment, the invention relates to the use of hCCR2 knock-in mice to assess small molecule antagonists of CCR2 as described in Example 46.

In another embodiment, the invention relates to the use of hCCR2 knock-in mice to assess small molecule antagonists of CCR2 as described in Example 47.

In another embodiment, the invention relates to the use of hCCR2 knock-in mice to assess small molecule antagonists of CCR2 as described in Example 48.

DEFINITIONS

The term "alkyl" refers to both linear and branched chain radicals of up to 12 carbon atoms, preferably up to 6 carbon atoms, unless otherwise indicated, and includes, but is not limited to, methyl, ethyl, propyl, isopropyl, butyl, isobutyl, sec-butyl, tert-butyl, pentyl, isopentyl, hexyl, isohexyl, heptyl, octyl, 2,2,4-trimethylpentyl, nonyl, decyl, undecyl and dodecyl.

The term "$C_{(a-b)}$" (where a and b are integers referring to a designated number of carbon atoms) refers to an alkyl, alkenyl, alkynyl, alkoxy or cycloalkyl radical or to the alkyl portion of a radical in which alkyl appears as the prefix root containing from a to b carbon atoms inclusive. For example, $C_{(1-4)}$ denotes a radical containing 1, 2, 3 or 4 carbon atoms.

The term "cycloalkyl" refers to a saturated or partially unsaturated monocyclic or bicyclic hydrocarbon ring radical derived by the removal of one hydrogen atom from a single ring carbon atom. Typical cycloalkyl radicals include cyclopropyl, cyclobutyl, cyclopentyl, cyclopentenyl, cyclohexyl, cyclohexenyl, cycloheptyl and cyclooctyl. Additional examples include $C_{(3-8)}$cycloalkyl, $C_{(5-8)}$cycloalkyl, $C_{(3-12)}$cycloalkyl, $C_{(3-20)}$cycloalkyl, decahydronaphthalenyl, and 2,3,4,5,6,7-hexahydro-1H-indenyl.

The term "heterocyclyl" refers to a saturated or partially unsaturated monocyclic cycloalkyl ring radical wherein from 1 to 3 ring carbon atoms have been replaced with heteroatoms selected from N, O, or S. Said heteroatoms may exist in any allowed oxidation state. The radical may be derived from the removal of a hydrogen atom from a carbon or a nitrogen atom. Typical heterocyclyl radicals include, but are not limited to, 2H-pyrrolyl, 2-pyrrolinyl, 3-pyrrolinyl, pyrrolidinyl, 1,3-dioxolanyl, 2-imidazolinyl (also referred to as 4,5-dihydro-1H-imidazolyl), imidazolidinyl, 2-pyrazolinyl, pyrazolidinyl, tetrazolyl, piperidinyl, 1,4-dioxanyl, morpholinyl, 1,4-dithianyl, thiomorpholinyl, piperazinyl, azepanyl, hexahydro-1,4-diazepinyl and the like.

The term "heteroaromatic" or "heteroaryl" refers to 5- to 7-membered mono- or 8- to 10-membered bicyclic aromatic ring systems, containing from one to four heteroatoms selected from N, O, or S where the nitrogen and sulfur atoms can exist in any allowed oxidation state. Examples include, but are not limited to, benzimidazolyl, benzothiazolyl, benzothienyl, benzoxazolyl, furyl, imidazolyl, isothiazolyl, isoxazolyl, oxazolyl, pyrazinyl, pyrazolyl, pyridyl, pyrimidinyl, pyrrolyl, quinolinyl, thiazolyl and thienyl.

The term "heteroatom" refers to a nitrogen atom, an oxygen atom or a sulfur atom wherein the nitrogen and sulfur atoms can exist in any allowed oxidation states.

The term "pyridon-1-yl" refers to the functional groups

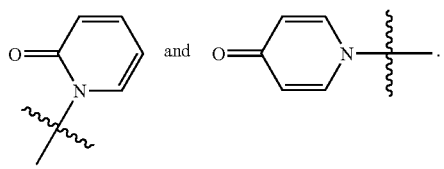

The term "pyrimidon-1-yl" refers to the functional group

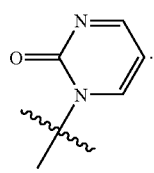

The term "oxo" refers to the functional group

For use in medicines, the salts of the compounds of this invention refer to non-toxic "pharmaceutically acceptable salts." FDA approved pharmaceutically acceptable salt forms (Ref. International J. Pharm. 1986, 33, 201-217; J. Pharm. Sci., 1977, January, 66(1), p1) include pharmaceutically acceptable acidic/anionic or basic/cationic salts.

Throughout this specification, compounds are described as being separated, usually by silica gel column, although preporatory thin layer chromatography, or high or low pressure liquid choromatography may also be used. It is generally accepted that when eluting compounds through a silica gel-type separation medium, that the least polar compounds elute before the more polar compounds. Therefore, the term "less polar isomer", refers to the isomer that will elute first from a silica gel type separation medium.

ABBREVIATIONS

Herein and throughout this application, the following abbreviations may be used.
BOC or Boc tert-butyloxycarbonyl
Bu butyl
DAST diethylaminosulfur trifluoride
DCC dicyclohexylcarbodiimide
DCM dicholomethane
DMF dimethylformamide
EDCI 1-ethyl-3-(3'-dimethylaminopropyl)carbodiimide
Et ethyl
EtOAc ethyl acetate
DIEA diisopropylethylamine
DPPA diphenylphosphorylazide
HOBt hydroxybenzotriazole
IPA isopropyl alcohol
Me methyl
Ms mesylate
M.S. molecular seives
OAc acetate
PdCl$_2$(dppf) [1,1'-bis(diphenylphosphino)ferrocene]dichloropalladium(II)
PPh$_3$ triphenylphosphine
iPr isopropyl
PyBrop bromo-tris-pyrrolidinophosphonium hexafluorophosphate
RT or rt room temperature
TBAF tetrabutylammonium fluoride
TEA triethylamine
TFA trifluoroacetic acid
THF tetrahydrofuran
Ts tosylate Pharmaceutically acceptable acidic/anionic salts include, and are not limited to acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, methylbromide, methylnitrate, methylsulfate, mucate, napsylate, nitrate, pamoate, pantothenate, phosphate/diphosphate, polygalacturonate, salicylate, stearate, subacetate, succinate, sulfate, tannate, tartrate, teoclate, tosylate and triethiodide. Organic or inorganic acids also include, and are not limited to, hydriodic, perchloric, sulfuric, phosphoric, propionic, glycolic, methanesulfonic, hydroxyethanesulfonic, oxalic, 2-naphthalenesulfonic, p-toluenesulfonic, cyclohexanesulfamic, saccharinic or trifluoroacetic acid.

Pharmaceutically acceptable basic/cationic salts include, and are not limited to aluminum, 2-amino-2-hydroxymethyl-propane-1,3-diol (also known as tris(hydroxymethyl)aminomethane, tromethane or "TRIS"), ammonia, benzathine, t-butylamine, calcium, calcium gluconate, calcium hydroxide, chloroprocaine, choline, choline bicarbonate, choline chloride, cyclohexylamine, diethanolamine, ethylenediamine, lithium, LiOMe, L-lysine, magnesium, meglumine, NH$_3$, NH$_4$OH, N-methyl-D-glucamine, piperidine, potassium, potassium-t-butoxide, potassium hydroxide (aqueous), procaine, quinine, sodium, sodium carbonate, sodium-2-ethylhexanoate (SEH), sodium hydroxide, triethanolamine or zinc.

Methods of Use

The present invention is directed to a method for preventing, treating or ameliorating a CCR2 mediated syndrome, disorder or disease comprising administering to a subject in need thereof an effective amount of a compound of Formula (I) and/or Formula (Ia) or a form, composition or medicament thereof.

Examples of syndrome, disorder or disease for which the compounds of Formula (I) and/or Formula (Ia) are useful include ophthalmic disorders, uveitis, atherosclerosis, rheumatoid arthritis, psoriasis, psoriatic arthritis, atopic dermatitis, multiple sclerosis, Crohn's Disease, ulcerative colitis, nephritis, organ allograft rejection, fibroid lung, renal insufficiency, type-I diabetes, type II diabetes and diabetic complications, diabetic nephropathy, diabetic retinopathy, diabetic retinitis, diabetic microangiopathy, overweight, obesity, obesity-associated insulin resistance, tuberculosis, chronic obstructive pulmonary disease, sarcoidosis, invasive staphyloccocia, inflammation after cataract surgery, allergic rhinitis, allergic conjunctivitis, chronic urticaria, asthma, allergic asthma, periodontal diseases, periodontis, gingivitis, gum disease, diastolic cardiomyopathies, cardiac infarction, myocarditis, chronic heart failure, angiostenosis, restenosis, reperfusion disorders, glomerulonephritis, solid tumors and cancers, chronic lymphocytic leukemia, chronic myelocytic leukemia, multiple myeloma, malignant myeloma, Hodgkin's disease, and carcinomas of the bladder, breast, cervix, colon, lung, prostate, or stomach.

The term "administering" with respect to the methods of the invention, means a method for therapeutically or prophylactically preventing, treating or ameliorating a syndrome, disorder or disease as described herein by using a compound of Formula (I) and/or Formula (Ia) or a form, composition or medicament thereof. Such methods include administering an effective amount of said compound, compound form, composition or medicament at different times during the course of a therapy or concurrently in a combination form. The methods of the invention are to be understood as embracing all known therapeutic treatment regimens.

The term "subject" refers to a patient, which may be animal, typically a mammal, typically a human, which has been the object of treatment, observation or experiment. In one aspect of the invention, the subject is at risk of (or susceptible to) developing a syndrome, disorder or disease that is associated with elevated MCP-1 expression or MCP-1 overexpression, or a patient with an inflammatory condition that accompanies syndromes, disorders or diseases associated with elevated MCP-1 expression or MCP-1 overexpression.

The term "therapeutically effective amount" means that amount of active compound or pharmaceutical agent that elicits the biological or medicinal response in a tissue system, animal or human, that is being sought by a researcher, veterinarian, medical doctor, or other clinician, which includes preventing, treating or ameliorating the symptoms of a syndrome, disorder or disease being treated.

The term "uveitis" generically refers to any inflammatory disease involving the eye. Uveitis can be divided into clinically distinct subtypes based on the part of the eye in which the inflammation is present (percentages correspond to patients known to fit these categories): anterior (51%), intermediate (13%), posterior (20%), or panuveitis (16%) and, according to the course of the disease, as either acute (16%), recurring (26%), or chronic (58%). Those with anterior uveitis (·19%) eventually develop irreparable vision damage despite aggressive treatment such as unilateral blindness (9%), bilateral blindness (2%), or unilateral or bilateral vision impairment (8%). Most cases of uveitis are idiopathic, but known causes include infection (e.g., toxoplasmosis, cytomegalovirus, and the like) or development as a component of a systemic inflammatory and/or autoimmune disorder (e.g., juvenile RA, HLA-B27 associated spondyloarthropathies, sarcoidosis, and the like). (HLA-B27: Human Leukocyte Antigen B*27- is a class I surface antigen encoded by the B locus in the major histocompatibility complex (MHC) on chromosome 6 and presents microbial antigens to T cells. HLA-B27 is strongly associated with a certain set of autoimmune diseases referred to as the seronegative spondyloarthropathies.)

When employed as CCR2 inhibitors, the compounds of the invention may be administered in an effective amount within the dosage range of about 0.5 mg to about 10 g, preferably between about 0.5 mg to about 5 g, in single or divided daily doses. The dosage administered will be affected by factors such as the route of administration, the health, weight and age of the recipient, the frequency of the treatment and the presence of concurrent and unrelated treatments.

It is also apparent to one skilled in the art that the therapeutically effective dose for compounds of the present invention or a pharmaceutical composition thereof will vary according to the desired effect. Therefore, optimal dosages to be administered may be readily determined by one skilled in the art and will vary with the particular compound used, the mode of administration, the strength of the preparation, and the advancement of the disease condition. In addition, factors associated with the particular subject being treated, including subject age, weight, diet and time of administration, will result in the need to adjust the dose to an appropriate therapeutic level. The above dosages are thus exemplary of the average case. There can, of course, be individual instances where higher or lower dosage ranges are merited, and such are within the scope of this invention.

The compounds of Formula (I) and/or Formula (Ia) may be formulated into pharmaceutical compositions comprising any known pharmaceutically acceptable carriers. Exemplary carriers include, but are not limited to, any suitable solvents, dispersion media, coatings, antibacterial and antifungal agents and isotonic agents. Exemplary excipients that may also be components of the formulation include fillers, binders, disintegrating agents and lubricants.

The pharmaceutically-acceptable salts of the compounds of Formula (I) and/or Formula (Ia) include the conventional non-toxic salts or the quaternary ammonium salts which are formed from inorganic or organic acids or bases. Examples of such acid addition salts include acetate, adipate, benzoate, benzenesulfonate, citrate, camphorate, dodecylsulfate, hydrochloride, hydrobromide, lactate, maleate, methanesulfonate, nitrate, oxalate, pivalate, propionate, succinate, sulfate and tartrate. Base salts include ammonium salts, alkali metal salts such as sodium and potassium salts, alkaline earth metal salts such as calcium and magnesium salts, salts with organic bases such as dicyclohexylamino salts and salts with amino acids such as arginine. Also, the basic nitrogen-containing groups may be quaternized with, for example, alkyl halides.

The pharmaceutical compositions of the invention may be administered by any means that accomplish their intended purpose. Examples include administration by parenteral, subcutaneous, intravenous, intramuscular, intraperitoneal, transdermal, buccal or ocular routes. Alternatively or concurrently, administration may be by the oral route. Suitable formulations for parenteral administration include aqueous solutions of the active compounds in water-soluble form, for example, water-soluble salts, acidic solutions, alkaline solutions, dextrose-water solutions, isotonic carbohydrate solutions and cyclodextrin inclusion complexes.

The present invention also encompasses a method of making a pharmaceutical composition comprising mixing a pharmaceutically acceptable carrier with any of the compounds of the present invention. Additionally, the present invention includes pharmaceutical compositions made by mixing a pharmaceutically acceptable carrier with any of the compounds of the present invention. As used herein, the term "composition" is intended to encompass a product comprising the specified ingredients in the specified amounts, as well as any product which results, directly or indirectly, from combinations of the specified ingredients in the specified amounts.

Polymorphs and Solvates

Furthermore, the compounds of the present invention may have one or more polymorph or amorphous crystalline forms and as such are intended to be included in the scope of the invention. In addition, the compounds may form solvates, for example with water (i.e., hydrates) or common organic solvents. As used herein, the term "solvate" means a physical association of the compounds of the present invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. The term "solvate" is intended to encompass both solution-phase and isolatable solvates. Non-limiting examples of suitable solvates include ethanolates, methanolates, and the like.

It is intended that the present invention include within its scope polymorphs and solvates of the compounds of the present invention. Thus, in the methods of treatment of the present invention, the term "administering" shall encompass the means for treating, ameliorating or preventing a syndrome, disorder or disease described herein with the compounds of the present invention or a polymorph or solvate thereof, which would obviously be included within the scope of the invention albeit not specifically disclosed.

In another embodiment, the invention relates to a compound as described in the Examples or Formula (I) and/or Formula (Ia) for use as a medicament.

In another embodiment, the invention relates to the use of a compound as described in the Examples of Formula (I)

and/or Formula (Ia) for the preparation of a medicament for the treatment of a disease associated with an elevated or inappropriate CCR2 activity.

The present invention includes within its scope prodrugs of the compounds of this invention. In general, such prodrugs will be functional derivatives of the compounds which are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs", Ed. H. Bundgaard, Elsevier, 1985.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-D-tartaric acid and/or (+)-di-p-toluoyl-L-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J.F.W. McOmie, Plenum Press, 1973; and T.W. Greene & P.G.M. Wuts, *Protective Groups in Organic Synthesis*, John Wiley & Sons, 1991. The protecting groups may be removed at a convenient subsequent stage using methods known from the art.

General Reaction Schemes

Representative compounds of the present invention can be synthesized in accordance with the general synthetic methods described below. Compounds of Formula (I) can be prepared by methods known to those who are skilled in the art. The following reaction schemes are only meant to represent examples of the invention and are in no way meant to be a limit of the invention.

Compounds of Formula (I) may be prepared according to the processes outlined in Scheme 1.

Scheme 1

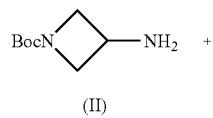

+

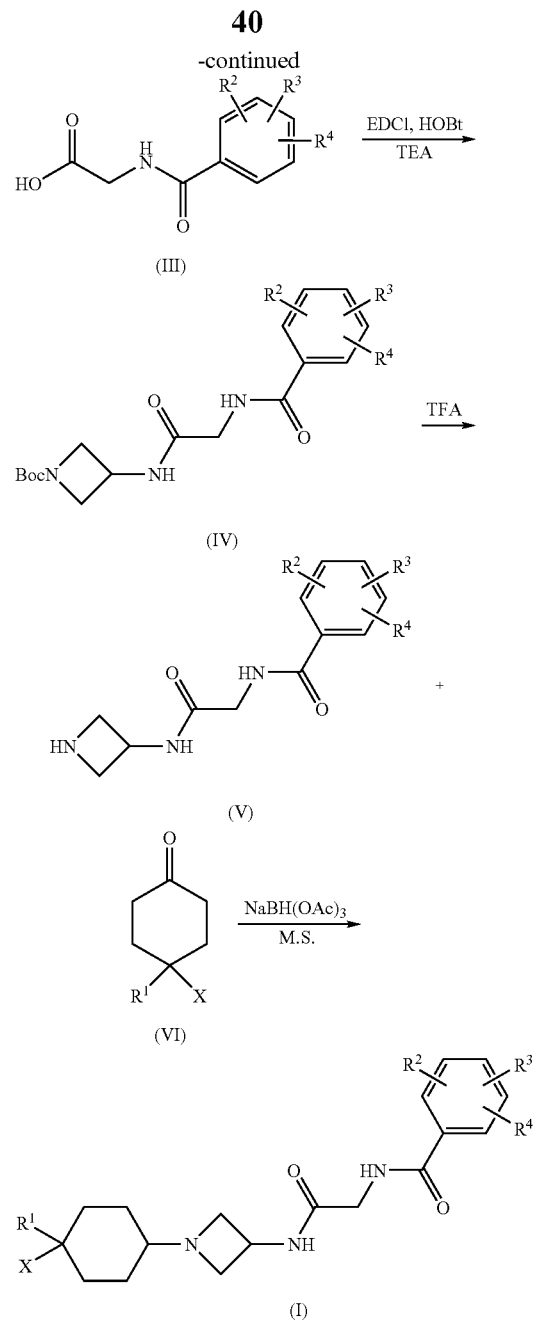

Scheme 1 illustrates a synthetic route leading to compounds of Formula (I). Commercially available azetidine (II) is reacted with acid (III), wherein (III) is prepared according to the procedure described by Ingersoll, A. W. et. al., Organic Syntheses 1932, XII, 40-2 substituting commercially available

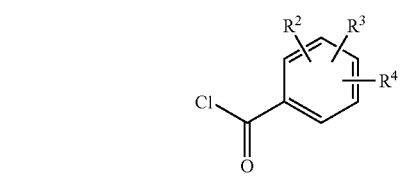

for benzoyl chloride, in the presence of a coupling reagent such as EDCI/HOBt, PyBrop, or DCC, in an organic solvent such as THF, dichloromethane or 1,2-dichloroethane, at a temperature in the range of about 0° C. to about 25° C., to yield the corresponding amide (IV).

Amide (IV) is treated with an acid such as 1N HCl, 1N H₂SO₄ or trifluoroacetic acid in an organic solvent such as diethyl ether, THF, dichloromethane or dioxane, at a temperature in the range of about 0° C. to about 25° C. to yield amine (V).

Amine (V) is reacted with a suitably substituted ketone (VI), in the presence of a reducing reagent such as NaBH₄, NaBH(CN)₃ or NaBH(OAc)₃, in an organic base such as triethylamine, diethylpropylamine or N-methylmorpholine with or without molecule sieves, in an organic solvent such as dichloromethane, 1,2-dichloroethane or THF, at a temperature in the range of 0° C. to about 25° C., to yield the corresponding azetidine (I).

Alternatively, compounds of Formula (I) may be prepared according to the processes outlined in Scheme 2.

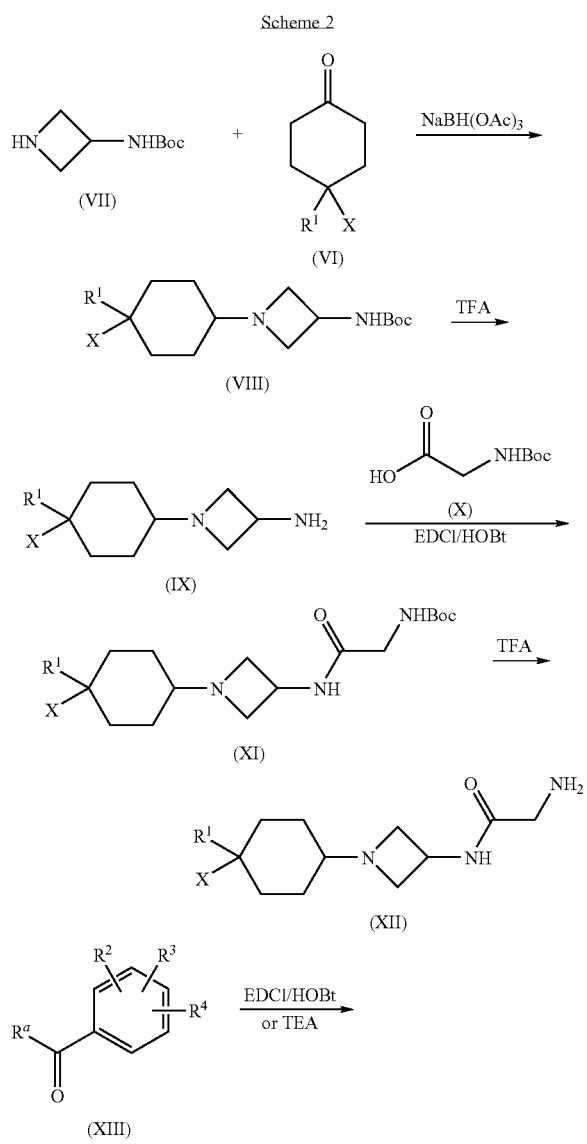

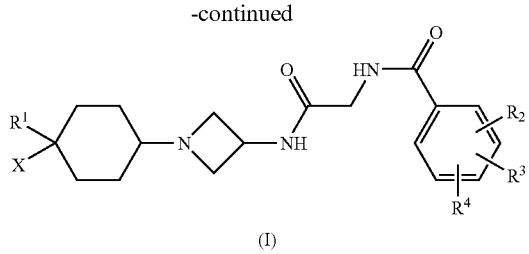

Commercially available azetidine (VII) is reacted with a suitably substituted ketone (VI), in the presence of a reducing reagent such as NaBH₄, NaBH(CN)₃ or NaBH(OAc)₃, in an organic base such as triethylamine, diethylpropylamine or N-methylmorpholine, with or without molecule sieves, in an organic solvent such as dichloromethane, 1,2-dichloroethane or THF at a temperature in the range of 0° C. to about 25° C., to yield the corresponding azetidine (VIII).

Azetidine (VIII) is treated with 1N HCl, 1N H₂SO₄ or trifluoroacetic acid in an organic solvent such as diethyl ether, THF, dioxane or dichloromethane, at a temperature in the range of about 0° C. to about 25° C., to yield the corresponding amine (IX).

Amine (IX) is reacted with acid (X), in the presence of a coupling reagent such as EDCl/HOBt, PyBrop or DCC, in an organic solvent such as THF, dichloromethane or 1,2-dichloroethane, at a temperature in the range of about 0° C. to about 25° C., to yield the corresponding azetidine (XI).

Azetidine (XI) is treated with 1N HCl or H₂SO₄ or trifluoroacetic acid, in an organic solvent such as diethyl ether, THF or dioxane, at a temperature in the range of about 0° C. to about 25° C., to yield the corresponding amine (XII).

Amine (XII) is reacted with acid (XIII). When R$^a$ is OH, the reaction is performed in the presence of a coupling reagent such as EDCl/HOBt, PyBrop or DCC, in an organic solvent such as THF, dichloromethane or 1,2-dichloroethane, at a temperature in the range of about 0° C. to about 25° C. When R$^a$ is Cl, the reaction is performed in the presence of an organic base such triethylamine, diethylpropylamine or N-methylmorpholine, in an organic solvent such as THF, dichloromethane or 1,2-dichloroethane, at a temperature in the range of about 0° C. to about 25° C., to yield the corresponding azetidine (I).

Compounds of Formula (I) may be derived from ketone (VI). Preparation of (VI) is outlined in Scheme 3.

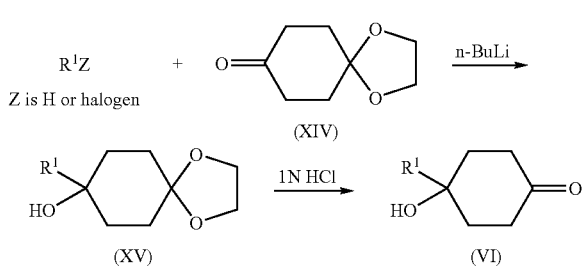

Commercially available aryl halide or aryl alkane R¹Z (where R¹ is as defined in Formula (I)) is reacted with commercially available ketone (XIV) in the presence of organometalic agent such as n-BuLi, i-PrMgBr or i-PrMgCl, in an organic solvent such as ether, THF or dioxane, at a temperature in the range of about –78° C. to about 0° C., to yield the corresponding ketal (XV).

Ketal (XV) is treated with an acid such as 1N HCl or 1N H₂SO₄ in an organic solvent such as acetone, acetonitrile or THF, at a temperature in the range of about 0° C. to about 25° C., to yield the corresponding ketone (VI).

Compounds of Formula (I) may be derived from ketone (XIX). Preparation of (XIX) is outlined in Scheme 4.

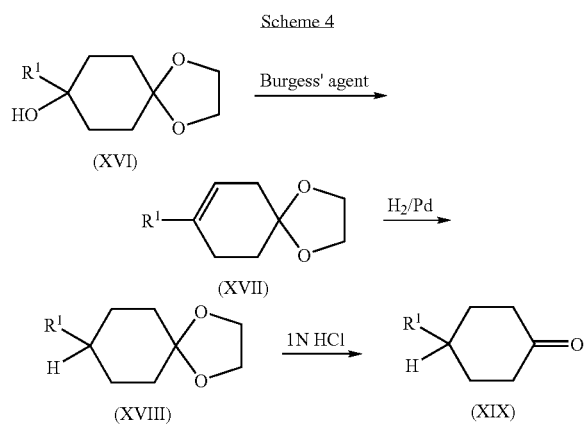

Ketal (XVI) is treated with a dehydrating agent such as Burgess' reagent, in an organic solvent such as ether, THF or dioxane, at a temperature in the range of about 0° C. to about 25° C., to yield the corresponding alkene (XVII).

Alkene (XVII) is treated with hydrogen gas under pressure from 5 to 50 psi catalyzed by 5-10% Pd/C, in an organic solvent such as methanol, at a temperature in the range of about 25° C. to about 50° C., to yield the corresponding alkane (XVIII).

Alkane (XVIII) is treated with 1N HCl or 1N H₂SO₄, in an organic solvent such as acetone, acetonitrile or THF, at a temperature in the range of about 0° C. to about 25° C., to yield the corresponding ketone (XIX).

Alternatively compound (XVII) may be prepared according to the processes outlined in Scheme 5.

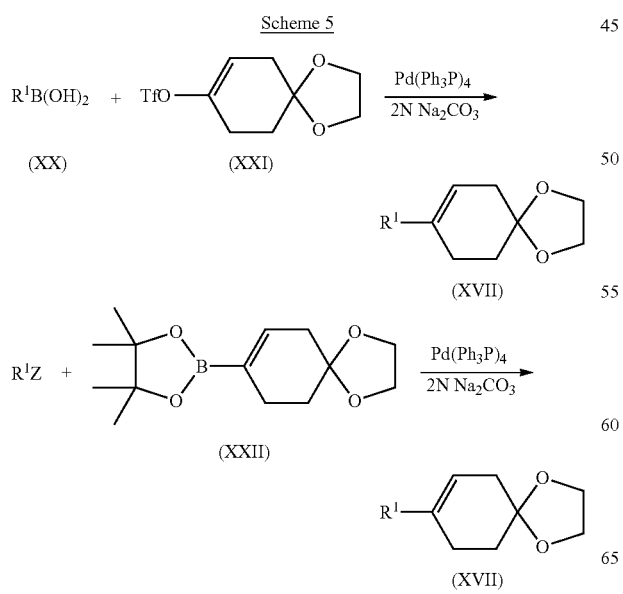

Z is halogen

Commercially available aryl boronic acid (XX), (wherein $R^1$ is as defined in Formula (I)) is reacted with vinyl triflate (XXI) prepared according to the procedure of Pearson, W. et. al., *J. Org. Chem.* 2004, 69, 9109-9122, in the presence of a catalyst such as Pd(Ph₃P)₄, PdCl₂(Ph₃P)₂ or PdCl₂(dppf) and a base such as 2N Na₂CO₃ or K₂CO₃, in an organic solvent such as toluene, dioxane or THF, at a temperature in the range of about 80° C. to about 120° C., to yield the corresponding alkene (XVII).

Alternatively, commercially available aryl or heteroaryl halide $R^1Z$ is reacted with vinyl boronic ester (XXII) prepared according to Birch, A. M. et. al., PCT Int. Appl. 2006, WO 2006064189, in the presence of a catalyst such as Pd(Ph₃P)₄, PdCl₂(Ph₃P)₂ or PdCl₂ (dppf) and a base such as 2N Na₂CO₃ or K₂CO₃, in an organic solvent such as toluene, dioxane or THF, at a temperature in the range of about 80° C. to about 120° C., to yield the corresponding alkene (XVII).

Compounds of Formula (I) may be derived from ketone (XXIII). Ketone (XXIII) may be prepared according to the processes outlined in Scheme 6.

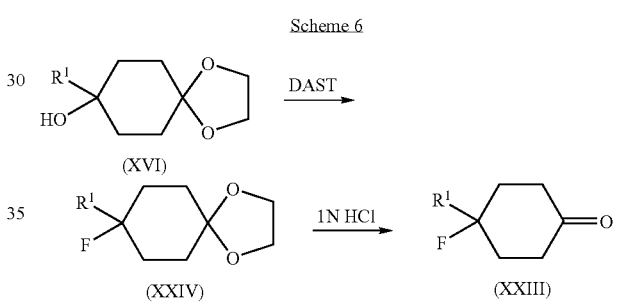

Ketal (XVI) is treated with a fluorinating agent such as DAST or trifluorosulfonyl fluoride, in an organic solvent such as dichloromethane, THF or dioxane, at a temperature in the range of about −78° C. to about 0° C., to yield the corresponding fluoride (XXIV). Fluoride (XXIV) is treated with an acid such as 1N HCl or 1N H₂SO₄, in an organic solvent such as acetone, acetonitrile or THF, at a temperature in the range of about 0° C. to about 25° C., to yield the corresponding ketone (XXIII).

Compounds of Formula (I) may be derived from ketone (XXV). Ketone (XXV) may be prepared according to the processes outlined in Scheme 7.

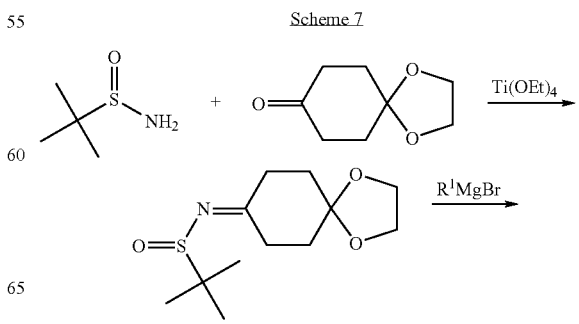

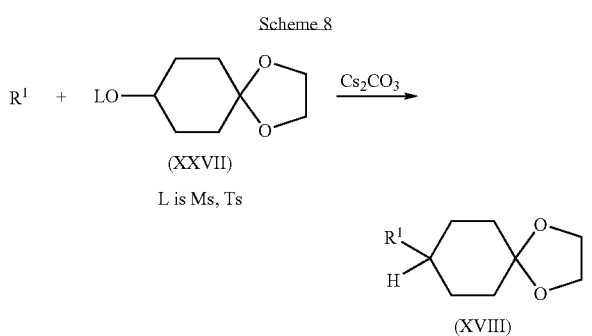

(XXVI)

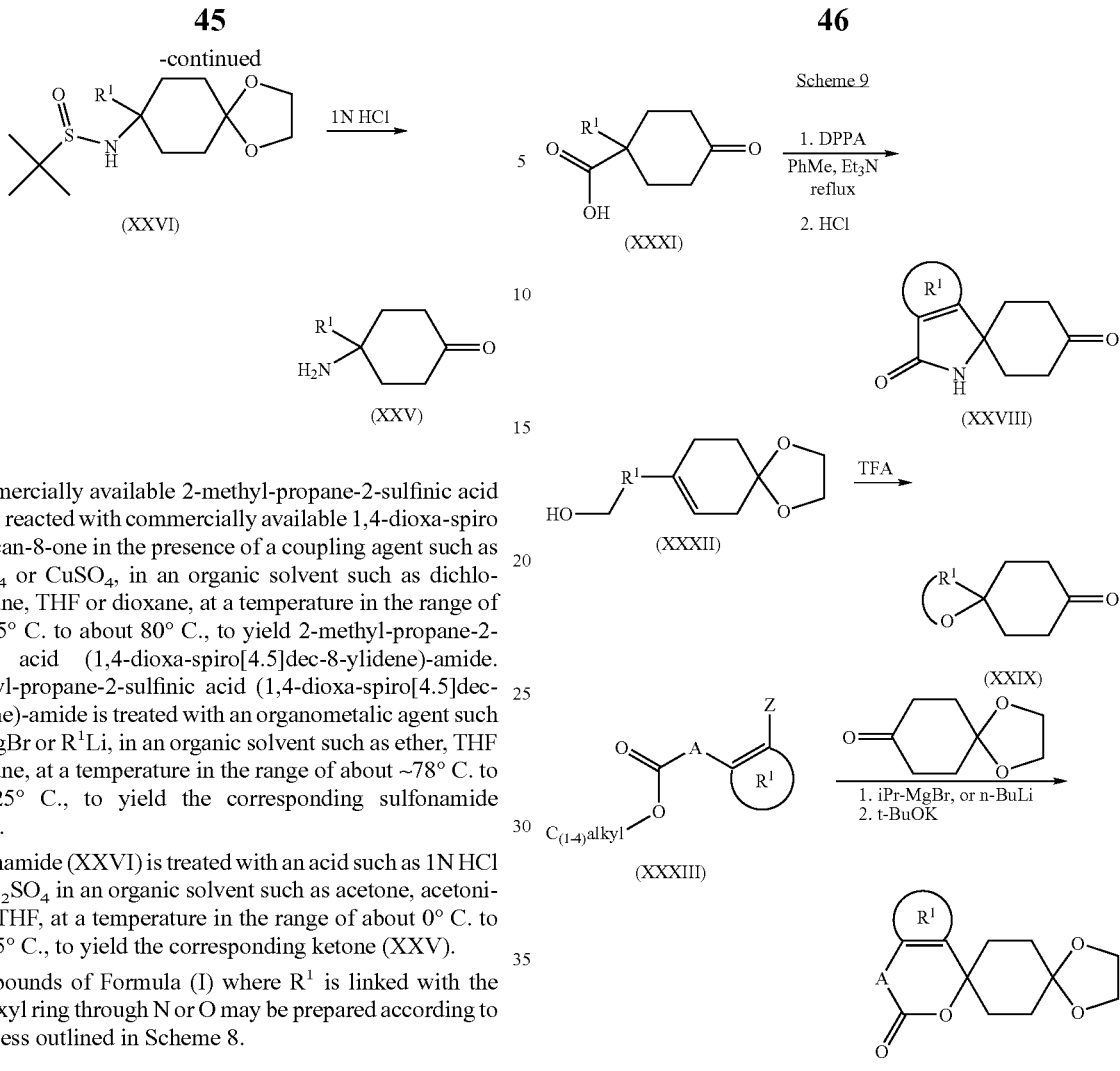

Commercially available 2-methyl-propane-2-sulfinic acid amide is reacted with commercially available 1,4-dioxa-spiro[4.5]decan-8-one in the presence of a coupling agent such as Ti(OEt)$_4$ or CuSO$_4$, in an organic solvent such as dichloromethane, THF or dioxane, at a temperature in the range of about 25° C. to about 80° C., to yield 2-methyl-propane-2-sulfinic acid (1,4-dioxa-spiro[4.5]dec-8-ylidene)-amide. 2-Methyl-propane-2-sulfinic acid (1,4-dioxa-spiro[4.5]dec-8-ylidene)-amide is treated with an organometalic agent such as R$^1$MgBr or R$^1$Li, in an organic solvent such as ether, THF or dioxane, at a temperature in the range of about −78° C. to about 25° C., to yield the corresponding sulfonamide (XXVI).

Sulfinamide (XXVI) is treated with an acid such as 1N HCl or 1N H$_2$SO$_4$ in an organic solvent such as acetone, acetonitrile or THF, at a temperature in the range of about 0° C. to about 25° C., to yield the corresponding ketone (XXV).

Compounds of Formula (I) where R$^1$ is linked with the cyclohexyl ring through N or O may be prepared according to the process outlined in Scheme 8.

Commercially available OH or NH substituted R$^1$ is reacted with alkyl tosylate or alkyl mesylate (XXVII) in the presence of inorganic base such as K$_2$CO$_3$, Cs$_2$CO$_3$ or NaH, in an organic solvent such as DMF or THF, at a temperature in the range of about 25° C. to about 80° C., to yield the corresponding ketal (XVIII).

Compounds of Formula (I) where R$^1$ and X form a five or six memebered ring may be prepared from compounds (XXVIII), (XXIX), or (XXX). Compounds of Formulae (XXVIII), (XXIX), and (XXX) where R$^1$ and X form a five or six memebered ring may be prepared according to the processes outlined in Scheme 9.

wherin:
A is a direct bond or N;
Z is Br or I;
DPPA is diphenylphosphorylazide

Spiro ketone (XXVIII) may be accessed by reacting a compound of Formula (XXXI), where R$^1$ is phenyl, substituted phenyl, heteroaryl, or substituted heteroaryl with diphenylphosphorylazide, a base such as triethylamine, in a solvent such as toluene, at elevated temperature, followed by treatment with an acid such as HCl.

In another approach, ketals of Formula (XXXII), where R$^1$ is aryl or heteroaryl substituted with CH$_2$OH, is treated with a strong acid such as concentrated TFA, HCl, 6N H$_2$SO$_4$ or methylsulfonic acid in an organic solvent such as dichloromethane or chloroform, at a temperature in the range of about 0° C. to about 25° C., to yield the corresponding ketone (XXXIX).

Finally, to access compounds of Formula XXX, aryl and heteroaryl halides with an ortho substituted ester or carbamic acid ester are reacted with commercially available 1,4-dioxa-spiro[4.5]decan-8-one and a metallating agent, such as n-butyl lithium, or isopropyl magnesium bromide, at a temperature of −78° C. to about 0° C., followed by treatment with a base, such as potassium tert-butoxide. Those skilled in the art will recognize that aryl and heteroaryl bromides are generally paired with n-butyl lithium, and added at temperatures closer to −78° C., whereas aryl and heteroaryl iodides are more commonly reacted with isopropyl magnesium bromide at temperatures closer to 0° C.

EXAMPLES

Representative compounds of the present invention can be synthesized in accordance with the general synthetic methods described herein. Compounds of Formula (I) can be prepared by methods known to those who are skilled in the art. The following examples are only meant to represent examples of the invention and are in no way meant to be a limit of the invention.

Example 1

N-({1-[4-(2-Oxo-2H-pyridin-1-yl)-cyclohexyl]-azetidin-3-ylcarbamoyl}-methyl)-3-trifluoromethyl-benzamide Step A: Toluene-4-sulfonic acid 1,4-dioxa-spiro[4.5]dec-8-yl ester

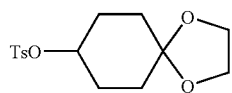

A solution of 1,4-dioxa-spiro[4.5]decan-8-ol (prepared according to the procedure of Kayser, Margaret M.; Clouthier, Christopher M. Journal of Organic Chemistry (2006), 71(22), 8424-8430, 11 g, 70 mmol) in DCM (100 mL) was treated with TEA (11 mL, 77 mmol) followed by TsCl (Aldrich, 13.3 g, 70 mmol) slowly at 0° C. The reaction was warmed to room temperature over 2 hours. The solution was partitioned between DCM and water. The organic layer was washed with brine, dried over anhydrous Na$_2$SO$_4$, filtered and concentrated to give white solid, which was then purified by silica gel column on a CombiFlash® system (Teledyne Isco, Inc, Lincoln, Neb.) system using hexanes and ethyl acetate (from 10% ethyl acetate to 100% ethyl acetate) to afford the title compound as white solid.

$^1$H NMR (400 MHz, CDCl$_3$) δ 7.80 (d, J=5.5 Hz, 2H), 7.28 (d, J=5.5 Hz, 2H), 4.61 (m, 1H), 3.90 (m, 4H), 1.85 (m, 6H), 1.55 (m, 2H).

Step B: 1-(1,4-Dioxa-spiro[4.5]dec-8-yl)-1H-pyridin-2-one and 2-(1,4-Dioxa-spiro[4.5]dec-8-yloxy)-pyridine

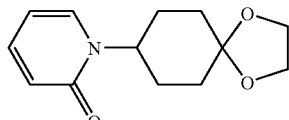

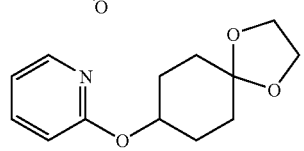

A solution of toluene-4-sulfonic acid 1,4-dioxa-spiro[4.5]dec-8-yl ester (as prepared in the previous step, 3.25 g, 10.3 mmol) and 1H-pyridin-2-one (Aldrich, 975 mg, 10.3 mmol) in DMF (10 mL) were heated at 80° C. in the presence of Cs$_2$CO$_3$ (Aldrich, 3.36 g, 10.3 mmol) for 3 hours and allowed to cool. The solid was filtered off and the solvent was removed in vacuo. The residue was partitioned between ethyl acetate and water. The organic layer was washed with brine, dried over anhydrous Na$_2$SO$_4$, filtered, concentrated then purified by silica gel column on a CombiFlash® system using hexanes and ethyl acetate (from 10% ethyl acetate to 100% ethyl acetate) to afford the title compounds as white solids, a less polar fraction 2-(1,4-dioxa-spiro[4.5]dec-8-yloxy)-pyridine, and a more polar fraction 1-(1,4-Dioxa-spiro[4.5]dec-8-yl)-1H-pyridin-2-one.

1-(1,4-Dioxa-spiro[4.5]dec-8-yl)-1H-pyridin-2-one
$^1$H NMR (400 MHz, CDCl$_3$) δ 7.48 (t, J=5.5 Hz, 1H), 7.29 (t, J=5.8 Hz, 1H), 6.57 (d, J=6.0 Hz, 1H), 6.20 (t, J=5.8 Hz, 1H), 4.99 (m, 1H), 4.01 (s, 4H), 1.90 (m, 8H). 2-(1,4-Dioxa-spiro[4.5]dec-8-yloxy)-pyridine
$^1$H NMR (400 MHz, CDCl$_3$) δ 8.11 (d, J=3.1 Hz, 1H), 7.55 (t, J=6.5 Hz, 2H), 6.80 (t, J=6.0 Hz, 1H), 6.69 (d, J=6.5 Hz, 1H), 5.20 (m, 1H), 3.95 (s, 4H), 2.01 (m, 6H), 1.75 (m, 2H).

Step C: 1-(4-Oxo-cyclohexyl)-1H-pyridin-2-one

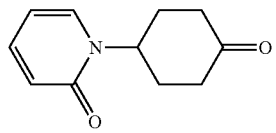

A solution of 1-(1,4-dioxa-spiro[4.5]dec-8-yl)-1H-pyridin-2-one (as prepared in the previous step, ~300 mg, 1.28 mmol)) in acetone (10 mL) was treated with 1N HCl (2 mL) at room temperature for 4 hours. The reaction was worked up with saturated sodium bicarbonate to adjust the pH to neutral. The solvent was removed in vacuo and residue partitioned between ethyl acetate and water. The organic layer was washed with brine, dried over anhydrous Na$_2$SO$_4$, filtered, concentrated to afford the title compound as white solid.

$^1$H NMR (400 MHz, CDCl$_3$) δ 7.35 (m, 2H), 6.60 (d, J=6.5 Hz, 1H), 6.20 (t, J=6.8 Hz, 1H), 5.41 (m, 1H), 2.65 (m, 2H), 2.55 (m, 2H), 2.30 (m, 2H), 2.01 (m, 2H).

Step D: N-({1-[4-(2-Oxo-2H-pyridin-1-yl)-cyclohexyl]-azetidin-3-ylcarbamoyl}-methyl)-3-trifluoromethyl-benzamide

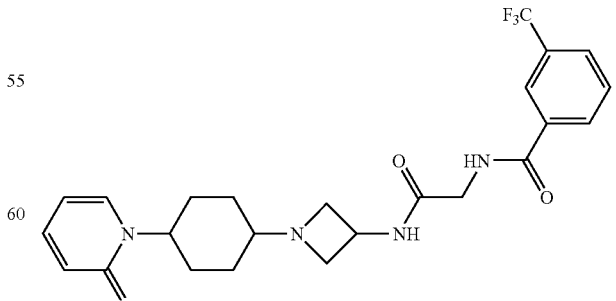

A solution of 1-(4-oxo-cyclohexyl)-1H-pyridin-2-one (as prepared in the previous step, 150 mg, 0.79 mmol) and N-(azetidin-3-ylcarbamoylmethyl)-3-trifluoromethyl-benzamide HCl salt (as prepared in Example 2 Step C, 400 mg, 1.18 mmol) in DCM (10 mL) was treated with TEA (340 μL, 2.40 mmol) for 10 min followed by NaBH(OAc)$_3$ (Aldrich, 510 mg, 2.40 mmol) for another 4 hours at room temperature. The reaction was quenched with saturated sodium bicarbonate. The organic layer was separated and the aqueous layer was extracted 3 times with a chloroform/IPA "cocktail" (~3:1, v/v). The combined organic layer was dried over anhydrous Na$_2$SO$_4$, filtered and concentrated to give the crude product, which was then purified by a CombiFlash® system using ethyl acetate and 7N NH$_3$ in MeOH as eluent (from pure ethyl acetate to 5% 7N NH$_3$ in MeOH in ethyl acetate) to afford two title compounds as white solids: a less polar isomer, and a more polar isomer.

1a: Less Polar Fraction from Silica Gel Column $^1$H NMR (400 MHz, d$_4$-MeOH) δ 8.25 (s, 1H), 8.20 (d, J=6.3 Hz, 1H), 7.88 (d, J=6.5 Hz, 1H), 7.86 (m, 1H), 7.72 (t, J=6.5 Hz, 1H), 7.46 (t, J=6.2 Hz, 1H), 6.52 (d, J=7.2 Hz, 1H), 6.42 (t, J=6.0 Hz, 1H), 4.95 (m, 1H), 4.45 (m, 1H), 4.15 (s, br, 2H), 4.08 (s, 2H), 3.68 (m, 2H), 3.02 (m, 1H), 2.10 (m, 4H), 1.90 (m, 2H), 1.72 (m, 2H).

1b: More Polar Fraction from Silica Gel Column $^1$H NMR (400 MHz, d$_4$-MeOH) δ 8.27 (s, 1H), 8.18 (d, J=6.5 Hz, 1H), 7.90 (d, J=6.5 Hz, 1H), 7.75 (t, J=6.2 Hz, 1H), 7.70 (d, J=6.5 Hz, 1H), 7.62 (t, J=6.5 Hz, 1H), 6.55 (d, J=7.5 Hz, 1H), 6.42 (t, J=5.6 Hz, 1H), 4.85 (m, 1H), 4.70 (m, 1H), 4.40 (t, J=6.0 Hz, 2H), 4.28 (t, J=6.0 Hz, 2H), 4.10 (s, 2H), 3.35 (m, 1H), 2.25 (m, 1H), 2.10 (m, 2H), 1.90 (m, 2H), 1.55 (m, 2H).

Example 2

N-({1-[4-(Pyridin-2-yloxy)-cyclohexyl]-azetidin-3-ylcarbamoyl}-methyl)-3-trifluoromethyl-benzamide Step A: 4-(Pyridin-2-yloxy)-cyclohexanone

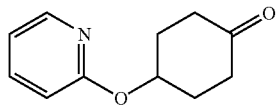

The title compound was prepared as a white solid from the de-protection of 2-(1,4-dioxa-spiro[4.5]dec-8-yloxy)-pyridine (as prepared in Example 1, Step B) using the procedure described in Step C of Example 1.

$^1$H NMR (400 MHz, CDCl$_3$) δ 8.15 (d, J=2.5 Hz, 1H), 7.60 (t, J=6.8 Hz, 1H), 6.90 (t, J=6.5 Hz, 1H), 6.75 (d, J=6.5 Hz, 1H), 5.45 (m, 1H), 2.68 (m, 2H), 2.41 (m, 2H), 2.30 (m, 2H), 2.20 (m, 2H).

Step B: 3-[2-(3-Trifluoromethyl-benzoylamino)-acetylamino]azetidine-1-carboxylic acid tert-butyl ester

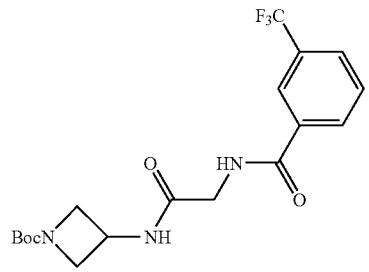

3-Amino-azetidine-1-carboxylic acid tert-butyl ester (AstaTech, 1.2 g, 6.97 mmol) and (3-trifluoromethyl-benzoylamino)-acetic acid (Bionet Building Blocks, 1.57 g, 6.36 mmol) were treated with EDCI (Aldrich, 1.57 g, 6.36 mmol), HOBT (Aldrich, 1.22 g, 6.36 mmol) in DCM (10 mL) at room temperature for 4 hours. The reaction solution was partitioned between DCM and water. The organic layer was washed with brine, dried over anhydrous Na$_2$SO$_4$, filtered and concentrated to give a yellow oil, and purified by silica gel column on a CombiFlash® system using hexanes and ethyl acetate (from 10% ethyl acetate to 100% ethyl acetate) to afford the title compound as a white solid.

$^1$H NMR (400 MHz, CDCl$_3$) δ 8.10 (s, 1H), 8.02 (d, J=6.6 Hz, 1H), 7.80 (d, J=6.8 Hz, 1H), 7.56 (t, J=6.5 Hz, 1H), 4.61 (m, 1H), 4.25 (t, J=7.2 Hz, 2H), 4.18 (d, J=5.5 Hz, 2H), 3.82 (t, J=7.5 Hz, 2H), 1.41 (s, 9H).

Step C: N-(Azetidin-3-ylcarbamoylmethyl)-3-trifluoromethyl-benzamide free base, HCl and TFA salt

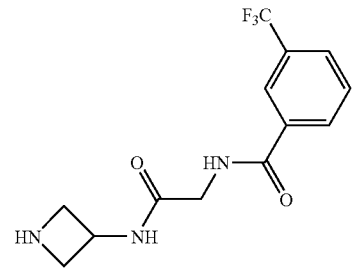

3-[2-(3-Trifluoromethyl-benzoylamino)-acetylamino]-azetidine-1-carboxylic acid tert-butyl ester (7.5 g, 18.7 mmol), as prepared in the previous step, was dissolved in 4N HCl in dioxane (5 mL) and MeOH (20 mL) at room temperature. The reaction was stirred for another 4 hours. The solvent was removed and the residue was dried to give the title compound as a HCl salt (yellow foam).

3-[2-(3-Trifluoromethyl-benzoylamino)-acetylamino]-azetidine-1-carboxylic acid tert-butyl ester (2.10 g, 5.24 mmol) was dissolved in 1:1 TFA and DCM mixed solution (10 mL) at room temperature. The reaction was stirred for another 2 hours. The solvent was removed and the residue was dried to give the title compound as a TFA salt containing extra TFA (colorless oil).

The free base was obtained by treating the salt in MeOH with solid Na$_2$CO$_3$ overnight. The solid was filtered and residue was dried to give the title compound for analytical characterization. The HCl or TFA salt was general used for the further reactions.

$^1$H NMR (400 MHz, CDCl$_3$) δ 8.10 (s, 1H), 8.05 (d, J=6.0 Hz, 1H), 7.78 (d, J=6.2 Hz, 1H), 7.55 (m, 2H), 4.78 (m, 1H), 4.15 (d, J=3.2 Hz, 2H), 3.95 (t, J=7.0 Hz, 2H), 3.52 (t, J=7.0 Hz, 2H).

Step D: N-({1-[4-(Pyridin-2-yloxy)-cyclohexyl]-azetidin-3-ylcarbamoyl}-methyl)-3-trifluoromethyl-benzamide

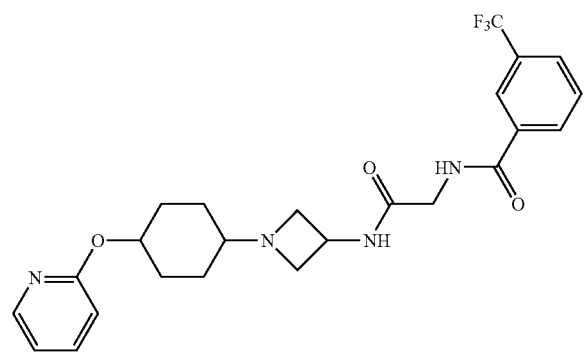

The title compounds were prepared as white solids from the reductive amination of 4-(pyridin-2-yloxy)-cyclohexanone (as prepared in Step A) and N-(azetidin-3-ylcarbamoylmethyl)-3-trifluoromethyl-benzamide (as prepared in the previous step) using the procedure described in Step D of Example 1.

2a: Less Polar Fraction from Silica Gel Column, $^1$H NMR (400 MHz, d$_4$-MeOH) δ 8.25 (s, 1H), 8.15 (d, J=6.3 Hz, 1H), 8.10 (d, J=4.3 Hz, 1H), 7.88 (d, J=6.5 Hz, 1H), 7.70 (t, J=5.6 Hz, 1H), 7.65 (t, J=6.5 Hz, 1H), 6.90 (d, J=6.2 Hz, 1H), 6.74 (t, J=7.0 Hz, 1H), 5.18 (s, 1H), 4.45 (m, 1H), 4.05 (s, 2H), 3.62 (t, J=7.0 Hz, 2H), 3.02 (t, J=7.0 Hz, 2H), 2.25 (s, br, 1H), 2.05 (m, 2H), 1.70 (m, 2H), 1.62 (m, 2H), 1.50 (m, 2H).

2b: More Polar Fraction from Silica Gel Column $^1$H NMR (400 MHz, d$_4$-MeOH) δ 8.28 (s, 1H), 8.18 (d, J=6.5 Hz, 1H), 8.10 9d, J=4.5 Hz, 1H), 7.90 (d, J=6.5 Hz, 1H), 7.72 (t, J=6.0 Hz, 1H), 7.66 (t, J=6.5 Hz, 1H), 6.91 (t, J=6.6 Hz, 1H), 6.75 (t, J=7.0 Hz, 1H0, 5.18 (m, 1H), 4.50 (m, 1H), 4.08 (s, 2H), 4.68 (t, J=7.0 Hz, 2H), 3.70 (t, J=7.2 Hz, 2H), 3.07 (t, J=7.0 Hz, 2H), 2.25 (m, 1H), 1.96 (m, 2H), 1.75 (m, 2H), 1.42 (m, 2H), 1.25 (m, 2H).

Example 3

N-({1-[4-(5-Bromo-2-oxo-2H-pyrimidin-1-yl)-cyclohexyl]-azetidin-3-ylcarbamoyl}-methyl)-3-trifluoromethyl-benzamide Step A: 5-Bromo-1-(1,4-dioxa-spiro[4.5]dec-8-yl)-1H-pyrimidin-2-one and 5-Bromo-2-(1,4-dioxa-spiro[4.5]dec-8-yloxy)-pyrimidine

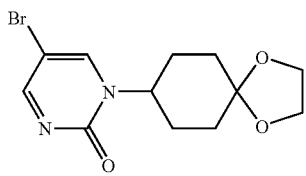

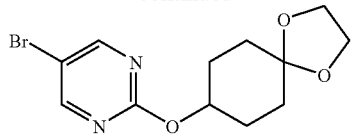

The title compounds were prepared as white solids from 5-bromo-1H-pyrimidin-2-one (Aldrich) using the procedure described in Step B of Example 1.

5-Bromo-1-(1,4-dioxa-spiro[4.5]dec-8-yl)-1H-pyrimidin-2-one $^1$H NMR (400 MHz, CDCl$_3$) δ 7.65 (s, 1H), 7.33 (s, 1H), 1.90 (m, 6H), 1.67 (m, 2H). 5-Bromo-2-(1,4-dioxa-spiro[4.5]dec-8-yloxy)-pyrimidine $^1$H NMR (400 MHz, CDCl$_3$) δ 8.55 (s, 2H), 5.30 (m, 1H), 2.05 (m, 4H), 1.90 (m, 2H), 1.72 (m, 2H).

Step B: 5-Bromo-1-(4-oxo-cyclohexyl)-1H-pyrimidin-2-one

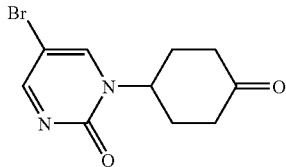

The title compound was prepared as a white solid from the de-protection of 5-bromo-1-(1,4-dioxa-spiro[4.5]dec-8-yl)-1H-pyrimidin-2-one (as prepared in the previous step) using the procedure described in Step C of Example 1.

ESI-MS (m/z): Calcd. For C$_{10}$H$_{11}$BrN$_2$O$_2$, 271; found: 272 (M+H).

Step C: N-({1-[4-(5-Bromo-2-oxo-2H-pyrimidin-1-yl)-cyclohexyl]-azetidin-3-ylcarbamoyl}-methyl)-3-trifluoromethyl-benzamide

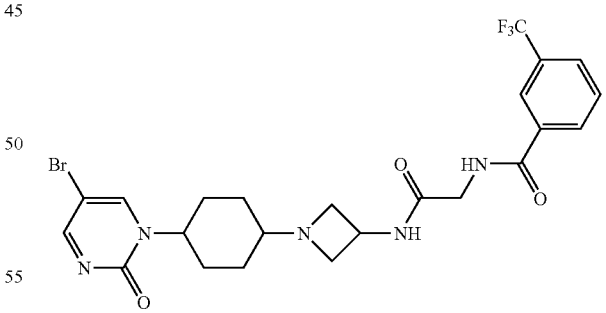

The title compounds were prepared as white solids from the reductive amination of 5-bromo-1-(4-oxo-cyclohexyl)-1H-pyrimidin-2-one (as prepared in the previous step) and N-(azetidin-3-ylcarbamoylmethyl)-3-trifluoromethyl-benzamide (as prepared in Example 2 Step C) using the procedure described in Step D of Example 1.

$^1$H NMR (400 MHz, d$_4$-MeOH) δ 8.15 (s, 1H), 8.05 (d, J=6.3 Hz, 1H), 7.78 (d, J=6.5 Hz, 1H), 7.71 (s, 1H), 7.59 (t, J=6.5 Hz, 1H), 7.36 (s, 1H), 5.05 (m, 1H), 4.35 (m, 1H), 3.92

(s, 2H), 3.54 (m, J=7.0 Hz, 2H), 2.96 (m, J=7.0 Hz, 2H), 2.15 (m, 1H), 2.05 (m, 1H), 1.80 (m, 1H), 1.52 (m, 2H), 1.40 (m, 2H), 1.10 (m, 2H).

Example 4

N-({1-[4-(2-Oxo-2H-pyrimidin-1-yl)-cyclohexyl]-azetidin-3-ylcarbamoyl}-methyl)-3-trifluoromethyl-benzamide

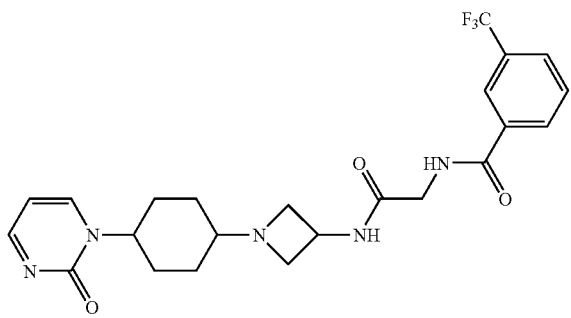

N-({1-[4-(5-Bromo-2-oxo-2H-pyrimidin-1-yl)-cyclohexyl]-azetidin-3-ylcarbamoyl}-methyl)-3-trifluoromethyl-benzamide (as prepared in Example 3, Step C, ~150 mg, 0.27 mmol) in MeOH (20 mL) was driven through H-Cube® Continuous-flow Hydrogenation reactor (ThalesNano, Budapest, Hungary) under full hydrogen mode at room temperature using 10% Pd/C cartridge. The resulting solution was concentrated and purified by silica gel column on a CombiFlash® system using ethyl acetate and 7N $NH_3$ in MeOH as eluent (from pure ethyl acetate to 5% 7N $NH_3$ in MeOH in ethyl acetate) to afford the title compound as white solid.

ESI-MS (m/z): Calcd. For $C_{23}H_{26}F_3N_5O_3$, 477; found: 478 (M+H).

Example 5

N-({1-[4-(5-Bromo-pyrimidin-2-yloxy)-cyclohexyl]-azetidin-3-ylcarbamoyl}-methyl)-3-trifluoromethyl-benzamide Step A:
4-(5-Bromo-pyrimidin-2-yloxy)-cyclohexanone

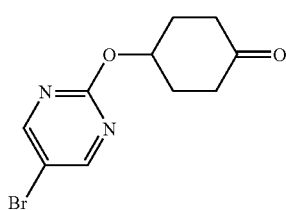

The title compound was prepared as a white solid from the de-protection of 5-bromo-2-(1,4-dioxa-spiro[4.5]dec-8-yloxy)-pyrimidine (as prepared in Example 3, Step A) using the procedure described in Step C of Example 1.

$^1$H NMR (400 MHz, CDCl$_3$) δ 8.52 (s, 2H), 5.38 (m 1H), 2.70 (m, 2H), 2.45 (m, 2H), 2.33 (m, 2H), 2.20 (m, 2H).

Step B: N-({1-[4-(5-Bromo-pyrimidin-2-yloxy)-cyclohexyl]-azetidin-3-ylcarbamoyl}-methyl)-3-trifluoromethyl-benzamide

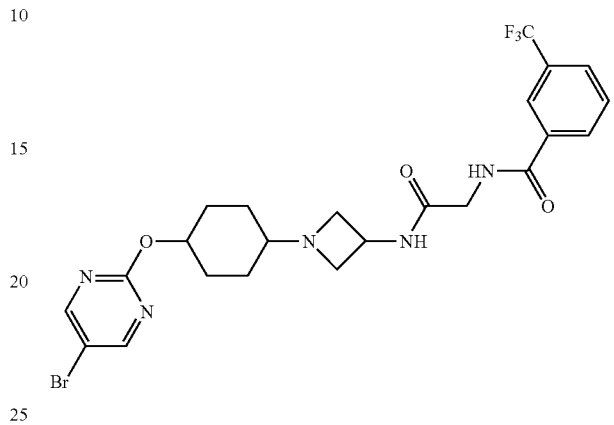

The title compounds were prepared as white solids from the reductive amination of 4-(5-bromo-pyrimidin-2-yloxy)-cyclohexanone (as prepared in the previous step) and N-(azetidin-3-ylcarbamoylmethyl)-3-trifluoromethyl-benzamide (as prepared in Example 2 Step C) using the procedure described in Step D of Example 1.

5a: Less Polar Fraction from Silica Gel Column $^1$H NMR (400 MHz, d$_4$-MeOH) δ 8.45 (s, 2H), 8.15 (s, 1H), 8.05 (d, J=6.3 Hz, 1H), 7.72 (d, J=6.5 Hz, 1H), 7.55 (t, J=6.5 Hz, 1H), 5.05 (m, 1H), 4.35 (m, 1H), 3.92 (s, 2H), 3.54 (m, J=7.0 Hz, 2H), 2.96 (m, J=7.0 Hz, 2H), 2.15 (m, 1H), 2.05 (m, 1H), 1.80 (m, 1H), 1.52 (m, 2H), 1.40 (m, 2H), 1.10 (m, 2H).

5b: More Polar Fraction from Silica Gel Column $^1$H NMR (400 MHz, d$_4$-MeOH) δ 8.58 (s, 1H), 8.20 (s, 1H), 8.06 (d, J=6.5 Hz, 1H), 7.77 (d, J=6.5 Hz, 1H), 7.60 (t, J=6.5 Hz, 1H), 5.10 (m, 1H), 4.36 (m, 1H), 4.05 (s, 2H), 3.68 (t, J=7.0 Hz, 2H), 3.05 (t, J=7.2 Hz, 2H), 2.20 (m, 1H), 2.10 (m, 2H), 1.70 (m, 4H), 1.55 (m, 2H).

Example 6

N-({1-[4-(6-Oxo-6H-pyrimidin-1-yl)-cyclohexyl]-azetidin-3-ylcarbamoyl}-methyl)-3-trifluoromethyl-benzamide Step A: 3-(1,4-Dioxa-spiro[4.5]dec-8-yl)-3H-pyrimidin-4-one and 4-(1,4-Dioxa-spiro[4.5]dec-8-yloxy)-pyrimidine

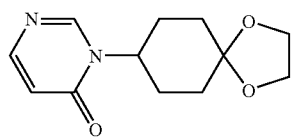

-continued

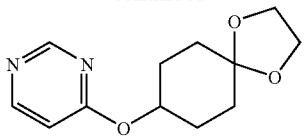

The title compounds were prepared as white solids from 3H-pyrimidin-4-one (Aldrich) using the procedure described in Step B of Example 1.
3-(1,4-Dioxa-spiro[4.5]dec-8-yl)-3H-pyrimidin-4-one
ESI-MS (m/z): Calcd. For $C_{12}H_{16}N_2O_3$, 236; found: 237 (M+H).
4-(1,4-Dioxa-spiro[4.5]dec-8-yloxy)-pyrimidine
ESI-MS (m/z): Calcd. For $C_{12}H_{16}N_2O_3$, 236; found: 237 (M+H).

Step B: 3-(4-Oxo-cyclohexyl)-3H-pyrimidin-4-one

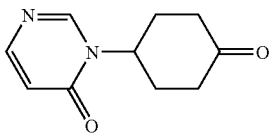

The title compound was prepared as a white solid from the de-protection of 3-(1,4-dioxa-spiro[4.5]dec-8-yl)-3H-pyrimidin-4-one (as prepared in the previous step) using the procedure described in Step C of Example 1.
$^1$H NMR (400 MHz, CDCl$_3$) δ 8.15 (s, 1H), 7.90 (d, J=6.0 Hz, 1H), 6.45 (d, J=6.6 Hz, 1H), 5.21 (m, 1H), 2.60 (m, 4H), 2.31 (m, 2H), 2.11 (m, 2H).

Step C: N-({1-[4-(6-Oxo-6H-pyrimidin-1-yl)-cyclohexyl]-azetidin-3-ylcarbamoyl}-methyl)-3-trifluoromethyl-benzamide

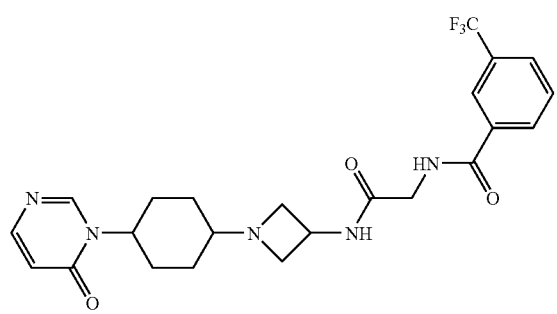

The title compounds were prepared as white solids from the reductive amination of 3-(4-oxo-cyclohexyl)-3H-pyrimidin-4-one (as prepared in the previous step) and N-(azetidin-3-ylcarbamoylmethyl)-3-trifluoromethyl-benzamide (as prepared in Example 2 Step C) using the procedure described in Step D of Example 1.
6a: Less Polar Fraction from Silica Gel Column
$^1$H NMR (400 MHz, d$_4$-MeOH) δ 8.45 (s, 1H), 8.22 (s, 1H), 8.18 (d, J=6.3 Hz, 1H), 7.92 (d, J=4.5 Hz, 1H), 7.85 (d, J=6.5 Hz, 1H), 7.66 (t, J=6.5 Hz, 1H), 6.48 (d, J=5.6 Hz, 1H), 4.55 (m, 1H), 4.48 (m, 1H), 4.05 (s, 2H), 3.76 (t, J=7.0 Hz, 2H), 3.12 (t, J=7.0 Hz, 2H), 2.35 (s, br, 1H), 2.10 (m, 2H), 1.90 (m, 4H), 1.30 (m, 2H).

6b: More Polar Fraction from Silica Gel Column
$^1$H NMR (400 MHz, d$_4$-MeOH) δ 8.50 (s, 1H), 8.25 (s, 1H), 8.20 (d, J=6.0 Hz, 1H), 7.94 (d, J=5.0 Hz, 1H), 7.88 (d, J=6.5 Hz, 1H), 7.72 (t, J=6.5 Hz, 1H), 6.45 (d, J=6.2 Hz, 1H), 4.60 (m, 1H), 4.45 (m, 1H), 4.09 (s, 2H), 4.68 (t, J=7.0 Hz, 2H), 3.75 (t, J=6.5 Hz, 2H), 3.02 (t, J=7.0 Hz, 2H), 2.30 (m, 1H), 2.20 (m, 2H), 1.85 (m, 2H), 1.54 (m, 2H), 1.20 (m, 2H).

Example 7

N-({1-[4-(Pyrimidin-4-yloxy)-cyclohexyl]-azetidin-3-ylcarbamoyl}-methyl)-3-trifluoromethyl-benzamide Step A: 4-(Pyrimidin-4-yloxy)-cyclohexanone

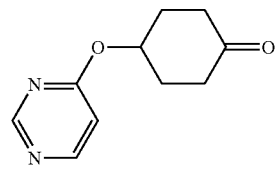

The title compound was prepared as a white solid from the de-protection of 4-(1,4-dioxa-spiro[4.5]dec-8-yloxy)-pyrimidine (as prepared in Example 6, Step A) using the procedure described in Step C of Example 1.
ESI-MS (m/z): Calcd. For $C_{10}H_{12}N_2O_2$, 192; found: 193 (M+H).

Step B: N-({1-[4-(Pyrimidin-4-yloxy)-cyclohexyl]-azetidin-3-ylcarbamoyl}-methyl)-3-trifluoromethyl-benzamide

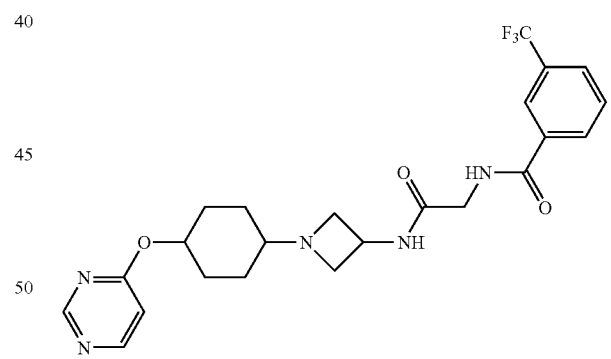

The title compounds were prepared as white solids from the reductive amination of 4-(pyrimidin-4-yloxy)-cyclohexanone (as prepared in the previous step) and N-(azetidin-3-ylcarbamoylmethyl)-3-trifluoromethyl-benzamide (as prepared in Example 2 Step C) using the procedure described in Step D of Example 1.
7a: Less Polar Fraction from Silica Gel Column
$^1$H NMR (400 MHz, d$_4$-MeOH) δ 8.55 (s, 1H), 8.38 (t, J=5.1 Hz, 1H), 8.11 (s, 1H), 8.04 (d, J=6.0 Hz, 1H), 7.75 (d, J=6.0 Hz, 1H), 7.58 (t, J=6.5 Hz, 1H), 6.72 (d, J=6.5 Hz, 1H), 5.25 (m, 1H), 4.62 (m, 1H), 4.30 (m, J=6.0 Hz, 2H), 4.15 (t, J=6.0 Hz, 2H), 3.98 (s, 2H), 2.25 (m, 1H), 2.20 (m, 2H), 2.02 (m, 2H), 1.85 (m, 2H), 1.60 (m, 2H).

7b: More Polar Fraction

ESI-MS (m/z): Calcd. For $C_{23}H_{26}F_3N_5O_3$, 477; found: 478 (M+H).

Example 8

N-({1-[4-(5-Iodo-2-oxo-2H-pyridin-1-yl)-cyclohexyl]-azetidin-3-ylcarbamoyl}-methyl)-3-trifluoromethyl-benzamide Step A: 1-(1,4-Dioxa-spiro[4.5]dec-8-yl)-5-iodo-1H-pyridin-2-one

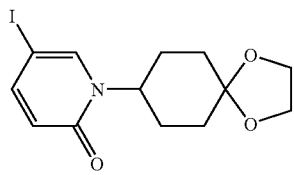

The title compound was prepared as white solids from 5-iodo-1H-pyridin-2-one (Aldrich) using the procedure described in Step B of Example 1.

$^1$H NMR (400 MHz, CDCl$_3$) δ 8.05 (s, 1H), 7.78 (d, J=6.0 Hz, 1H), 7.35 (d, J=6.0 Hz, 1H), 4.95 (m, 1H), 4.51 (m, 1H), 3.98 (m, 4H), 1.98 (m, 4H), 1.80 (m, 4H).

Step B: 5-Iodo-1-(4-oxo-cyclohexyl)-1H-pyridin-2-one

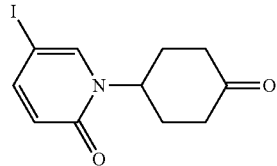

The title compound was prepared as a white solid from the de-protection of 1-(1,4-dioxa-spiro[4.5]dec-8-yl)-5-iodo-1H-pyridin-2-one (as prepared in the previous step) using the procedure described in Step C of Example 1.

$^1$H NMR (400 MHz, CDCl$_3$) δ 8.05 (s, 1H), 7.82 (d, J=6.5 Hz, 1H), 7.43 (d, J=6.0 Hz, 1H), 4.98 (m, 1H), 4.51 (m, 1H), 2.56 (m, 2H), 2.30 (m, 2H), 2.10 (m, 2H), 1.94 (m, 2H).

Step C: N-({1-[4-(5-Iodo-2-oxo-2H-pyridin-1-yl)-cyclohexyl]-azetidin-3-ylcarbamoyl}-methyl)-3-trifluoromethyl-benzamide

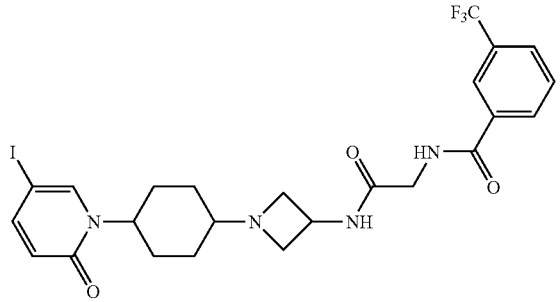

The title compounds were prepared as white solids from the reductive amination of 5-iodo-1-(4-oxo-cyclohexyl)-1H-pyridin-2-one (as prepared in the previous step) and N-(azetidin-3-ylcarbamoylmethyl)-3-trifluoromethyl-benzamide (as prepared in Example 2 Step C) using the procedure described in Step D of Example 1.

8a: Less Polar Fraction from Silica Gel Column $^1$H NMR (400 MHz, d$_4$-MeOH) δ 8.18 (s, 1H), 8.08 (d, J=6.1 Hz, 1H), 7.91 (d, J=6.0 Hz, 1H), 7.75 (m, 1H), 7.58 (t, J=6.5 Hz, 1H), 7.48 (m, 1H), 6.32 (d, J=6.5 Hz, 1H), 4.82 (m, 1H), 4.60 (m, 1H), 4.15 (s, 2H), 4.10 (t, J=6.0 Hz, 2H), 3.50 (t, J=6.0 Hz, 2H), 2.90 (m, 1H), 2.02 (m, 4H), 1.75 (m, 4H).

8b: More Polar Fraction from Silica Gel Column $^1$H NMR (400 MHz, d$_4$-MeOH) δ 8.15 (s, 1H), 8.05 (d, J=6.0 Hz, 1H), 7.78 (m, 2H), 7.60 (t, J=6.0 Hz, 1H), 7.50 (d, J=6.5 Hz, 1H), 6.28 (d, J=6.8 Hz, 2H), 4.62 (m, 1H), 4.51 (m, 1H), 4.05 (t, J=6.8 Hz, 2H), 3.98 (s, 2H), 3.55 (t, J=6.5 Hz, 2H), 2.75 (m, 1H), 2.00 (m, 2H), 1.90 (m, 2H), 1.75 (m, 2H), 1.35 (m, 2H).

Example 9

N-({1-[4-(5-Ethynyl-2-oxo-2H-pyridin-1-yl)-cyclohexyl]-azetidin-3-ylcarbamoyl}-methyl)-3-trifluoromethyl-benzamide

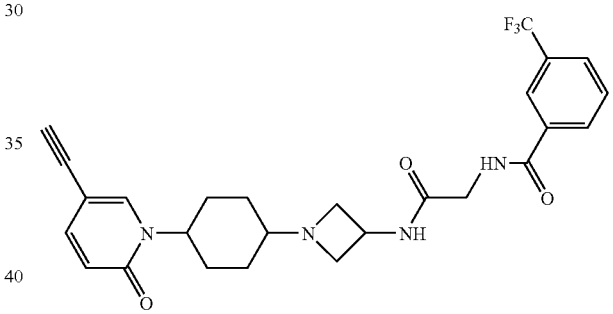

N-({1-[4-(5-Iodo-2-oxo-2H-pyridin-1-yl)-cyclohexyl]-azetidin-3-ylcarbamoyl}-methyl)-3-trifluoromethyl-benzamide (as prepared in Example 8, Step C, 450 mg, 0.75 mmol), ethynyl-trimethyl-silane (Fluka, 100 mg, 1.02 mmol), Pd(Ph$_3$P)$_2$Cl$_2$ (Aldrich, 0.02 mmol), CuI (Aldrich, 0.02 mmol) and TEA (1 mL) were mixed in THF (6 mL) at room temperature under argon. The reaction was stirred overnight. The solid was filtered off and the residue was partitioned between water and a chloroform/IPA "cocktail" (~3:1, v/v). The organic layer was dried over anhydrous Na$_2$SO$_4$, filtered and concentrated to give the crude product, which was treated with TBAF (Aldrich, 1.0 N in THF, 2 mL) for 30 min. at room temperature. The solvent was removed and the residue was then purified by a CombiFlash® system using ethyl acetate and 7N NH$_3$ in MeOH as eluent (from pure ethyl acetate to 5% 7N NH$_3$ in MeOH in ethyl acetate) to afford the title compound as yellow solid.

$^1$H NMR (400 MHz, CDCl$_3$) δ 8.15 (s, 1H), 8.04 (d, J=5.6 Hz, 1H), 7.78 (d, J=5.8 Hz, 1H), 7.65 (t, J=6.0 Hz, 1H), 7.35 (m, 1H), 7.30 (d, J=6.5 Hz, 1H), 6.90 (m, 1H), 6.45 (d, J=6.5 Hz, 1H), 4.82 (m, 1H), 4.50 (m, 1H), 4.18 (d, J=4.2 Hz, 2H), 3.95 (m, 1H), 3.65 (t, J=7.0 Hz, 2H), 2.90 (d, J=6.5 Hz, 2H), 2.35 (m, 1H), 1.95 (m, 4H), 1.60 (m, 4H).

Example 10

N-({1-[4-(5-Cyano-2-oxo-2H-pyridin-1-yl)-cyclohexyl]-azetidin-3-ylcarbamoyl}-methyl)-3-trifluoromethyl-benzamide

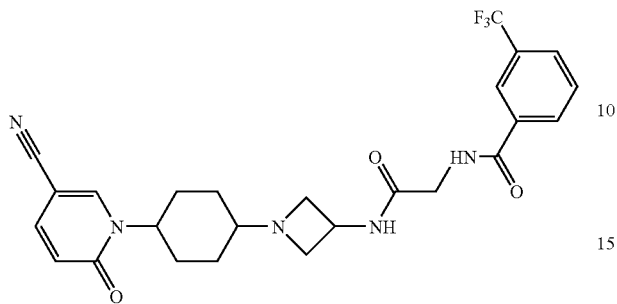

A solution of N-({1-[4-(5-iodo-2-oxo-2H-pyridin-1-yl)-cyclohexyl]-azetidin-3-ylcarbamoyl}-methyl)-3-trifluoromethyl-benzamide (as prepared in Example 8, Step C, 300 mg, 0.5 mmol), CuCN (Aldrich, 1 mmol), DMF (4 mL) in a sealed tube was irradiated under microwave at 180° C. for 30 min. The solid was filtered off and the residue was partitioned between water and a chloroform/IPA "cocktail" (~3:1, v/v). The organic layer was dried over anhydrous $Na_2SO_4$, filtered and concentrated to give the crude product, which was then purified by a CombiFlash® system using ethyl acetate and 7N $NH_3$ in MeOH as eluent (from pure ethyl acetate to 5% 7N $NH_3$ in MeOH in ethyl acetate) to afford the title compound as yellow solid.

$^1$H NMR (400 MHz, $d_4$-MeOH) δ 8.22 (s, 1H), 8.10 (s, 1H), 8.08 (d, J=6.1 Hz, 1H), 7.81 (d, J=6.0 Hz, 1H), 7.65 (t, J=6.5 Hz, 1H), 7.42 (dd, J=6.5, 4.5 Hz, 1H), 6.42 (dd, J=6.5, 4.5 Hz, 1H), 4.62 (m, 1H), 4.35 (m, 1H), 3.95 (s, 2H), 4.10 (t, J=6.0 Hz, 2H), 3.62 (m, 2H), 3.05 (m, 2H), 2.20 (m, 1H), 1.96 (m, 2H), 1.80 (m, 2H), 1.65 (m, 2H), 1.20 (m, 2H).

Example 11

N-({1-[4-(5-Methyl-2-oxo-2H-pyridin-1-yl)-cyclohexyl]-azetidin-3-ylcarbamoyl}-methyl)-3-trifluoromethyl-benzamide Step A: 1-(1,4-Dioxa-spiro[4.5]dec-8-yl)-5-methyl-1H-pyridin-2-one and 2-(1,4-Dioxa-spiro[4.5]dec-8-yloxy)-5-methyl-pyridine

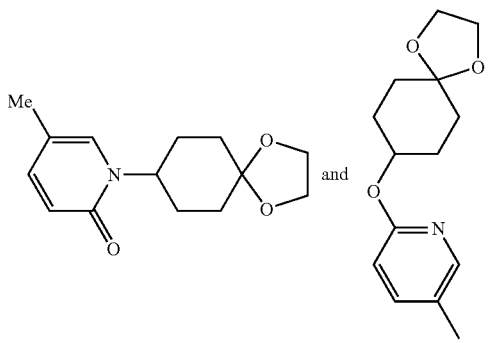

The title compounds were prepared as white solids from 5-methyl-1H-pyridin-2-one (Aldrich) using the procedure described in Step B of Example 1.

1-(1,4-Dioxa-spiro[4.5]dec-8-yl)-5-methyl-1H-pyridin-2-one

ESI-MS (m/z): Calcd. For $C_{14}H_{19}NO_3$, 249; found: 250 (M+H).

2-(1,4-Dioxa-spiro[4.5]dec-8-yloxy)-5-methyl-pyridine

ESI-MS (m/z): Calcd. For $C_{14}H_{19}NO_3$: 249; found: 250 (M+H).

Step B: 5-Methyl-1-(4-oxo-cyclohexyl)-1H-pyridin-2-one

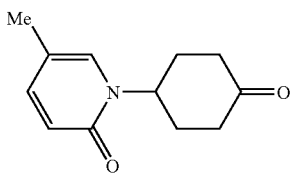

The title compound was prepared as a white solid from the de-protection of 1-(1,4-dioxa-spiro[4.5]dec-8-yl)-5-methyl-1H-pyridin-2-one (as prepared in the previous step) using the procedure described in Step C of Example 1.

$^1$H NMR (400 MHz, $CDCl_3$) δ 7.58 (d, J=6.2 Hz, 1H), 6.40 (s, 1H), 6.35 (d, J=6.2 Hz, 1H), 5.25 (m, 1H), 3.33 (m, 1H), 2.70 (m, 2H), 2.55 (m, 2H), 2.25 (s, 3H), 2.15 (m, 4H).

Step C: N-({1-[4-(5-Methyl-2-oxo-2H-pyridin-1-yl)-cyclohexyl]-azetidin-3-ylcarbamoyl}-methyl)-3-trifluoromethyl-benzamide

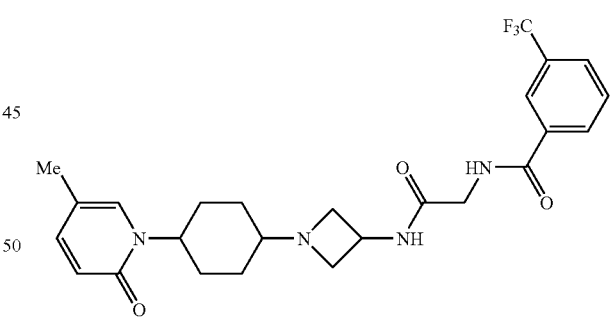

The title compounds were prepared as white solids from the reductive amination of 5-methyl-1-(4-oxo-cyclohexyl)-1H-pyridin-2-one (as prepared in the previous step) and N-(azetidin-3-ylcarbamoylmethyl)-3-trifluoromethyl-benzamide (as prepared in Example 2 Step C) using the procedure described in Step D of Example 1.

$^1$H NMR (400 MHz, $d_4$-MeOH) δ 8.25 (s, 1H), 8.20 (d, J=6.5 Hz, 1H), 7.88 (d, J=6.6 Hz, 1H), 7.75 (t, J=6.4 Hz, 1H), 7.55 (d, J=6.0 Hz, 1H), 6.35 (s, 1H), 6.32 (d, J=5.0 Hz, 1H), 4.98 (m, 1H), 4.80 (m, 1H), 4.52 (t, J=6.0 Hz, 2H), 4.38 (m, 2H), 4.01 (s, 2H), 2.28 (s, 3H), 2.25 (m, 2H), 2.05 (m, 2H), 1.85 (m, 2H), 1.50 (m, 2H).

Example 12

N-({1-[4-(5-Methyl-pyridin-2-yloxy)-cyclohexyl]-azetidin-3-ylcarbamoyl}-methyl)-3-trifluoromethyl-benzamide Step A: 4-(5-Methyl-pyridin-2-yloxy)-cyclohexanone

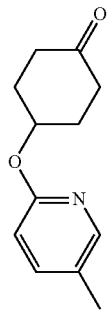

The title compound was prepared as a white solid from the de-protection of 2-(1,4-dioxa-spiro[4.5]dec-8-yloxy)-5-methyl-pyridine (as prepared in Example 11, Step A) using the procedure described in Step C of Example 1.

ESI-MS (m/z): Calcd. For $C_{12}H_{15}NO_2$: 205.11; found: 206.6 (M+H).

Step B: N-({1-[4-(5-Methyl-pyridin-2-yloxy)-cyclohexyl]-azetidin-3-ylcarbamoyl}-methyl)-3-trifluoromethyl-benzamide

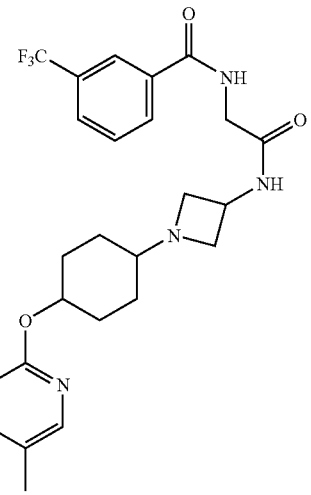

The title compounds were prepared as white solids from the reductive amination of 4-(5-methyl-pyridin-2-yloxy)-cyclohexanone (as prepared in the previous step) and N-(azetidin-3-ylcarbamoylmethyl)-3-trifluoromethyl-benzamide (as prepared in Example 2 Step C) using the procedure described in Step D of Example 1.

12a: Less Polar Isomer from Silica Gel Column,
$^1$H NMR (CHLOROFORM-d) δ: 8.12 (s, 1H), 8.02 (d, J=7.8 Hz, 1H), 7.92 (s, 1H), 7.78 (d, J=7.8 Hz, 1H), 7.39-7.49 (m, 1H), 7.06 (d, J=7.1 Hz, 1H), 6.59 (d, J=8.3 Hz, 1H), 5.06-5.22 (m, 1H), 4.55 (d, J=6.6 Hz, 1H), 4.18 (d, J=4.8 Hz, 2H), 3.63 (t, J=7.5 Hz, 2H), 2.84 (br s., 2H), 2.51 (br s, 1H), 2.22 (s, 3H), 1.95-2.05 (m, 2H), 1.41-1.64 (m, 6H).

12b: Less Polar Isomer from Silica Gel Column
$^1$H NMR (CHLOROFORM-d) δ: 8.10 (s, 1H), 7.99 (d, J=9.6 Hz, 1H), 7.93 (d, J=2.5 Hz, 1H), 7.79 (d, J=8.1 Hz, 1H), 7.60 (t, J=7.7 Hz, 1H), 7.34-7.41 (m, 1H), 6.97 (br. s., 1H), 6.58 (d, J=8.6 Hz, 1H), 6.31 (t, J=6.4 Hz, 1H), 4.81-4.98 (m, 1H), 4.41-4.66 (m, 1H), 4.13 (s, 2H), 3.63 (t, J=7.5 Hz, 2H), 2.89-3.10 (m, 2H), 2.51 (s, 1H), 2.22 (s, 3H), 2.14 (d, J=13.1 Hz, 2H), 1.81 (d, J=14.7 Hz, 2H), 1.57 (br. s., 2H), 1.36-1.49 (m, 2H).

Example 13

N-({1-[4-(3-Methoxy-2-oxo-2H-pyridin-1-yl)-cyclohexyl]-azetidin-3-ylcarbamoyl}-methyl)-3-trifluoromethyl-benzamide Step A: 1-(1,4-Dioxa-spiro[4.5]dec-8-yl)-3-methoxy-1H-pyridin-2-one and 2-(1,4-Dioxa-spiro[4.5]dec-8-yloxy)-3-methoxy-pyridine

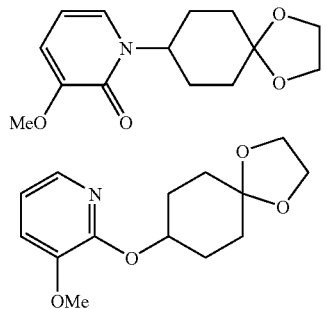

The title compounds were prepared as white solids from 3-methoxy-1H-pyridin-2-one (Aldrich) using the procedure described in Step B of Example 1.

1-(1,4-Dioxa-spiro[4.5]dec-8-yl)-3-methoxy-1H-pyridin-2-one:
$^1$H NMR (400 MHz, CDCl$_3$) δ 7.01 (d, J=5.6 Hz, 1H), 6.56 (d, J=5.8 Hz, 1H), 6.10 (t, J=6.0 Hz, 1H), 5.08 (m, 1H), 3.98 (s, 4H), 3.82 (s, 3H), 1.90 (m, 8H).

2-(1,4-Dioxa-spiro[4.5]dec-8-yloxy)-3-methoxy-pyridine:
$^1$H NMR (400 MHz, CDCl$_3$) δ 7.69 (d, J=6.0 Hz, 1H), 7.03 (d, J=6.2 Hz, 1H), 6.78 (t, J=6.4 Hz, 1H), 5.23 (m, 1H), 3.95 (m, 4H), 3.80 (s, 3H), 2.05 (m, 4H), 1.90 (m, 2H), 1.72 (m, 2H).

Step B: 3-Methoxy-1-(4-oxo-cyclohexyl)-1H-pyridin-2-one

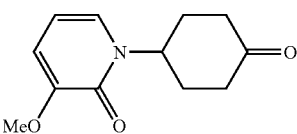

The title compound was prepared as a white solid from the de-protection of 1-(1,4-dioxa-spiro[4.5]dec-8-yl)-3-methoxy-1H-pyridin-2-one (as prepared in the previous step) using the procedure described in Step C of Example 1.

¹H NMR (400 MHz, CDCl₃) δ 6.90 (d, J=6.6 Hz, 1H), 6.62 (d, J=6.2 Hz, 1H), 6.20 (t, J=6.5 Hz, 1H), 5.45 (m, 1H), 3.85 (s, 3H), 2.65 (m, 2H), 2.54 (m, 2H), 2.28 (m, 2H), 2.02 (m, 2H).

Step C: N-({1-[4-(3-Methoxy-2-oxo-2H-pyridin-1-yl)-cyclohexyl]-azetidin-3-ylcarbamoyl}-methyl)-3-trifluoromethyl-benzamide

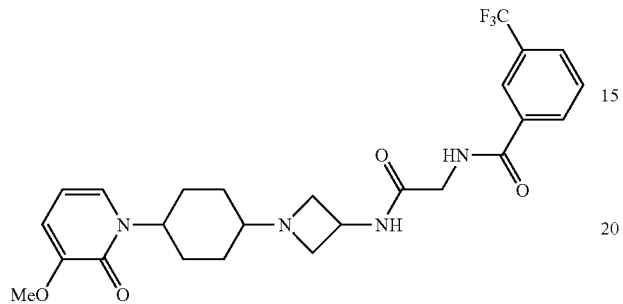

The title compounds were prepared as white solids from the reductive amination of 3-methoxy-1-(4-oxo-cyclohexyl)-1H-pyridin-2-one (as prepared in the previous step) and N-(azetidin-3-ylcarbamoylmethyl)-3-trifluoromethyl-benzamide (as prepared in Example 2 Step C) using the procedure described in Step D of Example 1.

13a: less polar fraction from silica gel column,
¹H NMR (400 MHz, CDCl₃) δ 8.20 (s, 1H), 8.08 (d, J=5.8 Hz, 1H), 7.78 (d, J=6.0 Hz, 1H), 7.62 (t, J=6.0 Hz, 1H), 7.48 (m, 1H), 7.20 (d, J=6.0 Hz, 1H), 6.60 (d, J=6.1 Hz, 1H), 6.15 (t, J=6.0 Hz, 1H), 5.05 (m, 1H), 4.51 (m, 1H), 4.20 (d, J=4.0 Hz, 2H), 3.80 (s, 3H), 3.68 (t, J=6.5 Hz, 2H), 3.15 (s, br, 2H), 2.51 (m, 1H), 1.95 (m, 2H), 1.80 (m, 2H), 1.60 (m, 4H).

13b: More Polar Fraction from Silica Gel Column
¹H NMR (400 MHz, CDCl₃) δ 8.21 (s, 1H), 8.10 (d, J=6.2 Hz, 1H), 7.80 (d, J=6.2 Hz, 1H), 7.65 (d, J=6.5 Hz, 1H), 7.50 (t, J=6.2 Hz, 1H), 7.06 (d, J=6.5 Hz, 1H), 6.75 (d, J=6.5 Hz, 1H), 6.21 (t, J=6.2 Hz, 1H), 4.90 (m, 1H), 4.55 (m, 1H), 4.10 (d, J=4.0 Hz, 2H), 3.82 (s, 3H), 3.70 (t, J=7.1 Hz, 2H), 2.95 (t, J=7.0 Hz, 2H), 2.50 (m, 1H), 2.00 (m, 2H), 1.75 (m, 2H), 1.55 (m, 2H), 1.38 (m, 2H).

Example 14

N-({1-[4-(3-Methoxy-pyridin-2-yloxy)-cyclohexyl]-azetidin-3-ylcarbamoyl}-methyl)-3-trifluoromethyl-benzamide Step A: 4-(3-Methoxy-pyridin-2-yloxy)-cyclohexanone

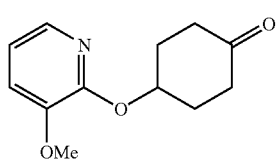

The title compound was prepared as a white solid from the de-protection of 2-(1,4-dioxa-spiro[4.5]dec-8-yloxy)-3-methoxy-pyridine (as prepared Example 13, Step A) using the procedure described in Step C of Example 1.

¹H NMR (400 MHz, CDCl₃) δ 7.70 (d, J=6.5 Hz, 1H), 7.05 (d, J=6.5 Hz, 1H), 6.82 (t, J=6.6 Hz, 1H), 5.51 (m, 1H), 3.80 (s, 3H), 2.75 (m, 2H), 2.45 (m, 2H), 2.23 (m, 4H).

Step B: N-({1-[4-(3-Methoxy-pyridin-2-yloxy)-cyclohexyl]-azetidin-3-ylcarbamoyl}-methyl)-3-trifluoromethyl-benzamide

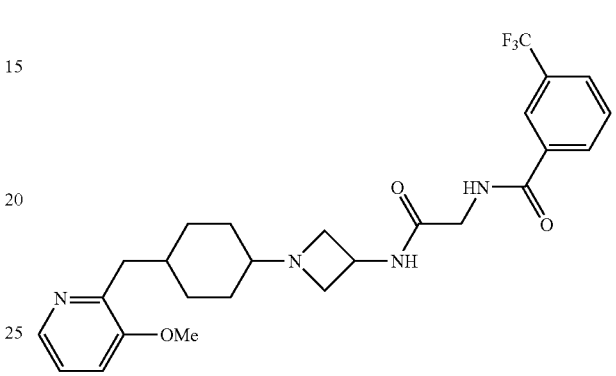

The title compounds were prepared as white solids from the reductive amination of 4-(3-methoxy-pyridin-2-yloxy)-cyclohexanone (as prepared in the previous step) and N-(azetidin-3-ylcarbamoylmethyl)-3-trifluoromethyl-benzamide (as prepared in Example 2 Step C) using the procedure described in Step D of Example 1.

¹H NMR (400 MHz, CDCl₃) δ 8.10 (s, 1H), 8.02 (d, J=5.8 Hz, 1H), 7.78 (d, J=6.0 Hz, 1H), 7.68 (d, J=6.0 Hz, 1H), 7.55 (t, J=6.2 Hz, 1H), 7.05 (d, J=6.0 Hz, 1H), 6.80 (d, J=6.1 Hz, 1H), 5.25 (m, 1H), 4.51 (m, 1H), 4.20 (d, J=4.0 Hz, 2H), 3.80 (s, 3H), 3.66 (t, J=6.5 Hz, 2H), 3.05 (t, J=6.0 Hz, 2H), 2.45 (m, 1H), 2.20 (m, 2H), 2.05 (m, 2H), 1.60 (m, 4H).

Example 15

N-({1-[4-(4-Hydroxy-2-oxo-2H-pyridin-1-yl)-cyclohexyl]-azetidin-3-ylcarbamoyl}-methyl)-3-trifluoromethyl-benzamide Step A: 1-(1,4-Dioxa-spiro[4.5]dec-8-yl)-4-hydroxy-1H-pyridin-2-one

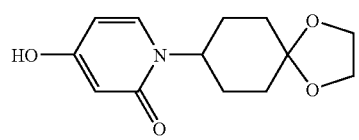

The title compound was prepared as a white solid from 4-hydroxy-1H-pyridin-2-one (Aldrich) using the procedure described in Step B of Example 1.

¹H NMR (400 MHz, CDCl₃) δ 7.25 (d, J=6.0 Hz, 1H), 5.98 (d, J=6.5 Hz, 1H), 5.88 (s, 1H), 4.35 (m, 1H), 3.98 (s, 4H), 1.90 (m, 6H), 1.67 (m, 2H).

Step B: 4-Hydroxy-1-(4-oxo-cyclohexyl)-1H-pyridin-2-one

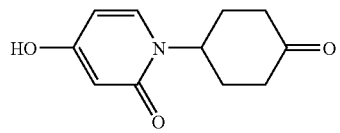

The title compound was prepared as a white solid from the de-protection of 1-(1,4-dioxa-spiro[4.5]dec-8-yl)-4-hydroxy-1H-pyridin-2-one (as prepared in the previous step) using the procedure described in Step C of Example 1.

ESI-MS (m/z): Calcd. For $C_{11}H_{13}NO_3$, 207; found: 208 (M+H).

Step C: N-({1-[4-(4-Hydroxy-2-oxo-2H-pyridin-1-yl)-cyclohexyl]-azetidin-3-ylcarbamoyl}-methyl)-3-trifluoromethyl-benzamide

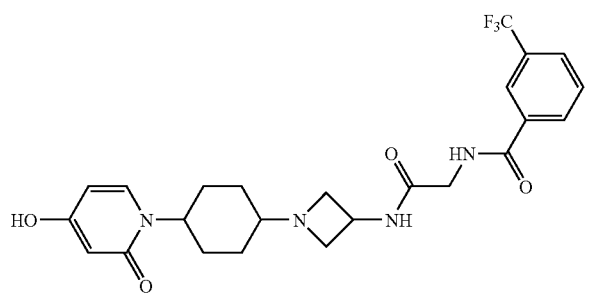

The title compounds were prepared as white solids from the reductive amination of 4-hydroxy-1-(4-oxo-cyclohexyl)-1H-pyridin-2-one (as prepared in the previous step) and N-(azetidin-3-ylcarbamoylmethyl)-3-trifluoromethyl-benzamide (as prepared in Example 2 Step C) using the procedure described in Step D of Example 1.

15a: Less Polar Fraction from Silica Gel Column,

¹H NMR (400 MHz, d₄-MeOH) δ 8.21 (s, 1H), 8.15 (d, J=6.5 Hz, 1H), 7.82 (d, J=6.0 Hz, 1H), 7.70 (t, J=7.2 Hz, 1H), 7.30 (d, J=4.2 Hz, 1H), 6.15 (d, J=6.5 Hz, 1H), 5.90 (s, 1H), 4.65 (s, br, 1H), 4.60 (m, 1H), 4.15 (s, 2H), 3.88 (t, J=7.5 Hz, 2H), 3.45 (t, J=7.2 Hz, 2H), 2.55 (m, 1H), 2.10 (m, 2H), 1.75 (m, 4H), 1.42 (m, 2H).

15b: More Polar Fraction from Silica Gel Column

¹H NMR (400 MHz, d₄-MeOH) δ 9.12 (s, br, 1H), 8.21 (s, 1H), 8.15 (d, J=6.5 Hz, 1H), 7.82 (d, J=6.0 Hz, 1H), 7.65 (t, J=7.2 Hz, 1H), 7.52 (d, J=4.2 hz, 1H), 7.18 (d, J=6.5 hz, 1H), 6.06 (d, J=5.6 Hz, 1H), 5.91 (s, 1H), 4.70 (m, 1H), 4.25 (s, 2H), 3.75 (t, J=7.5 Hz, 2H), 3.30 (t, J=7.2 Hz, 2H), 2.55 (m, 1H), 2.30 (m, 1H), 1.80 (m, 4H), 1.60 (m, 2H), 1.42 (m, 2H).

Example 16

N-({1-[4-(4-Oxo-4H-pyridin-1-yl)-cyclohexyl]-azetidin-3-ylcarbamoyl}-methyl)-3-trifluoromethyl-benzamide Step A: 1-(1,4-Dioxa-spiro[4.5]dec-8-yl)-1H-pyridin-4-one

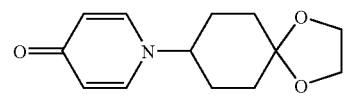

The title compound was prepared as a white solid from pyridin-4-ol (Aldrich) with t-BuOK (Aldrich) as the base using the procedure described in Step B of Example 1.

¹H NMR (400 MHz, CDCl₃) δ 6.78 (d, J=5.0 Hz, 2H), 5.50 (d, J=5.0 Hz, 2H), 4.51 (m, 1H), 3.98 (s, 4H), 1.95 (m, 6H), 1.65 (m, 2H).

Step B: 1-(4-Oxo-cyclohexyl)-1H-pyridin-4-one

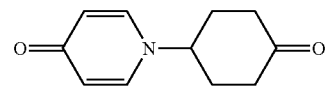

The title compound was prepared as a white solid from the de-protection of 1-(1,4-dioxa-spiro[4.5]dec-8-yl)-1H-pyridin-4-one (as prepared in the previous step) using the procedure described in Step C of Example 1.

ESI-MS (m/z): Calcd. For $C_{11}H_{13}NO_2$, 191; found: 192 (M+H).

Step C: N-({1-[4-(4-Oxo-4H-pyridin-1-yl)-cyclohexyl]-azetidin-3-ylcarbamoyl}-methyl)-3-trifluoromethyl-benzamide

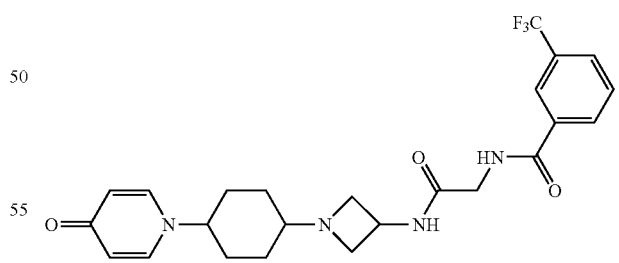

The title compounds were prepared as white solids from the reductive amination of 1-(4-oxo-cyclohexyl)-1H-pyridin-4-one (as prepared in the previous step) and N-(azetidin-3-ylcarbamoylmethyl)-3-trifluoromethyl-benzamide (as prepared in Example 2 Step C) using the procedure described in Step D of Example 1.

¹H NMR (400 MHz, d₄-MeOH) δ 8.21 (s, 1H), 8.05 (d, J=6.5 Hz, 1H), 7.87 (d, J=6.0 Hz, 1H), 7.65 (t, J=7.2 Hz, 1H), 6.98 (d, J=7.2 Hz, 2H), 5.75 (d, J=7.2 Hz, 2H), 4.60 (m, 1H), 4.05 9d, J=3.0 Hz, 2H), 3.85 (t, J=7.5 Hz, 2H), 3.50 (t, J=7.2 Hz, 2H), 2.70 (m, 1H), 2.35 (m, 1H), 2.08 (m, 2H), 1.80 (m, 4H), 1.65 (m, 2H).

Example 17

N-({1-[4-(3-Methyl-pyridin-2-yloxy)-cyclohexyl]-azetidin-3-ylcarbamoyl}-methyl)-3-trifluoromethyl-benzamide Step A: 1-(1,4-Dioxa-spiro[4.5]dec-8-yl)-3-methyl-1H-pyridin-2-one and 2-(1,4-Dioxa-spiro[4.5]dec-8-yloxy)-3-methyl-pyridine

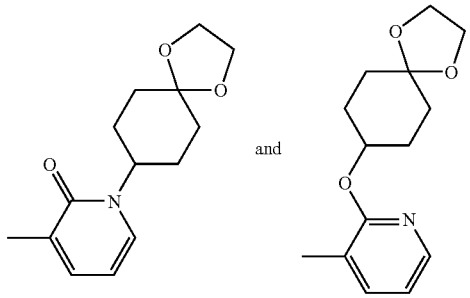

The title compounds were prepared as white solids from 2-hydroxy-3-methylpyridine (Aldrich) using the procedure described in Step B of Example 1.

1-(1,4-Dioxa-spiro[4.5]dec-8-yl)-3-methyl-1H-pyridin-2-one

ESI-MS (m/z): Calcd. For $C_{14}H_{19}NO_3$: 249.14; found: 250.1 (M+H).

2-(1,4-Dioxa-spiro[4.5]dec-8-yloxy)-3-methyl-pyridine

ESI-MS (m/z): Calcd. For $C_{14}H_{19}NO_3$: 249.14; found: 250.1 (M+H).

Step B: 4-(3-Methyl-pyridin-2-yloxy)-cyclohexanone

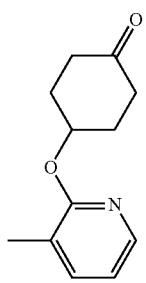

The title compound was prepared as a white solid from the de-protection of 2-(1,4-dioxa-spiro[4.5]dec-8-yloxy)-3-methyl-pyridine (as prepared in the previous step) using the procedure described in Step C of Example 1.

ESI-MS (m/z): Calcd. For $C_{12}H_{15}NO_2$: 205.11; found: 206.6 (M+H).

Step C: N-({1-[4-(3-Methyl-pyridin-2-yloxy)-cyclohexyl]-azetidin-3-ylcarbamoyl}-methyl)-3-trifluoromethyl-benzamide

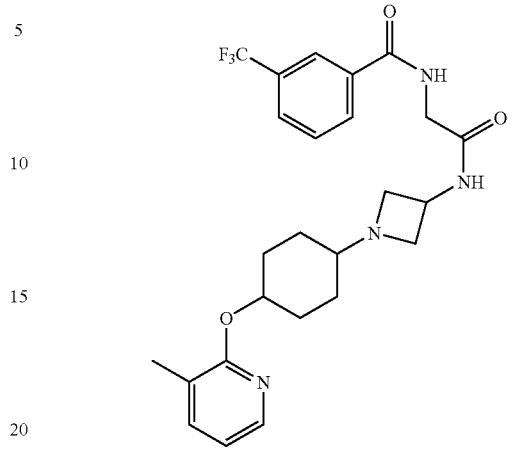

The title compounds were prepared as white solids from the reductive amination of 4-(3-methyl-pyridin-2-yloxy)-cyclohexanone (as prepared in the previous step) and N-(azetidin-3-ylcarbamoylmethyl)-3-trifluoromethyl-benzamide (as prepared in Example 2 Step C) using the procedure described in Step D of Example 1.

17a: Less Polar Isomer from Silica Gel Column,
$^1$H NMR (CHLOROFORM-d) δ: 8.12 (s, 1H), 8.02 (d, J=7.8 Hz, 1H), 7.79 (d, J=8.3 Hz, 1H), 7.56-7.67 (m, 1H), 7.40-7.49 (m, 1H), 7.16 (d, J=5.8 Hz, 1H), 6.06-6.21 (m, 1H), 4.91 (dd, J=15.8, 8.7 Hz, 1H), 4.50-4.65 (m, 1H), 4.14-4.23 (m, 2H), 3.62 (t, J=7.3 Hz, 2H), 2.85 (t, J=6.9 Hz, 2H), 2.32 (br. s., 1H), 2.14 (s, 3H), 1.80-1.92 (m, 2H), 1.75 (d, J=10.1 Hz, 2H), 1.52-1.64 (m, 4H)

17b: More Polar Isomer from Silica Gel Column
$^1$H NMR (MeOH) δ: 8.23 (br. s., 1H), 8.17 (d, J=7.6 Hz, 1H), 7.86 (d, J=7.1 Hz, 1H), 7.69 (t, J=7.7 Hz, 1H), 7.50 (d, J=6.8 Hz, 1H), 7.36 (d, J=6.3 Hz, 1H), 6.34 (t, J=6.8 Hz, 1H), 4.91 (br s., 2H), 4.47 (t, J=9.3 Hz, 2H), 4.00-4.17 (m, 2H), 2.17-2.26 (m, 2H), 2.11 (s, 1H), 1.95 (s, 3H), 1.71-1.89 (m, 2H), 1.61 (br. s., 2H), 1.48-1.58 (m, 4H).

Example 18

N-({1-[4-(3-Methyl-2-oxo-2H-pyridin-1-yl)-cyclohexyl]-azetidin-3-ylcarbamoyl}-methyl)-3-trifluoromethyl-benzamide Step A: 3-Methyl-1-(4-oxo-cyclohexyl)-1H-pyridin-2-one

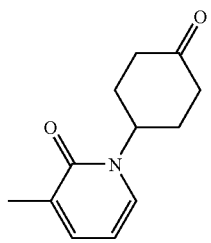

The title compound was prepared as a white solid from the de-protection of 1-(1,4-dioxa-spiro[4.5]dec-8-yl)-3-methyl-1H-pyridin-2-one (as prepared in Example 17, Step A) using the procedure described in Step C of Example 1.

$^1$H NMR (CHLOROFORM-d) δ: 2.66 (td, J=10.0, 5.3 Hz, 2H), 2.37-2.47 (m, 2H), 2.26-2.35 (m, 2H), 2.08-2.19 (m, 2H).

Step B: N-({1-[4-(3-Methyl-2-oxo-2H-pyridin-1-yl)-cyclohexyl]-azetidin-3-ylcarbamoyl}-methyl)-3-trifluoromethyl-benzamide

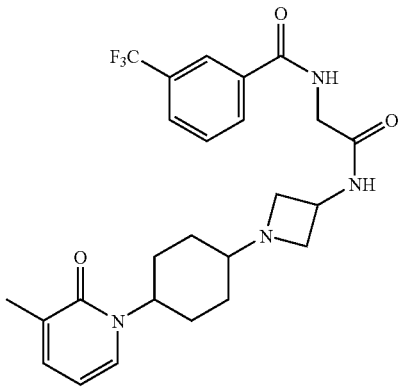

The title compounds were prepared as white solids from the reductive amination of 3-methyl-1-(4-oxo-cyclohexyl)-1H-pyridin-2-one (as prepared in the previous step) and N-(azetidin-3-ylcarbamoylmethyl)-3-trifluoromethyl-benzamide (as prepared in Example 2 Step C) using the procedure described in Step D of Example 1.

18a: Less Polar Isomer from Silica Gel Column,
$^1$H NMR (MeOH) δ: 8.24 (s, 1H), 8.16 (d, J=7.8 Hz, 1H), 7.84-8.02 (m, 1H), 7.63-7.80 (m, 1H), 7.41-7.56 (m, 1H), 6.81 (dd, J=7.2, 5.2 Hz, 1H), 5.24 (br. s., 1H), 4.50 (s, 1H), 4.06 (br s, 2H), 3.64-3.77 (m, 2H), 3.05 (dd, J=8.7, 7.2 Hz, 2H), 2.31 (s, 1H), 2.21 (s, 3H), 1.98-2.11 (m, 2H), 1.63 (d, J=10.6 Hz, 4H), 1.49 (br. s., 2H).

18b: More Polar Isomer from Silica Gel Column
$^1$H NMR (MeOH) δ: 8.24 (br. s., 1H), 8.16 (d, J=7.3 Hz, 1H), 7.83-7.97 (m, 2H), 7.71 (t, J=7.8 Hz, 1H), 7.47 (d, J=7.1 Hz, 1H), 6.73-6.89 (m, 1H), 4.96 (t, J=10.5 Hz, 1H), 4.49 (t, J=7.1 Hz, 1H), 4.06 (br s, 2H), 3.70 (t, J=7.7 Hz, 2H), 3.07 (t, J=7.7 Hz, 2H), 2.41 (s, 3H), 2.17-2.27 (m, 2H), 1.91 (d, J=14.1 Hz, 2H), 1.34-1.54 (m, 2H), 1.12-1.30 (m, 2H).

Example 19

N-({1-[4-(4-Methyl-pyridin-2-yloxy)-cyclohexyl]-azetidin-3-ylcarbamoyl}-methyl)-3-trifluoromethyl-benzamide Step A: 1-(1,4-Dioxa-spiro[4.5]dec-8-yl)-4-methyl-1H-pyridin-2-one and 2-(1,4-Dioxa-spiro[4.5]dec-8-yloxy)-4-methyl-pyridine

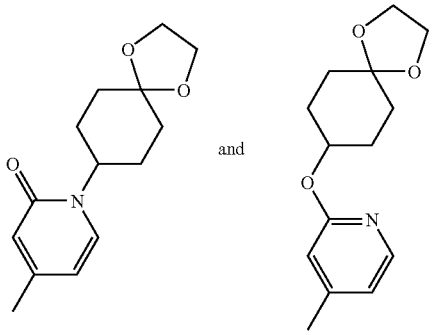

The title compounds were prepared as white solids from 2-hydroxy-4-methylpyridine (Aldrich) using the procedure described in Step B of Example 1.

1-(1,4-Dioxa-spiro[4.5]dec-8-yl)-4-methyl-1H-pyridin-2-one
ESI-MS (m/z): Calcd. For $C_{14}H_{21}NO_3$: 251.15; found: 252.1 (M+H).

2-(1,4-Dioxa-spiro[4.5]dec-8-yloxy)-4-methyl-pyridine
ESI-MS (m/z): Calcd. For $C_{14}H_{19}NO_3$: 249.14; found: 250.1 (M+H).

Step B: 4-(5-Methyl-pyridin-2-yloxy)-cyclohexanone

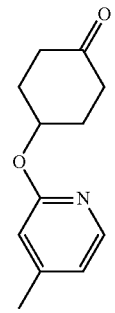

The title compound was prepared as a white solid from the de-protection of 2-(1,4-dioxa-spiro[4.5]dec-8-yloxy)-4-methyl-pyridine (as prepared in the previous step) using the procedure described in Step C of Example 1.

ESI-MS (m/z): Calcd. For $C_{12}H_{15}NO_2$: 205.11; found: 206.6 (M+H).

Step C: N-({1-[4-(4-Methyl-pyridin-2-yloxy)-cyclohexyl]-azetidin-3-ylcarbamoyl}-methyl)-3-trifluoromethyl-benzamide

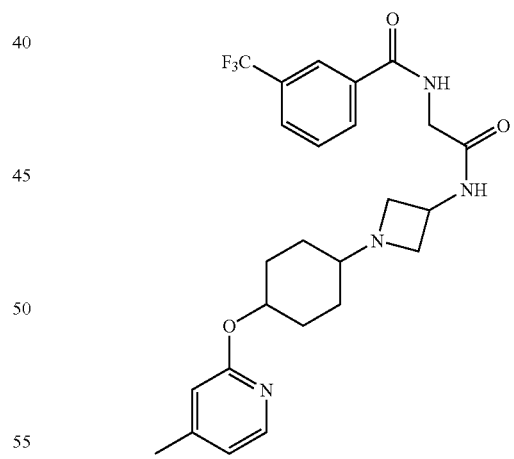

The title compounds were prepared as white solids from the reductive amination of 4-(4-methyl-pyridin-2-yloxy)-cyclohexanone (as prepared in the previous step) and N-(azetidin-3-ylcarbamoylmethyl)-3-trifluoromethyl-benzamide (as prepared in Example 2 Step C) using the procedure described in Step D of Example 1.

$^1$H NMR (CHLOROFORM-d) δ: 8.13 (s, 1H), 8.03 (d, J=7.8 Hz, 1H), 7.95-8.00 (m, 1H), 7.77 (d, J=7.6 Hz, 1H), 7.71 (d, J=3.8 Hz, 1H), 7.52-7.58 (m, 1H), 6.65 (t, J=4.8 Hz, 1H), 4.95 (br s., 1H), 4.47-4.66 (m, 1H), 4.16-4.26 (m, 2H), 3.64 (t, J=6.7 Hz, 2H), 2.85-3.04 (m, 2H), 2.27 (s, 3H), 2.04-2.18 (m, 1H), 1.99 (d, J=13.1 Hz, 2H), 1.79 (d, J=12.9 Hz, 2H), 1.42-1.63 (m, 4H).

Example 20

N-({1-[4-(4-Methyl-2-oxo-2H-pyridin-1-yl)-cyclohexyl]-azetidin-3-ylcarbamoyl}-methyl)-3-trifluoromethyl-benzamide Step A: 4-Methyl-1-(4-oxo-cyclohexyl)-1H-pyridin-2-one

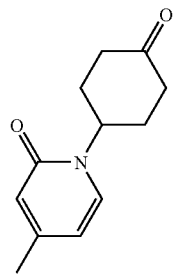

The title compound was prepared as a white solid from the de-protection of 1-(1,4-dioxa-spiro[4.5]dec-8-yl)-4-methyl-1H-pyridin-2-one (as prepared in Example 19, Step A) using the procedure described in Step C of Example 1.

$^1$H NMR (CHLOROFORM-d) δ: 7.20 (d, J=7.1 Hz, 1H), 6.50 (s, 1H), 6.15 (d, J=6.8 Hz, 1H), 5.40 (t, J=12.4 Hz, 1H), 2.63 (dd, J=14.1, 5.6 Hz, 2H), 2.49-2.58 (m, 2H), 2.24 (br. s., 2H), 2.20 (s, 3H), 1.97 (d, J=15.2 Hz, 2H).

Step B: N-({1-[4-(4-Methyl-2-oxo-2H-pyridin-1-yl)-cyclohexyl]-azetidin-3-ylcarbamoyl}-methyl)-3-trifluoromethyl-benzamide

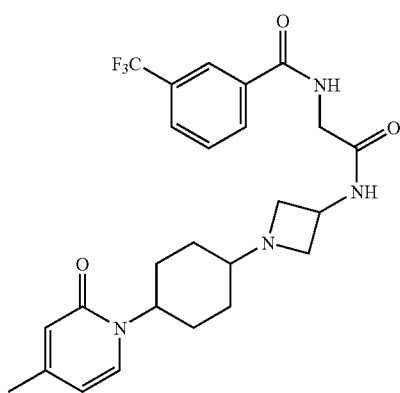

The title compounds were prepared as white solids from the reductive amination of 4-methyl-1-(4-oxo-cyclohexyl)-1H-pyridin-2-one (as prepared in the previous step) and N-(azetidin-3-ylcarbamoylmethyl)-3-trifluoromethyl-benzamide (as prepared in Example 2 Step C) using the procedure described in Step D of Example 1.

$^1$H NMR (CHLOROFORM-d) δ: 8.15 (s, 1H), 8.05 (d, J=7.8 Hz, 1H), 7.78 (d, J=7.8 Hz, 1H), 7.59 (d, J=15.4 Hz, 1H), 7.48 (d, J=7.1 Hz, 1H), 7.37 (t, J=4.8 Hz, 1H), 6.05 (dd, J=7.2, 1.9 Hz, 1H), 4.89 (t, J=12.3 Hz, 1H), 4.57-4.74 (m, 1H), 4.18 (d, J=5.1 Hz, 2H), 3.70 (d, J=15.2 Hz, 2H), 3.17 (br. s., 2H), 2.53 (br. s., 1H), 2.16 (s, 3H), 1.89 (d, J=11.6 Hz, 2H), 1.73-1.84 (m, 2H), 1.53-1.68 (m, 4H).

Example 21

N-({1-[4-(2-Oxo-5-trifluoromethyl-2H-pyridin-1-yl)-cyclohexyl]-azetidin-3-ylcarbamoyl}-methyl)-3-trifluoromethyl-benzamide Step A: 1-(1,4-Dioxa-spiro[4.5]dec-8-yl)-3-trifluoromethyl-1H-pyridin-2-one

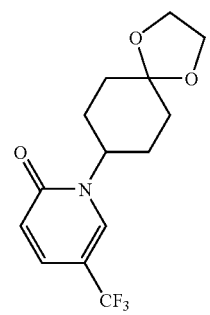

The title compound was prepared as a white solid from 2-hydroxy-5-trifluoromethylpyridine (Aldrich) using the procedure described in Step B of Example 1.

ESI-MS (m/z): Calcd. For $C_{14}H_{16}F_3NO_3$: 303.11; found: 304 (M+H).

Step B: 1-(4-Oxo-cyclohexyl)-5-trifluoromethyl-1H-pyridin-2-one

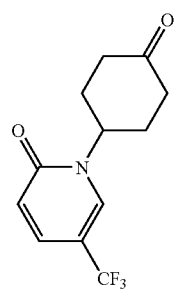

The title compound was prepared as a white solid from the de-protection of 1-(4-oxo-cyclohexyl)-5-trifluoromethyl-1H-pyridin-2-one (as prepared in the previous step) using the procedure described in Step C of Example 1.

$^1$H NMR (MeOH) δ: 7.89 (s, 1H), 7.54 (d, J=12.1 Hz, 1H), 6.54 (d, J=9.6 Hz, 1H), 3.77-3.95 (m, 1H), 2.10 (d, J=14.1 Hz, 2H), 1.59 (t, J=9.5 Hz, 6H).

Step C: N-({1-[4-(2-Oxo-5-trifluoromethyl-2H-pyridin-1-yl)-cyclohexyl]-azetidin-3-ylcarbamoyl}-methyl)-3-trifluoromethyl-benzamide

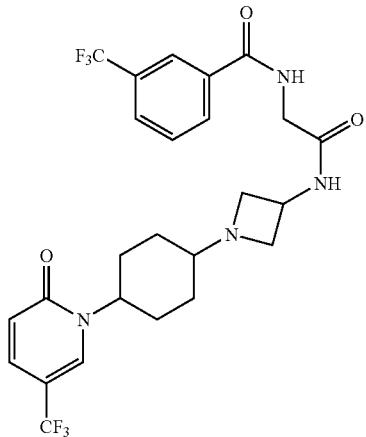

The title compounds were prepared as white solids from the reductive amination of 1-(4-oxo-cyclohexyl)-5-trifluoromethyl-1H-pyridin-2-one (as prepared in the previous step) and N-(azetidin-3-ylcarbamoylmethyl)-3-trifluoromethyl-benzamide (as prepared in Example 2 Step C) using the procedure described in Step D of Example 1.

21a: Less Polar Isomer from Silica Gel Column,
$^1$H NMR (MeOH) δ: 8.39 (s, 1H), 8.24 (s, 1H), 8.16 (d, J=7.8 Hz, 1H), 7.88 (d, J=8.6 Hz, 1H), 7.71 (t, J=7.8 Hz, 1H), 7.64 (dd, J=9.6, 2.5 Hz, 1H), 6.64 (d, J=9.6 Hz, 1H), 4.89-5.01 (m, 1H), 4.57 (t, J=7.2 Hz, 1H), 4.07 (s, 2H), 3.70-3.86 (m, 2H), 3.04 (t, J=7.8 Hz, 2H), 2.52 (br. s., 1H), 1.83-1.98 (m, 4H), 1.67 (br. s., 2H), 1.60 (br. s., 2H).

21b: More Polar Isomer from Silica Gel Column
$^1$H NMR (MeOH) δ: 8.39 (s, 1H), 8.24 (s, 1H), 8.16 (d, J=7.8 Hz, 1H), 7.89 (d, J=8.1 Hz, 1H), 7.71 (t, J=7.8 Hz, 1H), 7.22 (br s., 1H), 6.64 (d, J=9.6 Hz, 1H), 4.89-5.01 (m, 1H), 4.45-4.56 (m, 1H), 3.62-3.74 (m, 2H), 2.96-3.15 (m, 2H), 2.25-2.35 (m, 1H), 2.06 (d, J=15.7 Hz, 2H), 1.89-1.94 (m, 2H), 1.75-1.87 (m, 2H), 1.61-1.73 (m, 2H), 1.42 (d, J=10.9 Hz, 2H).

Example 22

N-({1-[4-(2-Oxo-5-trifluoromethyl-2H-pyridin-1-yl)-cyclohexyl]-azetidin-3-ylcarbamoyl}-methyl)-3-trifluoromethyl-benzamide Step A: 5-Chloro-1-(1,4-dioxa-spiro[4.5]dec-8-yl)-1H-pyridin-2-one

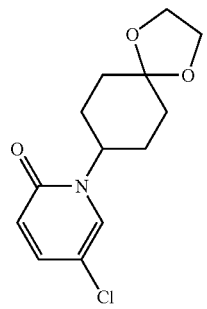

The title compound was prepared as a white solid from 2-hydroxy-5-chloropyridine (Aldrich) using the procedure described in Step B of Example 1.

$^1$H NMR (CHLOROFORM-d) δ: 7.39 (d, J=2.8 Hz, 1H), 7.24 (dd, J=9.6, 2.8 Hz, 1H), 6.54 (d, J=9.6 Hz, 1H), 4.89-5.04 (m, 4H), 1.75-1.94 (m, 8H).

Step B: 1-(4-Oxo-cyclohexyl)-5-chloro-1H-pyridin-2-one

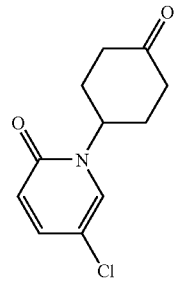

The title compound was prepared as a white solid from the de-protection of 5-chloro-1-(1,4-dioxa-spiro[4.5]dec-8-yl)-1H-pyridin-2-one (as prepared in the previous step) using the procedure described in Step C of Example 1.

ESI-MS (m/z): Calcd. For $C_{11}H_{12}F_3ClNO_3$: 225.11; found: 226.1 (M+H).

Step C: N-({1-[4-(2-Oxo-5-chloro-2H-pyridin-1-yl)-cyclohexyl]-azetidin-3-ylcarbamoyl}-methyl)-3-trifluoromethyl-benzamide

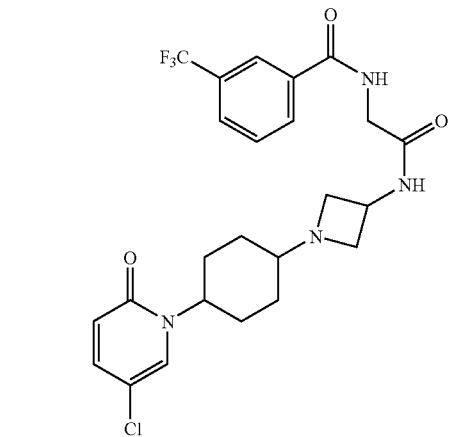

The title compounds were prepared as white solids from the reductive amination of 1-(4-oxo-cyclohexyl)-5-chloro-1H-pyridin-2-one (as prepared in the previous step) and N-(azetidin-3-ylcarbamoylmethyl)-3-trifluoromethyl-benzamide (as prepared in Example 2 Step C) using the procedure described in Step D of Example 1.

22a: Less Polar Isomer from Silica Gel Column,
$^1$H NMR (CHLOROFORM-d) δ: 8.13 (s, 1H), 8.02 (d, J=8.1 Hz, 1H), 7.79 (d, J=7.8 Hz, 1H), 7.57-7.69 (m, 1H), 7.45 (d, J=2.8 Hz, 1H), 7.37 (t, J=4.8 Hz, 1H), 6.95 (d, J=7.8 Hz, 1H), 4.73-4.93 (m, 1H), 4.50-4.63 (m, 1H), 4.20 (d, J=4.8 Hz, 2H), 3.64 (t, J=7.3 Hz, 2H), 2.87 (t, J=7.1 Hz, 2H), 2.33 (br. s., 1H), 1.70-1.80 (m, 4H), 1.46-1.63 (m, 4H).

22b: More Polar Isomer from Silica Gel Column
$^1$H NMR (CHLOROFORM-d) δ: 8.13 (s, 1H), 8.02 (d, J=7.8 Hz, 1H), 7.79 (d, J=7.6 Hz, 1H), 7.59 (t, J=7.8 Hz, 1H), 7.51 (t, J=4.8 Hz, 1H), 7.45 (d, J=2.8 Hz, 1H), 7.14 (d, J=7.6 Hz, 1H), 4.75-4.89 (m, 1H), 4.50-4.65 (m, 1H), 4.21 (d, J=4.8 Hz, 2H), 3.64 (t, J=7.3 Hz, 2H), 2.81-2.88 (m, 2H), 2.32 (br. s., 1H), 1.69-1.93 (m, 4H), 1.47-1.63 (m, 4H).

Example 23

N-({1-[4-(Pyridazin-3-yloxy)-cyclohexyl]-azetidin-3-ylcarbamoyl}-methyl)-3-trifluoromethyl-benzamide Step A:
3-(1,4-Dioxa-spiro[4.5]dec-8-yloxy)-pyridazine

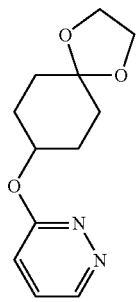

The title compound was prepared as a white solid from pyridazin-3-ol (Aldrich) using the procedure described in Step B of Example 1.
¹H NMR (MeOH) δ: 7.90-8.04 (m, 1H), 7.40 (dd, J=9.3, 3.8 Hz, 1H), 6.97 (d, J=9.3 Hz, 1H), 4.88-5.04 (m, 1H), 3.97 (br s, 4H), 2.04-2.21 (m, 2H), 1.77-1.93 (m, 6H).

Step B: 4-(Pyridazin-3-yloxy)-cyclohexanone

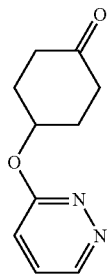

The title compound was prepared as a white solid from the de-protection of 3-(1,4-dioxa-spiro[4.5]dec-8-yloxy)-pyridazine (as prepared in the previous step) using the procedure described in Step C of Example 1.
¹H NMR (CHLOROFORM-d) δ: 7.83 (d, J=5.6 Hz, 1H), 7.15-7.27 (m, 1H), 6.97 (d, J=9.3 Hz, 1H), 4.88-5.04 (m, 1H), 2.49-2.69 (m, 4H), 2.11-2.35 (m, 4H).

Step C: N-({1-[4-(Pyridazin-3-yloxy)-cyclohexyl]-azetidin-3-ylcarbamoyl}-methyl)-3-trifluoromethyl-benzamide

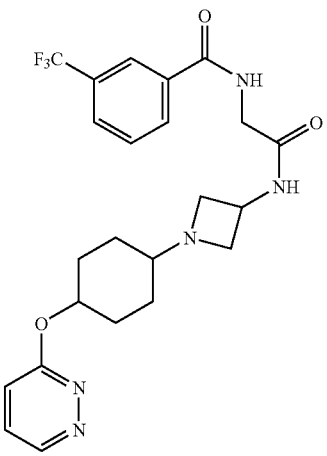

The title compounds were prepared as white solids from the reductive amination of 4-(pyridazin-3-yloxy)-cyclohexanone (as prepared in the previous step) and N-(azetidin-3-ylcarbamoylmethyl)-3-trifluoromethyl-benzamide (as prepared in Example 2 Step C) using the procedure described in Step D of Example 1.
¹H NMR (MeOH) δ: 8.17 (s, 1H), 8.07 (d, J=7.8 Hz, 1H), 7.85-7.94 (m, 1H), 7.79 (d, J=7.8 Hz, 1H), 7.61 (t, J=7.8 Hz, 1H), 7.22 (dd, J=9.3, 3.8 Hz, 1H), 6.93 (dd, J=9.5, 1.6 Hz, 1H), 4.81-5.04 (m, 1H), 4.43-4.56 (m, 2H), 3.42 (br s, 2H), 2.94 (t, J=6.7 Hz, 2H), 2.35 (br. s., 1H), 2.03-2.22 (m, 2H), 1.72-1.89 (m, 2H), 1.48-1.67 (m, 4H).

Example 24

N-({1-[4-(1,3-Dioxo-1,3-dihydro-isoindol-2-yl)-cyclohexyl]-azetidin-3-ylcarbamoyl}-methyl)-3-trifluoromethyl-benzamide Step A: 2-(1,4-Dioxa-spiro[4.5]dec-8-yl)-isoindole-1,3-dione

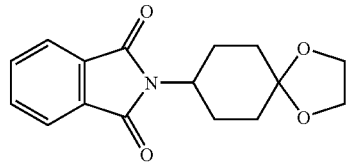

The title compound was prepared as a white solid from isoindole-1,3-dione (Aldrich) with NaH as the base using the procedure described in Step B of Example 1.
¹H NMR (400 MHz, CDCl₃) δ 7.88 (d, J=6.0 Hz, 2H), 7.65 (d, J=6.5 Hz, 2H), 3.98 (s, 4H), 3.80 (m, 1H), 1.90 (m, 4H), 1.66 (m, 4H).

Step B: 2-(4-Oxo-cyclohexyl)-isoindole-1,3-dione

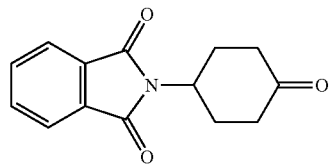

The title compound was prepared as a white solid from the de-protection of 2-(1,4-dioxa-spiro[4.5]dec-8-yl)-isoindole-1,3-dione (as prepared in the previous step) using the procedure described in Step C of Example 1.
ESI-MS (m/z): Calcd. For $C_{14}H_{13}NO_3$, 243; found: 244 (M+H).

Step C: N-({1-[4-(1,3-Dioxo-1,3-dihydro-isoindol-2-yl)-cyclohexyl]-azetidin-3-ylcarbamoyl}-methyl)-3-trifluoromethyl-benzamide

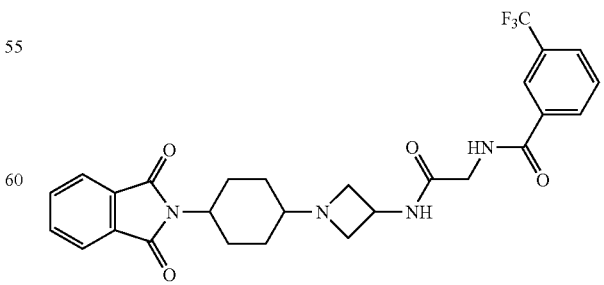

The title compounds were prepared as white solids from the reductive amination of 2-(4-oxo-cyclohexyl)-isoindole-1, 3-dione (as prepared in the previous step) and N-(azetidin-3-ylcarbamoylmethyl)-3-trifluoromethyl-benzamide (as prepared in Example 2 Step C) using the procedure described in Step D of Example 1.

24a: Less Polar Fraction from Silica Gel Column,
$^1$H NMR (400 MHz, CDCl$_3$) δ 8.15 (s, 1H), 8.02 (d, J=6.5 Hz, 1H), 7.80 (m, 3H), 7.69 (m, 1H), 7.55 (t, J=6.6 Hz, 1H), 7.18 (m, 1H), 6.82 (d, J=6.5 Hz, 1H), 4.55 (m, 1H), 4.20 (s, 2H), 4.10 (m, 1H), 3.52 (m, 2H), 2.98 (t, J=5.5 Hz, 2H), 2.52 (m, 1H), 2.01 (m, 2H), 1.75 (m, 2H), 1.46 (m, 4H).

24b: More Polar Fraction from Silica Gel Column
$^1$H NMR (400 MHz, CDCl$_3$) δ 8.11 (s, 1H), 8.05 (m, 2H), 7.75 (m, 3H), 7.60 (d, J=5.8 Hz, 1H), 7.55 (t, J=6.6 Hz, 1H), 7.28 (m, 2H), 4.62 (s, br, 1H), 4.51 (m, 1H), 4.20 (s, 2H), 4.10 (m, 1H), 3.55 (t, J=6.5 Hz, 2H), 2.90 (t, J=6.5 Hz, 2H), 2.00 (m, 1H), 1.90 (m, 1H), 1.40 (m, 6H).

Example 25

N-({1-[4-(2,3-Dihydro-benzo[d]isoxazol-3-yloxy)-cyclohexyl]-azetidin-3-ylcarbamoyl}-methyl)-3-trifluoromethyl-benzamide Step A: 2-(1,4-Dioxa-spiro[4.5]dec-8-yl)-benzo[d]isoxazol-3-one and 3-(1,4-Dioxa-spiro[4.5]dec-8-yloxy)-benzo[d]isoxazole

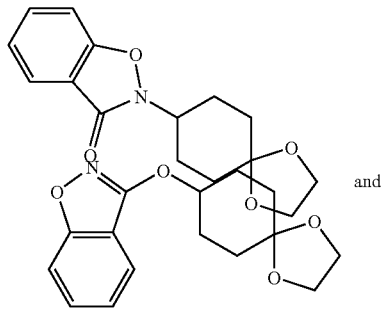

The title compounds were prepared as white solids from benzisoxazole-3-ol (Aldrich) using the procedure described in Step B of Example 1.

2-(1,4-Dioxa-spiro[4.5]dec-8-yl)-benzo[d]isoxazol-3-one
$^1$H NMR (CHLOROFORM-d) δ: 7.63 (d, J=7.8 Hz, 1H), 7.51 (ddd, J=8.3, 7.1, 1.3 Hz, 1H), 7.42 (d, J=8.3 Hz, 1H), 7.25 (t, J=7.5 Hz, 1H), 5.04 (t, J=5.2 Hz, 1H), 3.87-4.15 (m, 4H), 2.12 (q, J=6.1 Hz, 4H), 1.94 (dt, J=13.5, 6.5 Hz, 2H), 1.70 (dt, J=13.2, 6.4 Hz, 2H).

3-(1,4-Dioxa-spiro[4.5]dec-8-yloxy)-benzo[d]isoxazole
$^1$H NMR (CHLOROFORM-d) δ: 7.63 (d, J=7.8 Hz, 1H), 7.51 (ddd, J=8.3, 7.1, 1.3 Hz, 1H), 7.42 (d, J=8.3 Hz, 1H), 7.25 (t, J=7.5 Hz, 1H), 5.04 (t, J=5.2 Hz, 1H), 3.87-4.15 (m, 4H), 2.12 (q, J=6.1 Hz, 4H), 1.94 (dt, J=13.5, 6.5 Hz, 2H), 1.70 (dt, J=13.2, 6.4 Hz, 2H).

Step B:
4-(Benzo[d]isoxazol-3-yloxy)-cyclohexanone

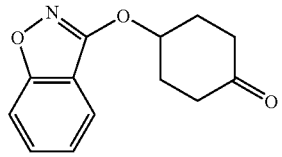

The title compound was prepared as a white solid from the de-protection of 3-(1,4-dioxa-spiro[4.5]dec-8-yloxy)-benzo[d]isoxazole (as prepared in the previous step) using the procedure described in Step C of Example 1.

$^1$H NMR (CHLOROFORM-d) δ: 7.67 (d, J=7.8 Hz, 1H), 7.51-7.59 (m, 1H), 7.45 (d, J=8.6 Hz, 1H), 7.21-7.36 (m, 1H), 5.14-5.40 (m, 1H), 2.59-2.77 (m, 2H), 2.41-2.55 (m, 4H), 2.27-2.35 (m, 2H).

Step C: N-({1-[4-(Benzo[d]isoxazol-3-yloxy)-cyclohexyl]azetidin-3-ylcarbamoyl}-methyl)-3-trifluoromethyl-benzamide

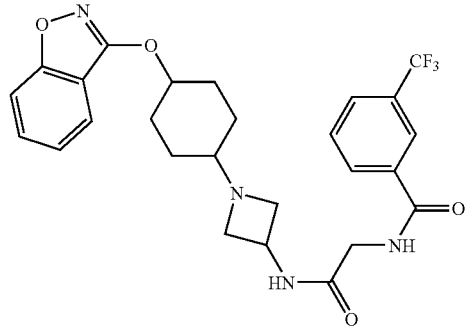

The title compounds were prepared as white solids from the reductive amination of 4-(benzo[d]isoxazol-3-yloxy)-cyclohexanone (as prepared in the previous step) and N-(azetidin-3-ylcarbamoylmethyl)-3-trifluoromethyl-benzamide (as prepared in Example 2 Step C) using the procedure described in Step D of Example 1.

25a: Less Polar Fraction from Silica Gel Column,
$^1$H NMR (CHLOROFORM-d) δ: 8.14 (s, 1H), 8.02 (d, J=7.8 Hz, 1H), 7.77 (d, J=9.6 Hz, 2H), 7.47-7.69 (m, 1H), 7.35-7.47 (m, 2H), 7.19-7.30 (m, 1H), 4.98-5.11 (m, 1H), 4.44-4.65 (m, 1H), 4.21 (d, J=5.1 Hz, 2H), 3.67 (t, J=7.5 Hz, 2H), 2.95 (t, J=7.1 Hz, 2H), 2.21 (dd, J=13.6, 4.8 Hz, 2H), 2.09 (td, J=8.4, 4.2 Hz, 1H), 1.63-1.75 (m, 2H), 1.46-1.62 (m, 4H)

25b: More Polar Fraction from Silica Gel Column
$^1$H NMR (CHLOROFORM-d) δ: 8.18 (s, 1H), 8.08 (d, J=7.8 Hz, 1H), 7.79 (d, J=7.8 Hz, 1H), 7.58-7.69 (m, 2H), 7.54 (t, J=7.7 Hz, 1H), 7.43 (d, J=8.6 Hz, 1H), 7.27 (t, J=7.5 Hz, 1H), 4.68-4.87 (m, 1H), 4.48 (quin, J=6.4 Hz, 2H), 3.75 (s, 1H), 3.64 (t, J=7.8 Hz, 2H), 3.01-3.10 (m, 2H), 2.36 (d, J=9.9 Hz, 2H), 2.17 (t, J=10.6 Hz, 1H), 1.89 (d, J=10.9 Hz, 2H), 1.47-1.65 (m, 4H), 1.13-1.24 (m, 2H).

Example 26

N-({1-[4-(3-Oxo-3H-benzo[d]isoxazol-2-yl)-cyclohexyl]-azetidin-3-ylcarbamoyl}-methyl)-3-trifluoromethyl-benzamide Step A:
2-(4-Oxo-cyclohexyl)-benzo[d]isoxazol-3-one

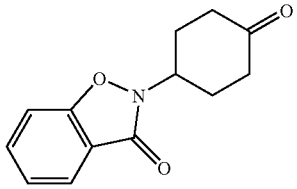

The title compound was prepared as a white solid from the de-protection of 2-(1,4-dioxa-spiro[4.5]dec-8-yl)-benzo[d]isoxazol-3-one (as prepared in example 25, Step A) using the procedure described in Step C of Example 1.

$^1$H NMR (CHLOROFORM-d) δ: 7.85 (d, J=9.9 Hz, 1H), 7.64 (d, J=6.1 Hz, 1H), 7.42-7.51 (m, 1H), 7.27 (d, J=7.3 Hz, 1H), 4.89-5.01 (m, 1H), 2.55-2.61 (m, 4H), 2.21-2.37 (m, 4H).

Step B: N-({1-[4-(3-Oxo-3H-benzo[d]isoxazol-2-yl)-cyclohexyl]azetidin-3-ylcarbamoyl}-methyl)-3-trifluoromethyl-benzamide

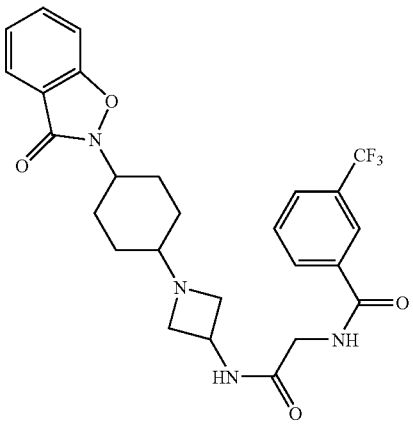

The title compounds were prepared as white solids from the reductive amination of 4-(benzo[d]isoxazol-3-yloxy)-cyclohexanone (as prepared in the previous step) and N-(azetidin-3-ylcarbamoylmethyl)-3-trifluoromethyl-benzamide (as prepared in Example 2 Step C) using the procedure described in Step D of Example 1.

26a: Less Polar Fraction from Silica Gel Column, $^1$H NMR (CHLOROFORM-d) δ: 8.14 (s, 1H), 8.03 (d, J=7.8 Hz, 1H), 7.78 (d, J=7.8 Hz, 1H), 7.82 (d, J=7.8 Hz, 1H), 7.47-7.69 (m, 3H), 7.14 (d, J=7.8 Hz, 1H), 4.53-4.70 (m, 1H), 4.41-4.53 (m, 1H), 4.21 (d, J=4.8 Hz, 2H), 3.65 (t, J=7.5 Hz, 2H), 2.89 (t, J=7.1 Hz, 2H), 2.27-2.37 (m, 1H), 2.13-2.26 (m, 2H), 1.74 (d, J=13.6 Hz, 2H), 1.64 (d, J=12.4 Hz, 2H), 1.47-1.58 (m, 2H).

26b: More Polar Fraction from Silica Gel Column $^1$H NMR (CHLOROFORM-d) δ: 8.08-8.21 (m, 1H), 8.02 (d, J=8.1 Hz, 1H), 7.72-7.90 (m, 1H), 7.60 (t, J=7.8 Hz, 1H), 7.30-7.39 (m, 2H), 7.19-7.30 (m, 2H), 4.53-4.70 (m, 1H), 4.41-4.53 (m, 2H), 4.13-4.22 (m, 2H), 3.53-3.75 (m, 2H), 2.98-3.12 (m, 1H), 1.95-2.12 (m, 2H), 1.76-1.93 (m, 2H), 1.16-1.32 (m, 2H), 0.87-1.09 (m, 2H).

Example 27

N-({1-[4-(4-Methyl-pyrazol-1-yl)-cyclohexyl]-azetidin-3-ylcarbamoyl}-methyl)-3-trifluoromethyl-benzamide Step A: 1-(1,4-Dioxa-spiro[4.5]dec-8-yl)-4-methyl-1H-pyrazole

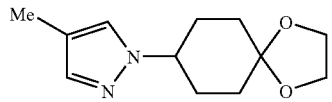

The title compound was prepared as a white solid from 3-methyl-pyrazole (Aldrich) using the procedure described in Step B of Example 1.

$^1$H NMR (400 MHz, CDCl$_3$) δ 7.28 (s, 1H), 7.21 9s, 1H), 4.18 (m, 1H), 3.98 (s, 4H), 2.10 (m, 2H), 2.05 (m, 2H), 1.90 (m, 2H), 1.75 (m, 2H).

Step B: 4-(4-Methyl-pyrazol-1-yl)-cyclohexanone

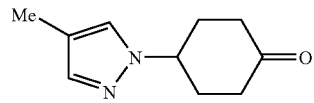

The title compound was prepared as a white solid from the de-protection of 1-(1,4-dioxa-spiro[4.5]dec-8-yl)-4-methyl-1H-pyrazole (as prepared in the previous step) using the procedure described in Step C of Example 1.

$^1$H NMR (400 MHz, CDCl$_3$) δ 7.35 (s, 1H), 7.25 (s, 1H), 4.05 (m, 1H), 2.70 (m, 2H), 2.55 (m, 2H), 2.40 (m, 2H), 2.25 (m, 2H).

Step C: N-({1-[4-(4-Methyl-pyrazol-1-yl)-cyclohexyl]-azetidin-3-ylcarbamoyl}-methyl)-3-trifluoromethyl-benzamide

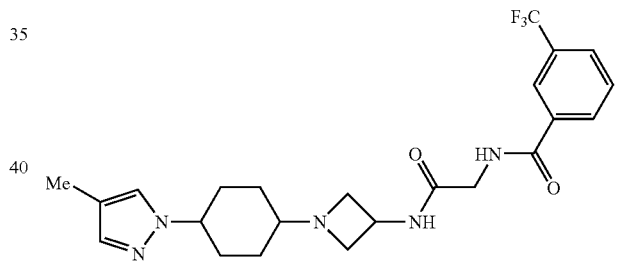

The title compounds were prepared as white solids from the reductive amination of 4-(4-methyl-pyrazol-1-yl)-cyclohexanone (as prepared in the previous step) and N-(azetidin-3-ylcarbamoylmethyl)-3-trifluoromethyl-benzamide (as prepared in Example 2 Step C) using the procedure described in Step D of Example 1.

27a: Less Polar Fraction from Silica Gel Column, $^1$H NMR (400 MHz, CDCl$_3$) δ 8.11 (s, 1H), 8.02 (d, J=6.5 Hz, 1H), 7.80 (t, J=6.5 Hz, 1H), 7.28 (s, 1H), 7.21 (s, 1H), 7.18 (m, 1H), 6.72 (d, J=6.5 Hz, 1H), 4.52 (m, 1H), 4.20 (s, 2H), 4.05 (m, 1H), 3.52 (t, J=6.5 Hz, 2H), 2.98 (t, J=6.5 Hz, 2H), 2.30 (m, 1H), 2.12 (m, 1H), 1.91 (m, 2H), 1.75 (m, 2H), 1.56 (m, 2H).

27b: More Polar Fraction from Silica Gel Column $^1$H NMR (400 MHz, CDCl$_3$) δ 8.10 (s, 1H), 8.05 (d, J=6.5 Hz, 1H), 7.75 (d, J=6.0 Hz, 1H), 7.60 (t, J=5.8 Hz, 1H), 7.30 (s, 1H), 7.20 (s, 2H), 6.82 (d, J=4.5 Hz, 1H), 4.65 (m, 1H), 4.20 (m, 2H), 4.02 (m, 1H), 3.65 (t, J=6.5 Hz, 2H), 3.02 (t, J=6.5 Hz, 2H), 2.35 (m, 1H), 2.20 (m, 2H), 1.95 (m, 2H), 1.70 (m, 2H), 1.25 (m, 2H).

Example 28

N-({1-[4-(4-Iodo-pyrazol-1-yl)-cyclohexyl]-azetidin-3-ylcarbamoyl}-methyl)-3-trifluoromethyl-benzamide Step A: 4-iodo-1-(1,4-dioxa-spiro[4.5]dec-8-yl)-1H-pyrazole

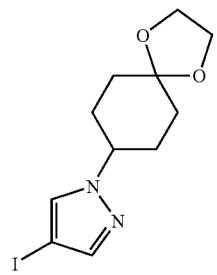

The title compound was prepared as a white solid from 4-iodo-pyrazole (Aldrich) using the procedure described in Step B of Example 1.

¹H NMR (CHLOROFORM-d) δ: 7.49 (d, J=2.5 Hz, 2H), 4.22 (s, 1H), 3.90-4.00 (m, 4H), 1.98-2.20 (m, 4H), 1.82-1.95 (m, 2H), 1.73 (dd, J=13.1, 4.5 Hz, 2H).

Step B: 4-(4-Iodo-pyrazol-1-yl)-cyclohexanone

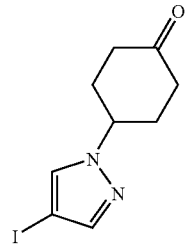

The title compound was prepared as a white solid from the de-protection of 4-iodo-1-(1,4-dioxa-spiro[4.5]dec-8-yl)-1H-pyrazole (as prepared in the previous step) using the procedure described in Step C of Example 1.

¹H NMR (CHLOROFORM-d) δ: 7.53 (d, J=6.3 Hz, 2H), 4.61 (tt, J=10.1, 4.0 Hz, 1H), 2.47-2.65 (m, 4H), 2.37-2.46 (m, 2H), 2.20-2.35 (m, 2H).

Step C: N-({1-[4-(4-Iodo-pyrazol-1-yl)-cyclohexyl]-azetidin-3-ylcarbamoyl}-methyl)-3-trifluoromethyl-benzamide

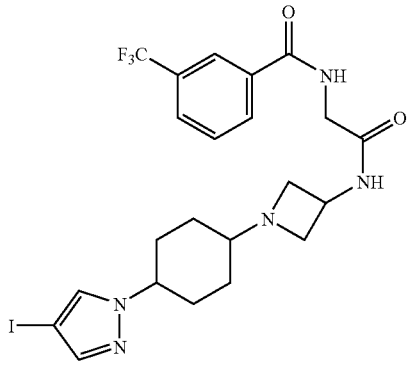

The title compounds were prepared as white solids from the reductive amination of 4-(4-iodo-pyrazol-1-yl)-cyclohexanone (as prepared in the previous step) and N-(azetidin-3-ylcarbamoylmethyl)-3-trifluoromethyl-benzamide (as prepared in Example 2 Step C) using the procedure described in Step D of Example 1.

¹H NMR (MeOH) δ: 8.21 (s, 1H), 8.13 (d, J=7.8 Hz, 1H), 7.86 (d, J=7.8 Hz, 1H), 7.79 (s, 1H), 7.66-7.75 (m, 1H), 7.46 (s, 1H), 4.45 (quin, J=6.9 Hz, 1H), 4.15-4.29 (m, 1H), 3.88 (t, J=7.7 Hz, 2H), 3.64 (t, J=7.6 Hz, 2H), 2.96 (t, J=7.3 Hz, 2H), 2.32-2.43 (m, 1H), 2.02-2.28 (m, 2H), 1.75-1.88 (m, 2H), 1.45-1.74 (m, 4H).

Example 29

3-Trifluoromethyl-N-({1-[4-(4-trimethylsilanylethynyl-pyrazol-1-yl)-cyclohexyl]-azetidin-3-ylcarbamoyl}-methyl)-benzamide

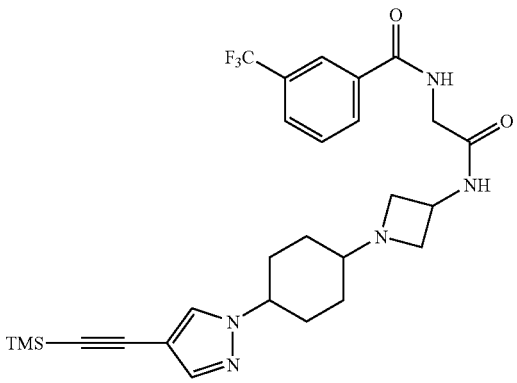

A solution of N-({1-[4-(4-Iodo-pyrazol-1-yl)-cyclohexyl]-azetidin-3-ylcarbamoyl}-methyl)-3-trifluoromethyl-benzamide (as prepared in Example 28, 120 mg, 0.20 mmol), TMS-acetylene (Fluka, 20 mg, 0.40 mmol), Pd(Cl₂)dppf (Aldrich, 16 mg, 0.02 mmol), CuI (Aldrich, 3.8 mg, 0.02 mmol) and Et₃N (56 uL, 0.40 mmol) in DMF (5 mL) was heated to 80° C. overnight. The reaction was purified column chromatography purification (0-100% ethyl acetate in hexanes with NH₃ in MeOH) resulting in the title compound as a white solid.

29a: Less Polar Fraction from Silica Gel Column,

¹H NMR (MeOH) δ: 8.03 (s, 1H), 7.95 (d, J=7.8 Hz, 1H), 7.61-7.73 (m, 2H), 7.50 (t, J=7.8 Hz, 1H), 7.35-7.44 (m, 1H), 4.26 (t, J=6.8 Hz, 1H), 3.95-4.05 (m, 1H), 3.91 (q, J=7.1 Hz, 2H), 3.45 (t, J=7.6 Hz, 2H), 2.77 (t, J=7.5 Hz, 2H), 2.14-2.25 (m, 1H), 1.90-2.06 (m, 2H), 1.58-1.69 (m, 2H), 1.33-1.53 (m, 4H), −0.01 (s, 9H).

29b: More Polar Fraction from Silica Gel Column

¹H NMR (MeOH) δ: 8.04 (s, 1H), 7.97 (d, J=7.8 Hz, 1H), 7.77 (s, 1H), 7.68 (d, J=7.8 Hz, 1H), 7.51 (t, J=7.8 Hz, 1H), 7.39 (s, 1H), 4.13 (br. s., 1H), 3.75 (d, J=14.7 Hz, 2H), 3.49 (t, J=11.2 Hz, 2H), 3.29-3.40 (m, 2H), 2.26 (s, 1H), 1.82 (s, 1H), 1.75 (br. s., 2H), 1.54-1.66 (m, 2H), 1.51 (br. s., 2H), 1.42 (d, J=14.4 Hz, 2H), 0.00 (s, 9H).

Example 30

N-({1-[4-(4-Ethynyl-pyrazol-1-yl)-cyclohexyl]-azetidin-3-ylcarbamoyl}-methyl)-3-trifluoromethyl-benzamide

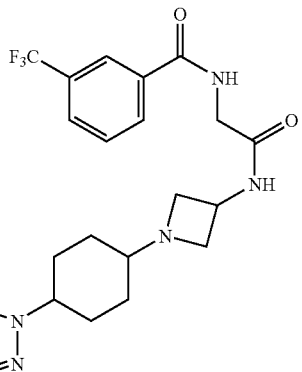

To a solution of 3-Trifluoromethyl-N-({1-[4-(4-trimethylsilanylethynyl-pyrazol-1-yl)-cyclohexyl]-azetidin-3-ylcarbamoyl}-methyl)-benzamide (as prepared in Example 29, 52.5 mg, 0.09 mmol) in THF (4 mL) was added TBAF (Aldrich, 47 mg, 0.18 mmol) and the reaction was stirred at RT over night followed by column chromatography purification (0-100% ethyl acetate in hexanes with 7N $NH_3$ in MeOH) resulting in the title compound as a white solid.

30a: Less Polar Fraction from Silica Gel Column,
$^1$H NMR (MeOH) δ: 8.24 (br. s., 1H), 8.16 (d, J=7.6 Hz, 1H), 7.81-7.95 (m, 1H), 7.71 (t, J=7.6 Hz, 1H), 7.48-7.64 (m, 2H), 4.47 (t, J=6.8 Hz, 1H), 4.20 (t, J=8.3 Hz, 2H), 3.66 (t, J=6.8 Hz, 2H), 3.32 (br s, 1H), 2.97 (t, J=6.8 Hz, 2H), 2.51 (br s, 1H), 2.38 (br. s., 1H), 2.20 (d, J=10.4 Hz, 2H), 1.79-1.88 (m, 2H), 1.53-1.75 (m, 4H).

30b: More Polar Fraction from Silica Gel Column
$^1$H NMR (MeOH) δ: 8.14 (s, 1H), 8.06 (d, J=7.8 Hz, 1H), 7.88 (s, 1H), 7.77 (d, J=7.6 Hz, 1H), 7.60 (t, J=8.1 Hz, 1H), 7.49 (s, 1H), 4.19-4.29 (m, 1H), 3.54-3.67 (m, 2H), 3.43 (d, J=10.4 Hz, 2H), 3.31 (br s, 1H), 3.24-3.28 (m, 2H), 2.55 (br s., 1H), 2.34-2.46 (m, 2H), 1.84-1.96 (m, 2H), 1.66-1.78 (m, 2H), 1.40-1.64 (m, 2H).

Example 31

N-{[1-(4-Hydroxy-4-imidazol-1-yl-cyclohexyl)-azetidin-3-ylcarbamoyl]-methyl}-3-trifluoromethyl-benzamide

Step A:
1-(1,4-Dioxa-spiro[4.5]dec-8-yl)-1H-imidazole

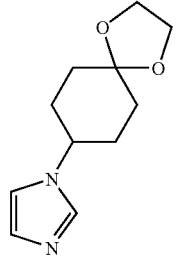

To a solution of imidazole (Aldrich, 10.0 g, 14.6 mmol) in DMF (20 mL) at 0° C. was added NaH (Aldrich, 60% in mineral oil 300 mg) and reaction was warmed to RT followed by heating to 100° C. overnight in a flask fitted with a reflux condenser. The reaction was cooled and poured over ice and extracted with EtOAc and washed with water. The organic layer was dried ($Na_2SO_4$) and concentrated in vacuo followed by column chromatography purification (0-50% Ethyl Acetate in Hexanes with $NH_3$ in MeOH) resulting in the title compound as a yellow oil.

$^1$H NMR (MeOH) δ: 7.76 (s, 1H), 7.21 (s, 1H), 6.99 (s, 1H), 3.98 (d, J=6.1 Hz, 4H), 2.00-2.14 (m, 4H), 1.87 (d, J=14.1 Hz, 2H), 1.69-1.82 (m, 2H).

Step B: 4-Imidazol-1-yl-cyclohexanone

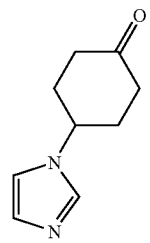

The title compound was prepared as a white solid from the de-protection of 1-(1,4-dioxa-spiro[4.5]dec-8-yl)-1H-imidazole (as prepared in the previous step) using the procedure described in Step C of Example 1.

$^1$H NMR (MeOH) δ: 8.87 (s, 1H), 7.62 (s, 1H), 7.45 (s, 1H), 2.38 (d, J=13.1 Hz, 1H), 2.02 (br. s., 2H), 1.95 (br. s., 2H), 1.76-1.94 (m, 2H), 1.53-1.74 (m, 2H)

Step C: N-{[1-(4-Imidazol-1-yl-cyclohexyl)-azetidin-3-ylcarbamoyl]-methyl}-3-trifluoromethyl-benzamide

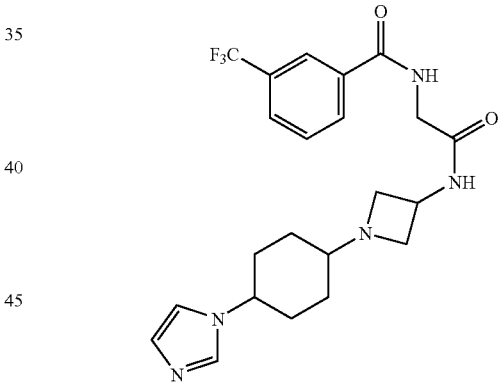

The title compounds were prepared as white solids from the reductive amination of 4-imidazol-1-yl-cyclohexanone (as prepared in the previous step) and N-(azetidin-3-ylcarbamoylmethyl)-3-trifluoromethyl-benzamide (as prepared in Example 2 Step C) using the procedure described in Step D of Example 1.

31a: Less Polar Fraction from Silica Gel Column,
$^1$H NMR (MeOH) δ: 8.24 (s, 1H), 8.16 (d, J=7.8 Hz, 1H), 7.88 (d, J=7.8 Hz, 1H), 7.66-7.78 (m, 2H), 7.23 (s, 1H), 6.97 (s, 1H), 4.50 (t, J=7.1 Hz, 1H), 4.12 (q, J=7.1 Hz, 2H), 3.70 (t, J=7.7 Hz, 2H), 2.98 (t, J=7.7 Hz, 2H), 2.43 (t, J=3.4 Hz, 1H), 2.05-2.22 (m, 2H), 1.70-1.84 (m, 4H), 1.51-1.67 (m, 2H).

31b: More Polar Fraction from Silica Gel Column
$^1$H NMR (MeOH) δ: 8.24 (s, 1H), 8.17 (d, J=7.8 Hz, 1H), 7.83-7.97 (m, 1H), 7.70 (s, 1H), 7.74 (s, 1H), 7.33 (s, 1H), 7.07 (s, 1H), 4.88 (br s., 12H), 4.56 (t, J=7.3 Hz, 2H), 3.63 (t, J=7.1 Hz, 2H), 3.12-3.26 (m, 1H), 2.75 (br. s., 1H), 2.05-2.24 (m, 2H), 1.81-1.91 (m, 4H), 1.78 (br. s., 2H), 1.54-1.74 (m, 2H).

Example 32

N-{[1-(4-Indazol-1-yl-cyclohexyl)-azetidin-3-ylcarbamoyl]-methyl}-3-trifluoromethyl-benzamide
Step A: 1-(1,4-Dioxa-spiro[4.5]dec-8-yl)-1H-indazole

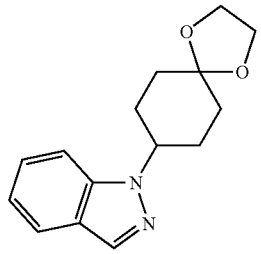

The title compound was prepared as a white solid from indane (Aldrich) using the procedure described in Step A of Example 31.

$^1$H NMR (CHLOROFORM-d) δ: 7.99 (s, 1H), 7.73 (d, J=8.1 Hz, 1H), 7.44-7.52 (m, 1H), 7.36 (ddd, J=8.3, 6.9, 1.1 Hz, 1H), 7.13 (t, J=7.1 Hz, 1H), 4.53 (s, 1H), 3.92-4.05 (m, 4H), 2.32-2.53 (m, 2H), 2.01-2.17 (m, 2H), 1.91-2.01 (m, 2H), 1.70-1.89 (m, 2H).

Step B: 4-Indazol-1-yl-cyclohexanone

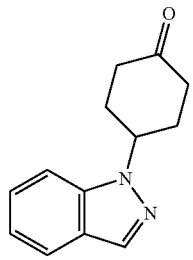

The title compound was prepared as a white solid from the de-protection of 1-(1,4-dioxa-spiro[4.5]dec-8-yl)-1H-indazole (as prepared in the previous step) using the procedure described in Step C of Example 1.

$^1$H NMR (CHLOROFORM-d) δ: 8.02 (s, 1H), 7.76 (d, J=8.1 Hz, 1H), 7.45-7.54 (m, 1H), 7.37-7.44 (m, 1H), 7.18 (t, J=7.5 Hz, 1H), 4.92 (dt, J=9.0, 4.5 Hz, 1H), 2.66-2.78 (m, 2H), 2.50-2.64 (m, 4H), 2.31-2.44 (m, 2H).

Step C: N-{[1-(4-Indazol-1-yl-cyclohexyl)-azetidin-3-ylcarbamoyl]-methyl}-3-trifluoromethyl-benzamide

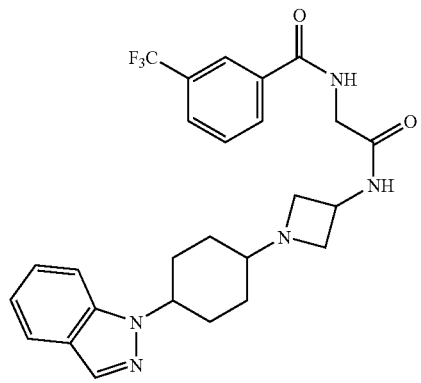

The title compounds were prepared as white solids from the reductive amination of 4-indazol-1-yl-cyclohexanone (as prepared in the previous step) and N-(azetidin-3-ylcarbamoylmethyl)-3-trifluoromethyl-benzamide (as prepared in Example 2 Step C) using the procedure described in Step D of Example 1.

32a: Less Polar Fraction from Silica Gel Column,
$^1$H NMR (CHLOROFORM-d) δ: 8.13 (s, 1H), 7.96-8.07 (m, 1H), 7.78 (d, J=7.8 Hz, 1H), 7.73 (d, J=8.1 Hz, 1H), 7.52-7.63 (m, 1H), 7.45 (d, J=7.8 Hz, 1H), 7.31-7.41 (m, 1H), 7.06-7.16 (m, 1H), 6.66 (d, J=8.1 Hz, 1H), 4.55 (q, J=6.8 Hz, 1H), 4.36-4.49 (m, 1H), 4.20 (d, J=4.8 Hz, 2H), 3.58 (t, J=7.3 Hz, 2H), 2.89-3.07 (m, 2H), 2.32-2.52 (m, 1H), 1.82 (br. s., 4H), 1.74 (d, J=13.1 Hz, 2H), 1.55 (t, J=13.4 Hz, 2H).

32b: More Polar Fraction from Silica Gel Column
$^1$H NMR (CHLOROFORM-d) δ: 8.12 (d, J=8.3 Hz, 1H), 8.01 (s, 1H), 7.71-7.83 (m, 2H), 7.56-7.65 (m, 1H), 7.41-7.49 (m, 1H), 7.37 (d, J=7.8 Hz, 1H), 7.08-7.19 (m, 1H), 6.57-6.72 (m, 1H), 4.51-4.61 (m, 1H), 4.38-4.49 (m, 1H), 4.19 (d, J=4.8 Hz, 2H), 3.58 (t, J=7.3 Hz, 2H), 2.85-3.07 (m, 2H), 2.32-2.53 (m, 1H), 1.83 (d, J=10.9 Hz, 2H), 1.76 (br. s., 2H), 1.57 (t, J=14.0 Hz, 2H), 1.20-1.43 (m, 2H).

Example 33

N-({1-[4-(Benzo[1,3]dioxol-5-yloxy)-cyclohexyl]-azetidin-3-ylcarbamoyl}-methyl)-3-trifluoromethyl-benzamide

Step A: 5-(1,4-Dioxa-spiro[4.5]dec-8-yloxy)-benzo[1,3]dioxole

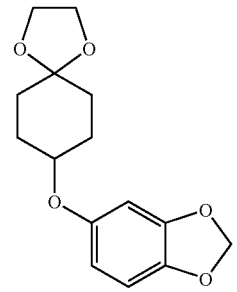

The title compound was prepared as a white solid from sesamol (Aldrich) using the procedure described in Step A of Example 31.

$^1$H NMR (CHLOROFORM-d) δ: 6.53-6.68 (m, 1H), 6.40 (dd, J=7.5, 2.4 Hz, 1H), 6.16-6.31 (m, 1H), 5.57-5.69 (m, 2H), 5.52 (d, J=11.9 Hz, 1H), 3.89 (s, 4H), 2.10-2.26 (m, 4H), 1.81 (d, J=3.0 Hz, 2H), 1.67 (t, J=6.6 Hz, 2H).

Step B: 4-(Benzo[1,3]dioxol-5-yloxy)-cyclohexanone

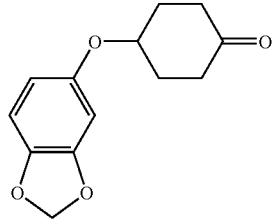

The title compound was prepared as a white solid from the de-protection of 5-(1,4-dioxa-spiro[4.5]dec-8-yloxy)-benzo[1,3]dioxole (as prepared in the previous step) using the procedure described in Step C of Example 1.

ESI-MS (m/z): Calcd. For $C_{13}H_{14}O_4$: 234.09; found: 235.01 (M+H).

Step C: N-({1-[4-(Benzo[1,3]dioxol-5-yloxy)-cyclohexyl]azetidin-3-ylcarbamoyl}-methyl)-3-trifluoromethyl-benzamide

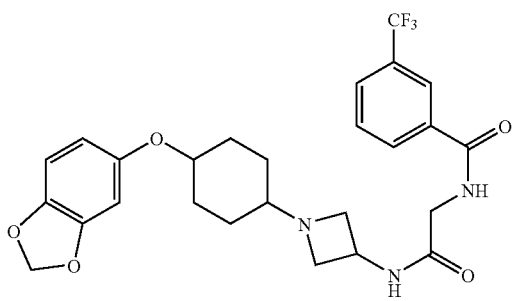

The title compounds were prepared as white solids from the reductive amination of 4-(benzo[1,3]dioxol-5-yloxy)-cyclohexanone (as prepared in the previous step) and N-(azetidin-3-ylcarbamoylmethyl)-3-trifluoromethyl-benzamide (as prepared in Example 2 Step C) using the procedure described in Step D of Example 1.

$^1$H NMR (MeOH) δ: 8.24 (s, 1H), 8.16 (d, J=7.8 Hz, 1H), 7.88 (d, J=8.1 Hz, 1H), 7.64-7.77 (m, 2H), 6.52 (d, J=7.6 Hz, 1H), 6.37 (t, J=8.3 Hz, 1H), 5.88 (s, 2H), 4.48 (t, J=7.1 Hz, 1H), 4.05 (br s., 2H), 3.68 (t, J=7.5 Hz, 2H), 2.90-3.11 (m, 2H), 2.51 (br s., 1H), 2.19 (d, J=10.6 Hz, 2H), 2.10 (d, J=13.1 Hz, 2H), 2.00 (d, J=12.9 Hz, 2H), 1.87 (d, J=10.9 Hz, 2H).

Example 34

N-({1-[4-(Benzo[d]isothiazol-3-yloxy)-cyclohexyl]-azetidin-3-ylcarbamoyl}-methyl)-3-trifluoromethyl-benzamide Step A: 3-(1,4-Dioxa-spiro[4.5]dec-8-yloxy)-benzo[d]isothiazole

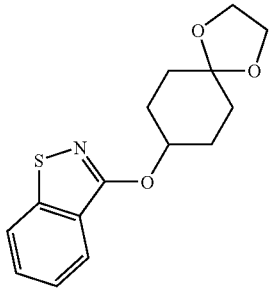

The title compound was prepared as a white solid from 1,2-benzisothiazole-3-one (Aldrich) using the procedure described in Step B of Example 1.

$^1$H NMR (CHLOROFORM-d) δ: 7.88 (d, J=8.1 Hz, 1H), 7.73 (d, J=8.3 Hz, 1H), 7.47 (t, J=7.2 Hz, 1H), 7.30-7.39 (m, 1H), 5.29 (t, J=5.2 Hz, 1H), 3.79-4.04 (m, 4H), 2.04-2.15 (m, 4H), 1.91-2.02 (m, 2H), 1.66-1.77 (m, 2H).

Step B: 4-(Benzo[d]isothiazol-3-yloxy)-cyclohexanone

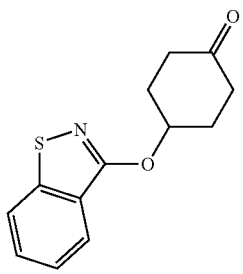

The title compound was prepared as a white solid from the de-protection of 3-(1,4-dioxa-spiro[4.5]dec-8-yloxy)-benzo[d]isothiazole (as prepared in the previous step) using the procedure described in Step C of Example 1.

$^1$H NMR (CHLOROFORM-d) δ: 7.92 (d, J=8.1 Hz, 1H), 7.79 (d, J=8.1 Hz, 1H), 7.53 (td, J=7.6, 1.1 Hz, 1H), 7.40 (t, J=8.0 Hz, 1H), 5.53-5.62 (m, J=5.6, 3.1, 3.1, 3.1, 3.1 Hz, 1H), 2.52-2.77 (m, 2H), 2.34-2.51 (m, 4H), 2.21-2.34 (m, 2H).

Step C: N-({1-[4-(Benzo[d]isothiazol-3-yloxy)-cyclohexyl]azetidin-3-ylcarbamoyl}-methyl)-3-trifluoromethyl-benzamide

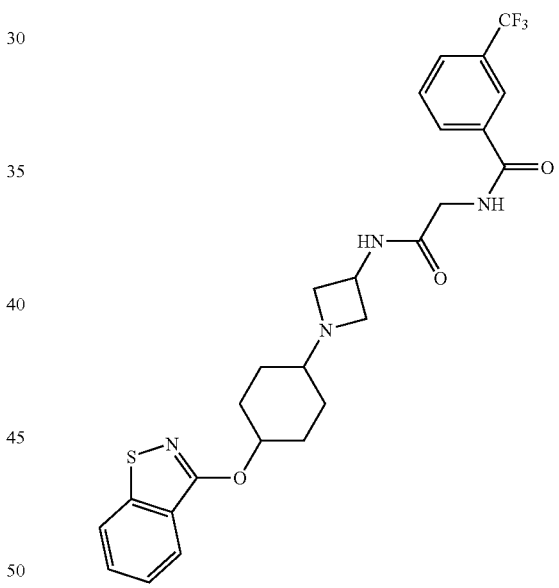

The title compounds were prepared as white solids from the reductive amination of 4-(benzo[d]isothiazol-3-yloxy)-cyclohexanone (as prepared in the previous step) and N-(azetidin-3-ylcarbamoylmethyl)-3-trifluoromethyl-benzamide (as prepared in Example 2 Step C) using the procedure described in Step D of Example 1.

34a: Less Polar Fraction from Silica Gel Column, $^1$H NMR (MeOH) δ: 8.24 (s, 1H), 8.15 (d, J=7.8 Hz, 1H), 7.78-7.85 (m, 3H), 7.66 (t, J=7.8 Hz, 1H), 7.46-7.58 (m, 1H), 7.32-7.43 (m, 1H), 4.66 (br s., 1H), 4.42-4.57 (m, 2H), 4.08-4.01 (m, 2H), 3.64-3.81 (m, 2H), 3.08-3.24 (m, 1H), 2.27 (d, J=8.3 Hz, 2H), 2.18 (d, J=14.1 Hz, 2H), 1.88 (d, J=10.9 Hz, 2H), 1.64 (br. s., 2H), 1.45-1.58 (m, 2H).

34b: More Polar Fraction from Silica Gel Column

¹H NMR (MeOH) δ: 8.24 (s, 1H), 8.15 (d, J=7.8 Hz, 1H), 7.77-7.86 (m, 3H), 7.66 (t, J=7.8 Hz, 1H), 7.46-7.57 (m, 1H), 7.37 (td, J=7.5, 4.3 Hz, 1H), 4.41-4.60 (m, 1H), 4.08 (br s., 1H), 3.68-3.81 (m, 2H), 3.37-3.44 (m, 2H), 2.27 (d, J=3.5 Hz, 2H), 2.18 (d, J=10.9 Hz, 1H), 1.88 (d, J=10.9 Hz, 2H), 1.59-1.73 (m, 2H), 1.45-1.59 (m, 2H), 1.13-1.26 (m, 2H).

Example 35

Benzo[1,3]dioxole-5-carboxylic acid (4-{3-[2-(3-trifluoromethyl-benzoylamino)-acetylamino]-azetidin-1-yl}-cyclohexyl)-amide Step A: {4-{3-[2-(3-Trifluoromethyl-benzoylamino)-acetylamino]-azetidin-1-yl}-cyclohexyl)-carbamic acid tert-butyl ester The title compounds were prepared as white solids from the reductive amination of (4-oxo-cyclohexyl)-carbamic acid tert-butyl ester (Asta) and N-(azetidin-3-ylcarbamoylmethyl)-3-trifluoromethyl-benzamide (as prepared in Example 2 Step C) using the procedure described in Step D of Example 1.

Less Polar Fraction from Silica Gel Column
¹H NMR (400 MHz, CDCl₃) δ 8.15 (s, 1H), 8.02 (d, J=6.5 Hz, 1H), 7.80 (d, J=6.4 Hz, 1H), 7.78 (s, br, 1H), 7.62 (t, J=6.5 Hz, 1H), 7.38 (s, 1H), 4.72 (s, br, 1H), 4.48 (m, 1H), 4.15 (s, 2H), 3.60 (m, 2H), 2.92 (t, J=4.5 Hz, 2H), 2.35 (m, 2H), 2.06 (m, 1H), 1.65 (m, 4H), 1.45 (s, 9H), 1.35 (m, 2H).

Step B: N-{[1-(4-Amino-cyclohexyl)-azetidin-3-ylcarbamoyl]-methyl}-3-trifluoromethyl-benzamide TFA salt

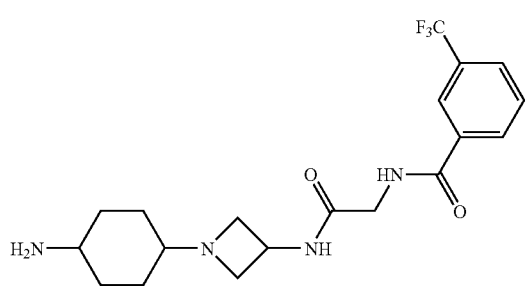

A solution of {4-{3-[2-(3-trifluoromethyl-benzoylamino)-acetylamino]-azetidin-1-yl}-cyclohexyl)-carbamic acid tert-butyl ester (less polar isomer, as prepared in the previous step 5.6 g, 11.2 mmol) in DCM 10 mL and TFA (10 mL) was stirred for 4 hours at room temperature. The solvent was removed and the residue was dried in vacuo to afford the title compound as colorless oil.

ESI-MS (m/z): Calcd. For $C_{19}H_{25}F_3N_4O_2$, 398; found: 399 (M+H).

Step C: Benzo[1,3]dioxole-5-carboxylic acid (4-{3-[2-(3-trifluoromethyl-benzoylamino)-acetylamino]-azetidin-1-yl}-cyclohexyl)-amide

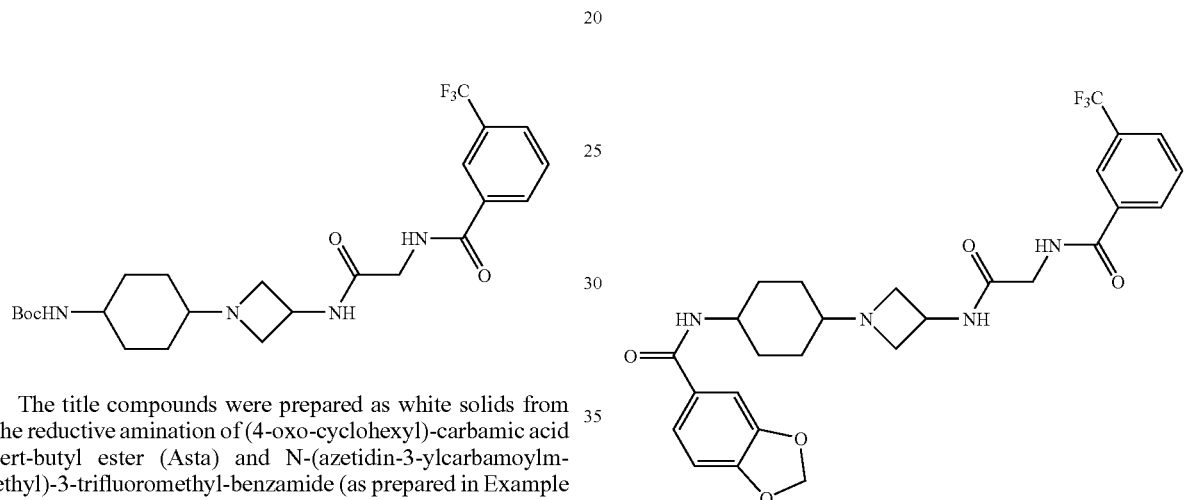

Benzo[1,3]dioxole-5-carbonyl chloride (Aldrich, 74 mg, 0.404 mmol) was added into a solution of N-{[1-(4-amino-cyclohexyl)-azetidin-3-ylcarbamoyl]-methyl}-3-trifluoromethyl-benzamide TFA salt (as prepared in the previous step 200 mg, 0.404 mmol) and TEA (170 µL, 1.21 mmol) in DCM (5 mL) at 0° C. The reaction was stirred for an additional 2 hours and quenched with saturated sodium bicarbonate. The reaction was then partitioned between DCM and water. The organic layer was separated and the aqueous layer was extracted 3 times with a chloroform/IPA "cocktail" (~3:1, v/v). The combined organic layer was dried over anhydrous $Na_2SO_4$, filtered and concentrated to give the crude product, which was then purified by a CombiFlash® system using ethyl acetate and 7N $NH_3$ in MeOH as eluent (from pure ethyl acetate to 5% 7N $NH_3$ in MeOH in ethyl acetate) to afford the title compound as white solid.

¹H NMR (400 MHz, d₄-MeOH) δ 8.11 (s, 1H), 8.05 (d, J=6.0 Hz, 1H), 7.78 (d, J=6.0 Hz, 1H), 7.63 (t, J=7.2 Hz, 1H), 7.26 (d, J=4.2 Hz, 1H), 7.20 (s, 1H), 6.82 (d, J=6.5 Hz, 1H), 5.95 (s, 1H), 4.35 (m, 1H), 3.95 (s, 2H), 3.84 (m, 1H), 3.68 (t, J=7.5 Hz, 2H), 2.98 (t, J=7.2 Hz, 2H), 2.25 (m, 1H), 1.70 (m, 2H), 1.55 (m, 6H).

Example 36

N-({1-[4-(3-Benzo[1,3]dioxol-5-yl-ureido)-cyclohexyl]-azetidin-3-ylcarbamoyl}-methyl)-3-trifluoromethyl-benzamide

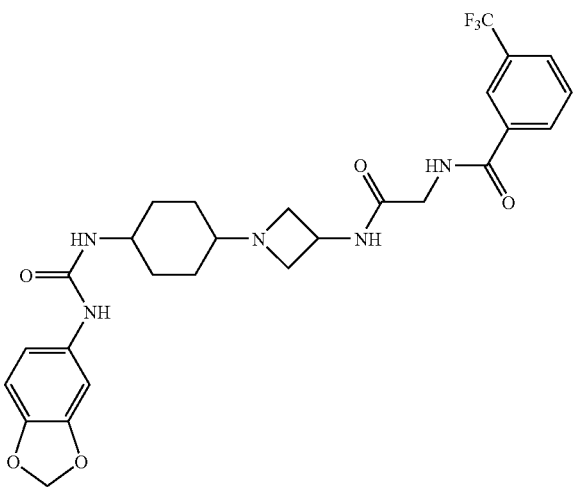

5-Isocyanato-benzo[1,3]dioxole (Aldrich, 50 mg, 0.302 mmol) was added into a solution of N-{[1-(4-amino-cyclohexyl)-azetidin-3-ylcarbamoyl]-methyl}-3-trifluoromethyl-benzamide TFA salt (150 mg, 0.302 mmol) and TEA (127 µL, 0.906 mmol) in DMF (3 mL) at room temperature. The reaction was stirred overnight and quenched with saturated sodium bicarbonate. The reaction was then partitioned between DCM and water. The organic layer was separated and the aqueous layer was extracted 3 times with a chloroform/IPA "cocktail" (~3:1, v/v). The combined organic layers were dried over anhydrous Na$_2$SO$_4$, filtered and concentrated to give the crude product, which was then purified by a CombiFlash® system using ethyl acetate and 7N NH$_3$ in MeOH as eluent (from pure ethyl acetate to 5% 7N NH$_3$ in MeOH in ethyl acetate) to afford the title compound as white solid.

$^1$H NMR (400 MHz, d$_4$-MeOH) δ 8.11 (s, 1H), 8.05 (d, J=6.5 Hz, 1H), 7.80 (d, J=6.0 Hz, 1H), 7.62 (t, J=7.2 Hz, 1H), 6.95 (s, 1H), 6.63 (d, J=6.2 Hz, 1H), 6.45 (d, J=6.5 Hz, 1H), 5.80 (s, 2H), 4.35 (m, 1H), 3.98 (s, 2H), 3.65 (m, 1H), 3.60 (t, J=7.5 Hz, 2H), 2.95 (t, J=7.2 Hz, 2H), 2.15 (m, 1H), 1.60 (m, 2H), 1.45 (m, 4H), 1.22 (m, 2H).

Example 37

N-({1-[4-(2,5-Dimethyl-pyrrol-1-yl)-cyclohexyl]-azetidin-3-ylcarbamoyl}-methyl)-3-trifluoromethyl-benzamide

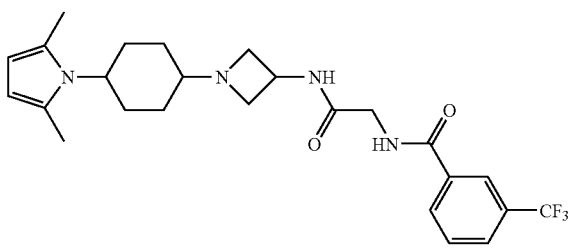

To a solution of N-{[1-(4-amino-cyclohexyl)-azetidin-3-ylcarbamoyl]-methyl}-3-trifluoromethyl-benzamide trifluoroacetic acid salt (as prepared in Example 35 Step B, 0.24 g, 0.4 mmol) in methanol (2 mL) was added DIEA (Aldrich, 0.21 mL, 1.2 mmol) and acetonylacetone (Aldrich, 0.06 mL, 0.5 mmol). The resulting mixture was stirred at rt overnight and the volatile organics were removed by evaporation. The residue was dissolved in water, extracted with EtOAc, dried over Na$_2$SO$_4$. Filtration and evaporation gave a crude product, which was purified by column chromatography (eluent: EtOAc) to give the cis isomer as a white solid.

$^1$H NMR (400 MHz, CDCl$_3$): δ 8.13 (1H, s), 8.00-8.02 (1H, d), 7.79-7.81 (1H, d), 7.58-7.62 (1H, t), 2.23-7.27 (1H, m), 6.72-6.74 (1H, d), 5.73 (2H, s), 4.53-4.58 (1H, m), 4.17-4.18 (2H, d), 3.84-3.90 (1H, m), 3.61-3.65 (2H, m), 2.81-2.85 (2H, m), 2.25-2.35 (8H, m), 1.37-1.77 (6H, m). LC/MS: 477.2 [M+H].

Example 38

Step A:

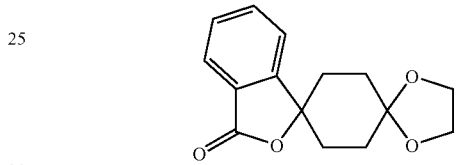

Iso-propyl-magnesium bromide (Aldrich, 2.0 M in THF, 10 mL, 20 mmol) was slowly dropped into a solution of 2-iodo-benzoic acid methyl ester (Aldrich, 5.00 g, 19.2 mmol) in THF (20 mL) at 0° C. After addition, the reaction was stirred for another 30 min. A solution of 1,4-dioxa-spiro[4.5]decan-8-one (Aldrich, 3.00 g, 19.2 mmol) in THF (10 mL) was added to the reaction mixture at 0° C. The reaction was stirred for an additional 2 hours, quenched with saturated NH$_4$Cl solution and warmed to room temperature. The solvent was removed in vacuo and the residue was partitioned between ethyl acetate and water. The organic layer was washed with brine, dried over anhydrous Na$_2$SO$_4$, filtered and concentrated to give a yellow solid, which was then purified by silica gel column on a CombiFlash® system using hexanes and ethyl acetate (from 10% ethyl acetate to 100% ethyl acetate) to afford the title compound as white solid.

$^1$H NMR (400 MHz, CDCl$_3$) δ 7.89 (d, J=6.3 Hz, 1H), 7.66 (t, J=6.0 Hz, 1H), 7.48 (t, J=6.2 Hz, 1H), 7.42 (d, J=6.0 Hz, 1H), 4.05 (s, 4H), 2.50 (m, 4H), 2.01 (m, 4H).

Step B:

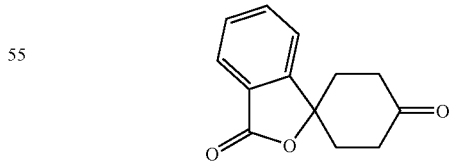

The title compound was prepared as a white solid from the de-protection of the product of Example 38, Step A using the procedure described in Step C of Example 1.

$^1$H NMR (400 MHz, CDCl$_3$) δ 7.95 (d, J=6.5 Hz, 1H), 7.70 (t, J=6.5 Hz, 1H), 7.55 (t, J=6.2 Hz, 1H), 7.41 (d, J=6.5 Hz, 1H), 2.98 (m, 2H), 2.46 (m, 2H), 2.40 (m, 2H), 2.15 (m, 2H).

Step C:

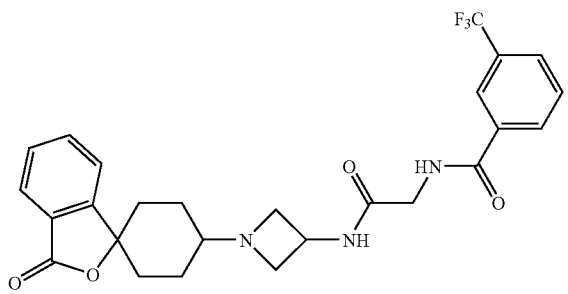

The title compounds were prepared as white solids from the reductive amination of the ketone prepared in Example 38 Step B and N-(azetidin-3-ylcarbamoylmethyl)-3-trifluoromethyl-benzamide (as prepared in Example 2 Step C) using the procedure described in Step D of Example 1.

38a: Less Polar Fraction from Silica Gel Column, $^1$H NMR (400 MHz, d$_4$-MeOH) δ 8.21 (s, 1H), 8.15 (d, J=6.5 Hz, 1H), 7.87 (m, 2H), 7.65 (m, 3H), 7.55 (t, J=7.2 Hz, 2H), 4.55 (m, 1H), 4.10 (s, 2H), 3.85 (t, J=7.5 Hz, 2H), 3.15 (t, J=7.2 Hz, 2H), 2.70 (m, 1H), 2.25 (m, 2H), 1.98 (m, 2H), 1.80 (m, 2H), 1.55 (m, 2H).

38b: More Polar Fraction from Silica Gel Column $^1$H NMR (400 MHz, d$_4$-MeOH) δ 8.25 (s, 1H), 8.18 (d, J=6.5 Hz, 1H), 7.90 (m, 2H), 7.70 (m, 3H), 7.60 (t, J=7.2 Hz, 2H), 4.58 (m, 1H), 4.08 (s, 2H), 3.80 (t, J=7.5 Hz, 2H), 3.20 (t, J=7.2 Hz, 2H), 3.01 (m, 1H), 2.35 (m, 1H), 2.28 (m, 1H0, 2.08 (m, 2H), 1.80 (m, 2H), 1.65 (m, 2H).

Example 39

Step A:

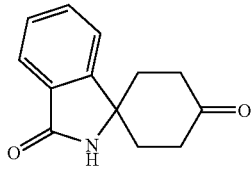

4-Oxo-1-phenyl-cyclohexanecarboxylic acid (Aldrich, 2.00 g, 9.17 mmol) was treated with DPPA (Aldrich, 18.3 mmol) and TEA (2.56 mL, 18.3 mmol) in toluene (10 mL) at reflux for 4 hours. After the reaction was cooled down to room temperature, 1 N HCl aqueous solution (~5 mL) and THF (5 mL) were added and the reaction was stirred overnight. The reaction was partitioned between saturated sodium bicarbonate and DCM. The organic layer was washed with brine, dried over anhydrous Na$_2$SO$_4$, filtered and concentrated to give yellow solid, which was then purified by silica gel column on a CombiFlash® system using hexanes and ethyl acetate (from 10% ethyl acetate to 100% ethyl acetate) to afford the product compound as white solid.

$^1$H NMR (400 MHz, CDCl$_3$) δ 7.30 (m, 4H), 6.56 (s, br, 1H), 2.98 (m, 2H), 2.80 (m, 2H), 2.64 (m, 2H), 2.45 (m, 2H).

Step B:

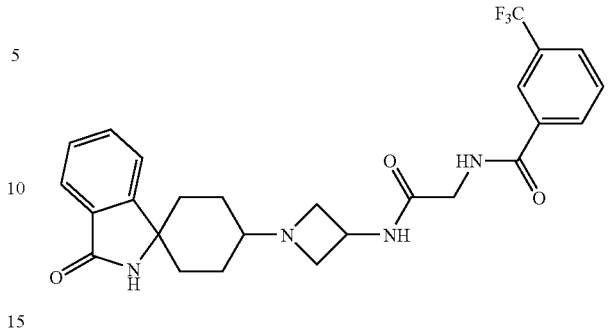

The title compounds were prepared as white solids from the reductive amination of the ketone in Example 39 Step A and N-(azetidin-3-ylcarbamoylmethyl)-3-trifluoromethyl-benzamide (as prepared in Example 2 Step C) using the procedure described in Step D of Example 1.

39a: Less Polar Isomer from Silica Gel Column, $^1$H NMR (400 MHz, CDCl$_3$) δ 8.18 (d, J=6.0 Hz, 1H), 8.10 (s, 1H), 8.02 (d, J=6.5 Hz, 1H), 7.75 (m, 1H), 7.70 (d, J=6.5 Hz, 1H), 7.55 (t, J=6.7 Hz, 1H), 7.35 (s, 1H), 7.25 (t, J=6.4 Hz, 1H), 6.47 (s, 1H), 4.45 (m, 1H), 4.20 (d, J=4.2 Hz, 2H), 3.49 (t, J=6.0 Hz, 2H), 3.25 (dd, J=9.5, 3.0 Hz, 2H), 2.45 (m, 2H), 2.35 (s, br, 1H), 2.30 (dd, J=9.0, 3.5 Hz, 2H), 1.95 (m, 2H), 1.55 (m, 2H).

39b: More Polar Isomer from Silica Gel Column $^1$H NMR (400 MHz, d$_4$-MeOH) δ 8.15 (s, 1H), 8.02 (d, J=6.0 Hz, 1H), 7.78 (d, J=6.5 Hz, 1H), 7.62 (t, J=6.4 Hz, 1H), 7.25 (m, 3H), 7.20 (m, 1H), 4.35 (m, 1H), 3.95 (s, 2H), 3.58 (t, J=4.5 Hz, 1H), 3.45 (t, J=4.2 Hz, 1H), 3.02 (m, 2H), 2.43 (m, 2H), 2.15 (m, 1H), 2.02 (m, 2H), 1.85 (d, J=7.0 Hz, 2H), 1.78 (m, 1H), 1.35 (m, 1H).

Example 40

Step A:

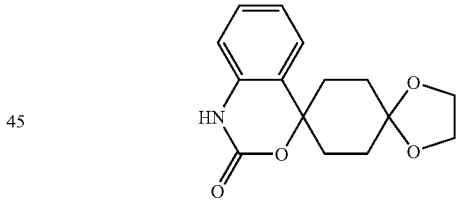

n-BuLi (2.5 N in hexanes, 19 mL, 46 mmol) was slowly dropped into a solution of (2-bromo-phenyl)-carbamic acid tert-butyl ester (Aldrich, 5.00 g, 18.5 mmol) in THF (25 mL) at −78° C. After addition, the reaction was stirred for another 30 min. A solution of 1,4-dioxa-spiro[4.5]decan-8-one (Aldrich, 2.89 g, 18.5 mmol) in THF (10 mL) was added into the reaction mixture at −78° C. The reaction was stirred for an additional 2 hours and warmed to room temperature. Solid t-BuOK (Aldrich, ~4 g, 37 mmol) was added, and the reaction was stirred overnight. The reaction was then quenched with saturated NH$_4$Cl solution. The solvent was removed in vacuo and the residue was partitioned between ethyl acetate and water. The organic layer was washed with brine, dried over anhydrous Na$_2$SO$_4$, filtered and concentrated to give a yellow solid, which was then purified by silica gel column on a CombiFlash® system using hexanes and ethyl acetate (from 10% ethyl acetate to 100% ethyl acetate) to afford the product compound as a white solid.

¹H NMR (400 MHz, CDCl₃) δ 9.45 (s, br, 1H), 7.25 (dt, J=7.0, 3.2 Hz, 1H), 7.20 (d, J=6.5 Hz, 1H), 7.05 (dt, J=7.0, 3.0 Hz, 1H), 6.90 (d, J=6.6 Hz, 1H), 3.98 (m 4H), 2.20 (m, 6H), 1.67 (d, J=6.5 Hz, 2H).

Step B:

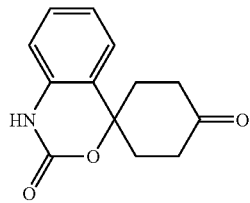

The product compound was prepared as a white solid from the de-protection of the acetal prepared in the previous step, using the procedure described in Step C of Example 1.

¹H NMR (400 MHz, CDCl₃) δ 9.51 (s, br, 1H), 7.25 (dt, J=7.0, 3.2 Hz, 1H), 7.20 (d, J=6.5 Hz, 1H), 7.05 (dt, J=7.0, 3.0 Hz, 1H), 6.90 (d, J=6.6 Hz, 1H), 3.05 (m, 2H), 2.55 (m, 2H), 2.30 (m, 2H), 2.21 (m, 2H).

Step C:

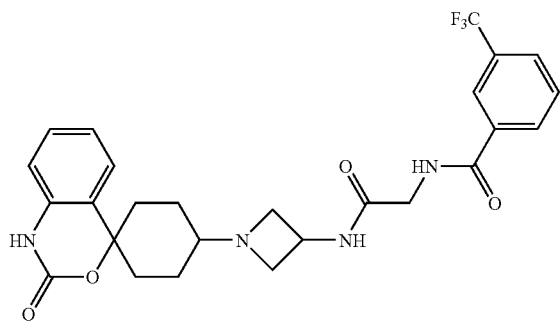

The product compounds were prepared as white solids from the reductive amination of the ketone in Step B and N-(azetidin-3-ylcarbamoylmethyl)-3-trifluoromethyl-benzamide (as prepared in Example 2 Step C) using the procedure described in Step D of Example 1.

40a: Less Polar Fraction from Silica Gel Column,

¹H NMR (400 MHz, CDCl₃) δ 8.95 (s, br, 1H), 8.18 (d, J=6.0 Hz, 1H), 8.10 (s, 1H), 8.02 (d, J=6.5 Hz, 1H), 7.85 (m, 1H), 7.65 (d, J=6.5 Hz, 1H), 7.55 (t, J=6.7 Hz, 1H), 7.40 (d, J=6.0 Hz, 1H), 7.20 (t, J=6.4 Hz, 1H), 7.05 (t, J=6.0 Hz, 1H), 6.80 (d, J=6.0 Hz, 1H), 4.55 (m, 1H), 4.20 (d, J=4.2 Hz, 2H), 3.89 (t, J=6.0 Hz, 2H), 3.75 (m, 2H), 3.65 (m, 1H), 2.95 (m, 1H), 2.30 (m, 1H), 2.30-2.15 (m, 2H), 2.14 (m, 2H), 1.95 (m, 2H), 1.65 (m, 2H).

40b: More Polar Fraction from Silica Gel Column

¹H NMR (400 MHz, CDCl₃) δ 8.90 (s, br, 1H), 8.20 (s, 1H), 8.11 (d, J=6.5 Hz, 1H), 8.02 (d, J=6.5 Hz, 1H), 7.78 (d, J=6.5 Hz, 1H), 7.70 (m, 1H), 7.60 (t, J=6.7 Hz, 1H), 7.25 (d, J=6.0 Hz, 1H), 7.10 (t, J=6.4 Hz, 2H), 6.85 (d, J=6.0 Hz, 1H), 4.70 (m, 1H), 4.20 (d, J=4.2 Hz, 2H), 3.80 (t, J=4.5 Hz, 2H), 3.69 (m, 2H), 2.65 (m, 1H), 2.30 (m, 2H), 1.85 (m, 6H).

Example 41

N-[(1-3'H-Spiro[cyclohex-1,1'-isobenzofuran]-4-yl-azetidin-3-ylcarbamoyl)-methyl]-3-trifluoromethyl-benzamide Step A: [2-(1,4-Dioxa-spiro[4.5]dec-7-en-8-yl)-phenyl]-methanol

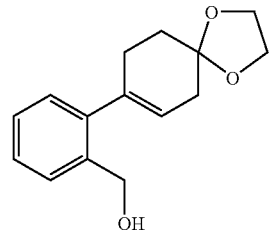

The title compound was prepared as a white solid from (2-iodo-phenyl)-methanol (Aldrich) using the procedure described in Step A of Example 38.

ESI-MS (m/z): Calcd. For C₁₅H₁₈O₃:246.13; found: 247.0 (M+H).

Step B: 3'H-Spiro[cyclohexane-1,1'-isobenzofuran]-4-one

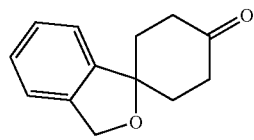

To a solution of [2-(1,4-dioxa-spiro[4.5]dec-7-en-8-yl)-phenyl]-methanol (1 g, 4.06 mmol, as prepared in the previous step) in DCM (2 mL) was added TFA (8 mL) and stirred at RT, 2 hours followed by removal of solvent in vacuo to afford the title compound.

ESI-MS (m/z): Calcd. For C₁₃H₁₄O₂: 202.02; found: 202.2 (M+H).

Step C: N-[(1-3'H-Spiro[cyclohex-1,1'-isobenzofuran]-4-yl-azetidin-3-ylcarbamoyl)-methyl]-3-trifluoromethyl-benzamide

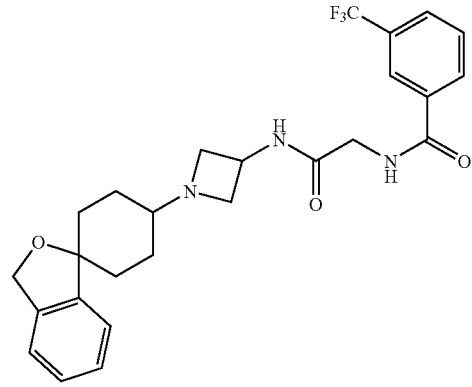

The title compounds were prepared as white solids from the reductive amination of the ketone in Step B and N-(azetidin-3-ylcarbamoylmethyl)-3-trifluoromethyl-benzamide (as prepared in Example 2 Step C) using the procedure described in Step D of Example 1.

41a: Less Polar Isomer from Silica Gel Column,
$^1$H NMR (CHLOROFORM-d) δ: 8.08-8.19 (m, 1H), 7.97-8.07 (m, 1H), 7.79 (d, J=7.6 Hz, 1H), 7.55-7.66 (m, 1H), 7.26-7.38 (m, 3H), 7.15-7.22 (m, 1H), 5.04 (s, 2H), 4.51-4.66 (m, 1H), 4.15-4.20 (m, 2H), 3.59-3.73 (m, 2H), 2.44 (br s, 2H), 1.90-2.03 (m, 1H), 1.82 (t, J=10.1 Hz, 2H), 1.51-1.64 (m, 4H), 1.43 (s, 2H).

41b: More Polar Isomer from Silica Gel Column
$^1$H NMR (CHLOROFORM-d) δ: 8.14 (br. s., 1H), 7.96-8.08 (m, 1H), 7.77 (d, J=7.8 Hz, 1H), 7.63-7.74 (m, 1H), 7.48-7.60 (m, 1H), 7.25 (d, J=4.8 Hz, 1H), 7.15-7.22 (m, 2H), 5.02 (d, J=8.3 Hz, 2H), 4.48-4.60 (m, 1H), 4.17 (d, J=5.3 Hz, 2H), 3.57-3.74 (m, 2H), 2.83-3.02 (m, 2H), 1.89-2.04 (m, 1H), 1.82 (d, J=11.9 Hz, 2H), 1.70 (d, J=9.3 Hz, 2H), 1.49-1.62 (m, 2H), 1.41 (d, J=8.8 Hz, 2H).

Example 42

In Vitro Biological Data

Compounds of the invention were subjected to various representative biological tests. The results of these tests are intended to illustrate the invention in a non-limiting fashion.

MCP-1 Receptor Binding Assay in THP-1 Cells

Human monocytic cell line THP-1 cells were obtained from American Type Culture Collection (Manassas, Va., USA). The THP-1 cells were grown in RPMI-1640 (RPMI: Roswell Park Memorial Institute Medium-cell culture growth media) supplemented with 10% fetal bovine serum in a humidified 5% $CO_2$ atmosphere at 37° C. The cell density was maintained between $0.5 \times 10^6$ cells/mL.

THP-1 (cells were incubated with 0.5 nM $^{125}$I labeled MCP-1 (Perkin-Elmer Life Sciences, Inc. Boston, Mass.) in the presence of varying concentrations of either unlabeled MCP-1 (R & D Systems, Minneapolis, Minn.) or test compound for 2 hours at 30° C. in a 96 well plate. Cells were then harvested onto a filter plate, dried, and 20 µL of Microscint 20 was added to each well. Plates were counted in a TopCount NXT, Microplate Scintillation & Luminescence Counter (Perkin-Elmer Life Sciences, Inc. Boston, Mass.). Blank values (buffer only) were subtracted from all values and drug treated values were compared to vehicle treated values. 1 µM cold MCP-1 was used for nonspecific binding.

Table 1 lists $IC_{50}$ values for inhibition of MCP-1 binding to CCR2 obtained for test compounds of the invention. Where an $IC_{50}$ value was not obtained for a particular compound, the percent inhibition is provided at a test concentration of 25 µM.

TABLE 1

Inhibition of MCP-1 Binding $IC_{50}$ (µM)
Table 1

| Example | CCR2 Binding (nM) |
| --- | --- |
| 1a | 130 |
| 2a | 230 |
| 3 | 2,200 |
| 4 | 5,900 |
| 5a | 24,000 |
| 6a | 380 |
| 7a | 2,700 |
| 8a | 430 |
| 9 | 1,600 |
| 10 | 1,000 |
| 11 | 280 |
| 12a | 820 |
| 13a | 100 |
| 14 | 280 |
| 15a | 5,400 |
| 16 | 7,100 |
| 17a | 2,860 |
| 18a | 330 |
| 19 | 66 |
| 20 | 110 |
| 21a | 6,500 |
| 22a | 1,100 |
| 23 | 410 |
| 24a | 680 |
| 25a | 340 |
| 26a | 95 |
| 27a | 170 |
| 28 | 110 |
| 29a | 21 |
| 30a | 88 |
| 31a | 340 |
| 32a | 510 |
| 33 | 410 |
| 34a | 290 |
| 35 | 430 |
| 36 | 1,500 |
| 37 | 9,000 |
| 38a | 920 |
| 39a | 1,500 |
| 40a | 2,200 |
| 41a | 80 |

Example 43

Animals

Mouse CCR2 knock-out/human CCR2 knock-in mice were generated using targeted 129Sv/Evbrd embryonic stem cell clones injected into C57BL/6 mice. Expression of the hCCR2 transcript was confirmed by quantitative reverse transcription-polymerase chain reaction performed on spleen and blood total RNA from homozygous hCCR2 knock-in mice. Backcrossing into C57BL/6 genetic background continued to the eighth generation. Transgenic mice were houses in a specific-pathogen-free, temperature-controlled facility that maintained a 12-hour light/12-hour dark cycle. Mice had free access to water and food. Experimental procedures were carried out in accordance with institutional standards for animal care and were approved by the institute's animal care and use committee.

Example 44

Murine In Vivo Cell Migration Assay

Animals are orally dosed with vehicle or CCR2 antagonists at 3, 10 and 30 mg/kg bid. Animals undergo anesthesia and laparotomy. A distal loop of small bowel (5 cm in length) is gently eventrated onto moist sterile gauze. Synthetic human MCP-1 (1 mg/100 ml sterile PBS) or PBS alone is administered drop-wise onto the serosa of the eventrated loop. A suture knot is placed into the mesentery to mark the terminus of the treated area. Twenty-four hours later, the animal is sacrificed and the segment of bowel plus the adjacent region is removed. The tissue is opened along the mesenteric border, pinned flat and the mucosa removed. The remaining muscle layer is fixed briefly in 100% EtOH and then stained using Hanker-Yates reagent to detect myeloperoxidase-containing immune cells. At 10 mpk, P.O. bid, a compound is deemed efficacious if the inhibition of cell migration reaches 30% compared with vehicle-treated animals.

Example 45

Thiolycollate-Induced Peritonitis in Mice

Animals are orally dosed with vehicle or CCR2 antagonists at 3, 10, 30 and 100 mg/kg bid). One hour later, the animals are intraperitoneally injected with sterile thioglycollate (25 mL/kg, ip, Sigma) for induction of peritonitis. Animals are orally treated twice daily with vehicle or CCR2 antagonists. At the 72-hour time point, perinoteal cavities are lavaged with 10 mL of sterile saline. Total cell counts in the peritoneal lavage fluid are performed using a microscope and cell differentiation is performed using cytospin analysis after Giemsa staining (Hema Tek 2000). Percent inhibition of the thioglycollate-induced peritonitis is calculated by comparing the change in number of leukocytes of CCR2 antagonist treated mice to the vehicle-treated mice.

Example 46

MCP-1-Induced Monocyte Recruitment to Airway of Mice

Animals are orally treated with vehicle or CCR2 antagonists at 3, 10, and 30 mg/kg po bid). One hour later, the animals are intranasally dosed with 4 μg of MCP-1 in sterile saline. The animals are orally treated twice daily with vehicle or CCR2 antagonists. After 48 h, mice are euthanized by intraperitoneal injection of anesthesia solution (Sleepaway-Sodium pentobarbital). Whole bronchioalveolar lavage (BAL) is performed using 1.4 ml of ice-cold PBS containing 3 mM EDTA. Total cell counts in the BAL lavage fluid are performed using a microscope and cell differentiation is performed using cytospin analysis after Giemsa staining (Hema Tek 2000). Percent inhibition is calculated by comparing the change in number of total leukocyte counts (including monocytes/macrophages and lymphocytes) of compound-treated mice to the vehicle-treated mice. Compounds are deemed efficacious if percent inhibition reaches 30%.

Example 47

High-Fat Diet Induced Obesity and Insulin Resistance in Mice

Obesity is induced by a high-fat diet that derived approximately 60% calories from lipids (D-12492; Research Diets Inc.) in animals for 10-24 weeks at age of 7 weeks. Prior to age 7 weeks, animals are fed a standard pellet diet, in which 5% of calories were provided as fat. Obese animals were randomized by body weight and fat mass. The obese animals are orally treated with vehicle or CCR2 antagonists at 3, 10 and 30 mg/kg, po bid. Body weight and food intake and were fasting blood glucose levels monitored. Body mass was determined by a NMR analyzer (Burker MiniSpec). Insulin tolerance test is carried out in animals that were fasted for 3 hours. After an intraperitoneal bolus injection of recombinant human insulin (1.5 U/kg), blood glucose concentrations are measured using a Glucometer before and 15, 30, 45, 60, 90 and 120 minutes after injection. Glucose tolerance tests are performed after an overnight (17-hour) fast. Blood glucose concentrations are measured before and after 15, 30, 60, 90, 120 minutes after an oral dose of glucose dissolved in water (1 g/kg). Energy expenditure analysis was monitored by a complete laboratory animal monitor system. After 40 days treatment with vehicle or CCR2 antagonists, the animals are sacrificed by $CO_2$ asphyxiation. Percent of weight loss is calculated by comparing the body weight changes of the compound-treated mice with the vehicle-treated mice.

Example 48

Mouse Model of Allergic Asthma

Animals are sensitized by intraperitoneal injection of 10 μg chicken egg albumin (OVA) absorbed to 1 mg Imject® in 100 μL phosphate-buffered saline (PBS) on days 0 and 5. Control animals received PBS ip. OVA-immunized animals were challenged by inhalation of 0.5% OVA aerosol for 10 minutes by an ultrasonic nebulizer on days 12, 16 and 20. Control animals were challenged with PBS in similar fashion. The OVA-sensitized animals receive vehicle (0.5% Methocel) or CCR2 antagonists orally at 3, 10, 30 mg/kg twice daily from days 9-20 and once daily on Day 21, 2 hours before sacrifice. Dexamethason (5 mg/kg) and Montelukast (1 mg/kg) are given orally once a day. On day 21, 2 hours post the last dose of CCR2 compounds, bronchial reactivity to aerosolized methacholine is measured using a Buxco whole body plethysmograph. On day 21, the animals are sacrificed. Bronchoalveolar lavage fluid is collected (1 mL) and total cells counted. The numbers of eosinophils, lymphocytes, monocytes and neutrophils are determined using cytospin analysis after Giemsa staining (Hema Tek 2000). Percent inhibition of total BAL leukocyte count (and eosinophil count) is calculated by comparing the compound-treated mice with vehicle-treated mice. Compounds are deemed efficacious if the inhibition reaches 30%.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

We claim:
1. A compound of Formula (I)

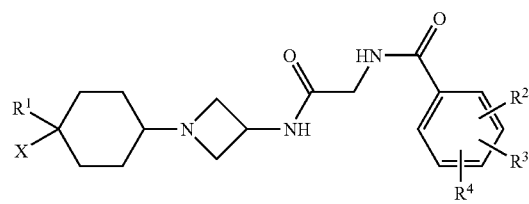

Formula (I)

X is H, F, OH, or $NH_2$;
$R^1$ is

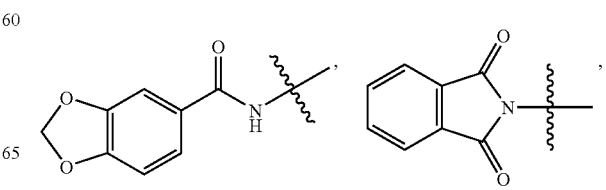

-continued

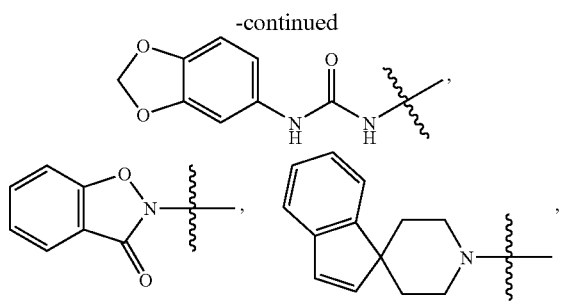

—O-benzoisothiazol-3-yl, —O-benzoisoxazolyl, —O-benzothiazolyl, —O-benzoxazolyl, —O-benzofuryl, —O-indolyl, —O-benzoimidazolyl, —O-indazolyl, —O-furyl, —O-imidazolyl, —O-oxazolyl, —O-isoxazolyl, —O-thiophenyl, —O-benzothiophenyl, —O-thiazolyl, —O-isothiazolyl, —O-pyridazyl, —O-pyrazolyl, —O-pyrrolyl, —O— benzo[1,3]dioxolyl, —O-pyrimidyl, indazol-1-yl, —O-pyridyl, imidazol-1-yl, pyridon-1-yl, pyrimidon-1-yl, pyrazol-1-yl, indol-1-yl, pyridaz-1-yl, or pyrrol-1-yl;

alternatively, both $R^1$ and X can be taken together with their attached carbon to form a ring selected from the group consisting of:

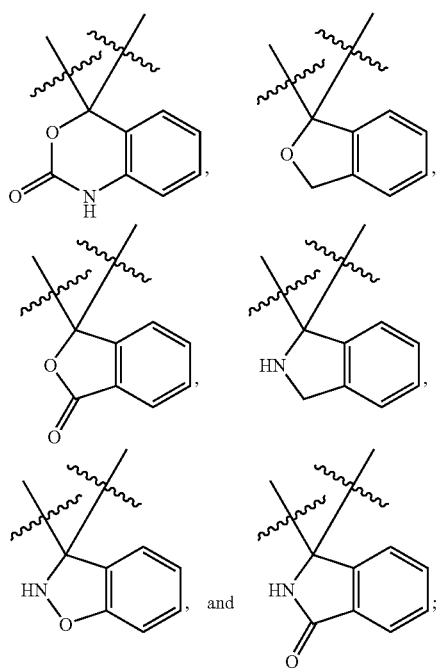

wherein any $R^1$ group may be substituted with up to two methyl groups, or one substituent selected from the group consisting of: $OC_{(1-4)}$alkyl, $OC_{(3-6)}$cycloalkyl, $OCH_2CF_3$, $OCH_2Ph$, F, I, CN, Cl, $OCF_3$, $CF_3$, $CH_2CN$, $C_{(1-4)}$alkyl, $CH_2CF_3$, $N(C_{(1-4)}alkyl)_2$, $C_{(1-4)}$alkylOH, $Si(CH_3)_3$,

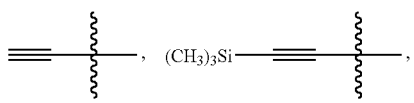

$SCH_3$, $S(O)CH_3$, $SO_2CH_3$, pyrrolidinyl, OH, $NH_2$, NHCN, $CO_2H$, $CONH_2$, $NHCO_2C_{(1-4)}$alkyl, $N(SO_2CH_3)_2$, $NHSO_2CH_3$, $NHC(O)CF_3$, $NHC_{(1-4)}$alkyl, $NHCO_2H$, $NHCO_2C_{(1-4)}$alkyl, $NHCOC_{(1-4)}$alkyl, $NHCONH_2$, $NHCONHC_{(1-4)}$alkyl, and Br;

$R^2$ is $C_{(1-4)}$alkyl, $NH_2$, $NO_2$, $NHCH_2CH_2OH$, $N(C_{(1-4)}alkyl)_2$, $N(SO_2CH_3)_2$, CN, F, Cl, Br, $CF_3$, cycloalkyl, heterocyclyl, $OCF_3$, $OCF_2H$, $CF_2H$, or $OC_{(1-4)}$alkyl;

$R^3$ is H, F, Cl, $CF_3$, or $OC_{(1-4)}$alkyl; alternatively, $R^2$ and $R^3$ may be taken together with their attached phenyl to form a benzo[1,3]dioxolyl, 2,3-dihydro-benzofuranyl, or 2,3-dihydro-benzo[1,4]dioxinyl group;

$R^4$ is H, $OC_{(1-4)}$alkyl, or F;

and tautomers, and pharmaceutically acceptable salts thereof.

2. A compound of claim 1 wherein:

X is H, F, or OH;

$R^1$ is

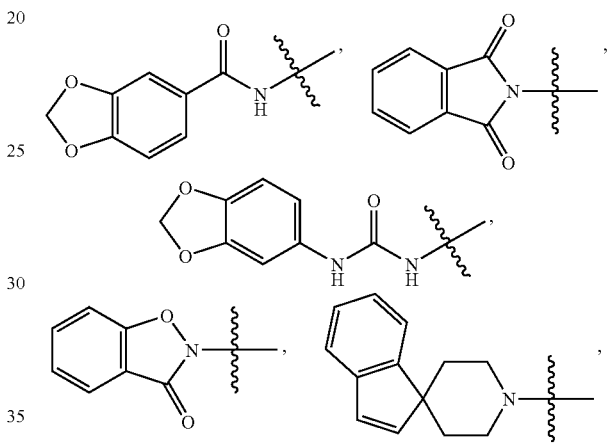

—-O-benzoisothiazol-3-yl, —O-benzoisoxazolyl, —O-benzothiazolyl, —O-benzoxazolyl, —O-benzofuryl, —O-indolyl, —O-benzoimidazolyl, —O-indazolyl, —O-furyl, —O-imidazolyl, —O-oxazolyl, —O-isoxazolyl, —O-thiophenyl, —O-benzothiophenyl, —O-thiazolyl, —O-isothiazolyl, —O-pyridazyl, —O-pyrazolyl, —O-pyrrolyl, —O— benzo[1,3]dioxolyl, —O-pyrimidyl, indazol-1-yl, —O-pyridyl, imidazol-1-yl, pyridon-1-yl, pyrimidon-1-yl, pyrazol-1-yl, indol-1-yl, pyridaz-1-yl, or pyrrol-1-yl;

wherein said —O-pyridyl is optionally substituted with Br, F, Cl, OH, CN, $OCF_3$, $CF_3$, $OC_{(1-4)}$alkyl, or $C_{(1-4)}$alkyl; wherein said imidazol-1-yl is optionally substituted with up to two $CH_3$ groups; wherein said pyridon-1-yl or said —O-pyrimidyl is optionally substituted with Cl, OH, CN, $OCF_3$, $CF_3$, $C_{(1-4)}$alkyl, F, I or $OC_{(1-4)}$alkyl; wherein said pyrimidon-1-yl is optionally substituted with Br, F, I, Cl, OH, CN, $OCF_3$, $CF_3$, $OC_{(1-4)}$alkyl, or $C_{(1-4)}$alkyl; and wherein said pyrazol-1-yl is optionally substituted with F, I,

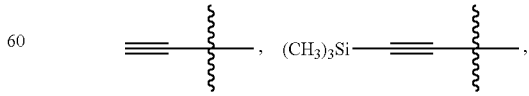

or $C_{(1-4)}$alkyl;

alternatively, both $R^1$ and X can be taken together with their attached carbon to form a ring selected from the group consisting of:

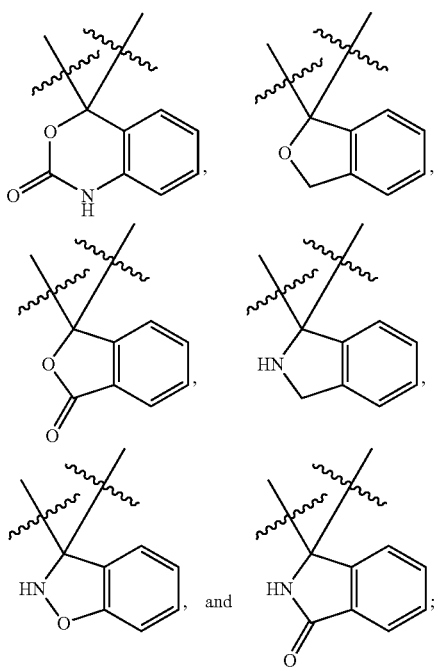

R² is $C_{(1-4)}$alkyl, NH₂, NO₂, NHCH₂CH₂OH, N($C_{(1-4)}$alkyl)₂, N(SO₂CH₃)₂, CN, F, Cl, Br, CF₃, pyrrolidinyl, OCF₃, OCF₂H, CF₂H, or O$C_{(1-4)}$alkyl;

R³ is H, F, Cl, CF₃, or O$C_{(1-4)}$alkyl; alternatively, R² and R³ may be taken together with their attached phenyl to form a benzo[1,3]dioxolyl group;

R⁴ is H, OCH₃, or F;

and tautomers, and pharmaceutically acceptable salts thereof.

3. A compound of claim 2 wherein:

X is H, or F;

R¹ is

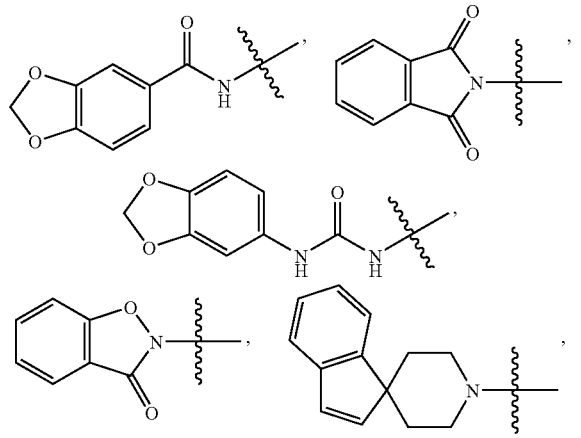

—O-benzoisothiazol-3-yl, —O-benzoisoxazolyl, —O—benzo[1,3]dioxolyl, —O-pyrimidyl, indazol-1-yl, —O-pyridyl, imidazol-1-yl, pyridon-1-yl, pyrimidon-1-yl, or pyrazol-1-yl, wherein said —O-pyridyl is optionally substituted with Br, F, I, Cl, OH, CN, OCF₃, CF₃, O$C_{(1-4)}$alkyl, or $C_{(1-4)}$alkyl; wherein said imidazol-1-yl is optionally substituted with up to two CH₃ groups; wherein said pyridon-1-yl is optionally substituted with Cl, OH, CN, OCF₃, CF₃, $C_{(1-4)}$alkyl, F, or O$C_{(1-4)}$alkyl; wherein said pyrimidon-1-yl or said —O-pyrimidyl is optionally substituted with Br, F, Cl, OH, CN, OCF₃, CF₃, O$C_{(1-4)}$alkyl, or $C_{(1-4)}$alkyl; and wherein said pyrazol-1-yl is optionally substituted with F,

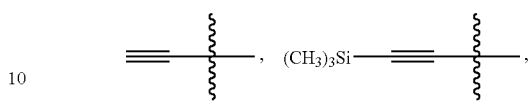

or $C_{(1-4)}$alkyl;

alternatively, both R¹ and X can be taken together with their attached carbon to form a ring selected from the group consisting of:

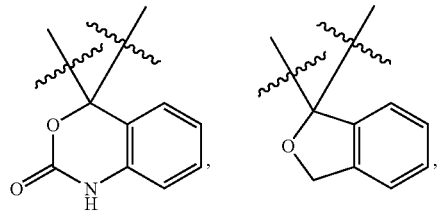

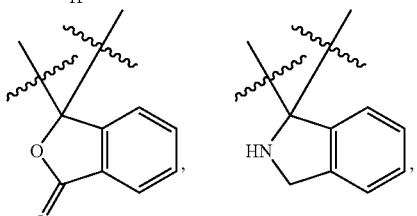

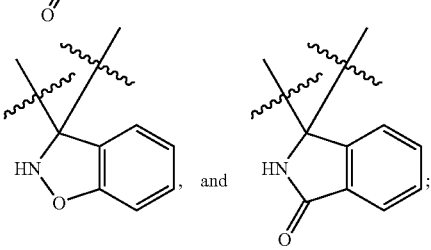

R² is NH₂, NO₂, NHCH₂CH₂OH, N(CH₃)₂, N(SO₂CH₃)₂, CN, F, Cl, Br, CF₃, pyridinyl, pyrrolidinyl, or OCH₃;

R³ is H, F, Cl, CF₃, or OCH₃; alternatively, R² and R³ may be taken together with their attached phenyl to form a benzo[1,3]dioxolyl group;

R⁴ is H, or F;

and tautomers, and pharmaceutically acceptable salts thereof.

4. A compound of claim 3 wherein:

X is H;

R¹ is

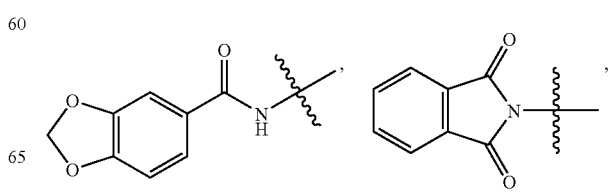

-continued

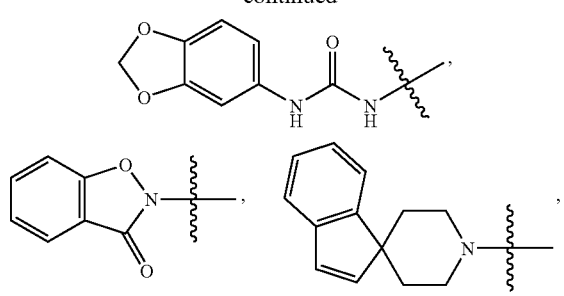

—O-benzoisothiazol-3-yl, —O-benzoisoxazolyl, —O—benzo[1,3]dioxolyl, —O-pyrimidyl, indazol-1-yl, —O-pyridyl, imidazol-1-yl, pyridon-1-yl, pyrimidon-1-yl, or pyrazol-1-yl, wherein said —O-pyridyl is optionally substituted with $OC_{(1-4)}$alkyl, or $C_{(1-4)}$alkyl; wherein said imidazol-1-yl is optionally substituted with up to two $CH_3$ groups; wherein said pyridon-1-yl is optionally substituted with Cl, OH, CN, $CF_3$, $C_{(1-4)}$alkyl, F, or $OC_{(1-4)}$alkyl; wherein said pyrimidon-1-yl or said —O-pyrimidyl is optionally substituted with Br; and wherein said pyrazol-1-yl is optionally substituted with F,

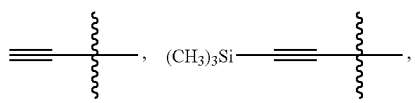

or $C_{(1-4)}$alkyl;

alternatively, both $R^1$ and X can be taken together with their attached carbon to form a ring selected from the group consisting of:

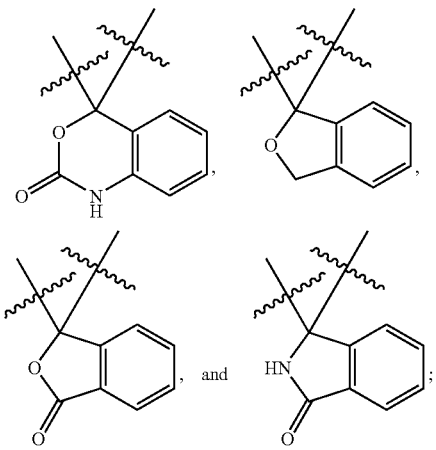

$R^2$ is F, Br, $CF_3$, $NO_2$, $NH_2$, $NHCH_2CH_2OH$, $N(CH_3)_2$, $N(SO_2CH_3)_2$, pyrrolidinyl, pyridinyl, $OCH_3$;

$R^3$ is H;

$R^4$ is H;

and tautomers, and pharmaceutically acceptable salts thereof.

5. A compound of claim 4 wherein:

$R^1$ is

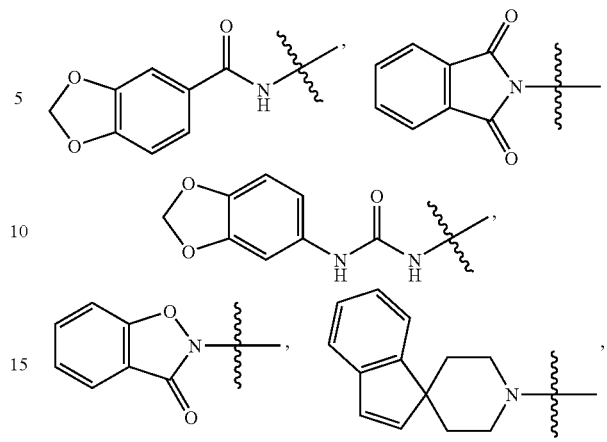

—O-benzoisothiazol-3-yl, —O-benzoisoxazolyl, —O—benzo[1,3]dioxolyl, —O-pyrimidyl, indazol-1-yl, —O-pyridyl, imidazol-1-yl, pyridon-1-yl, pyrimidon-1-yl, or pyrazol-1-yl, wherein said —O-pyridyl is optionally substituted with $OCH_3$, or $CH_3$;

wherein said imidazol-1-yl is optionally substituted with up to two $CH_3$ groups; wherein said pyridon-1-yl is optionally substituted with Cl, OH, CN, $CF_3$, $CH_3$, F, or $OCH_3$;

wherein said pyrimidon-1-yl or said —O-pyrimidyl is optionally substituted with Br; and wherein said pyrazol-1-yl is optionally substituted with F,

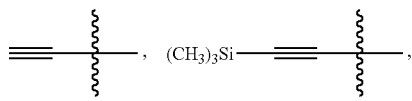

or $CH_3$;

alternatively, both $R^1$ and X can be taken together with their attached carbon to form a ring selected from the group consisting of:

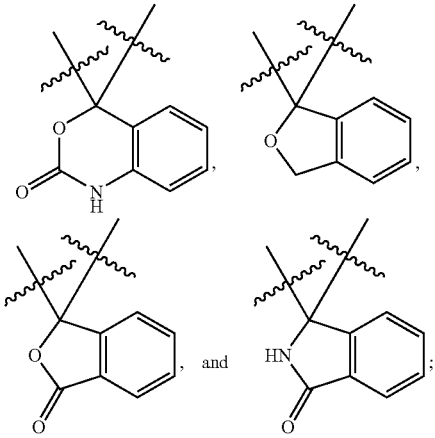

$R^2$ is $CF_3$;

and tautomers, and pharmaceutically acceptable salts thereof.

6. A compound selected from the group consisting of:
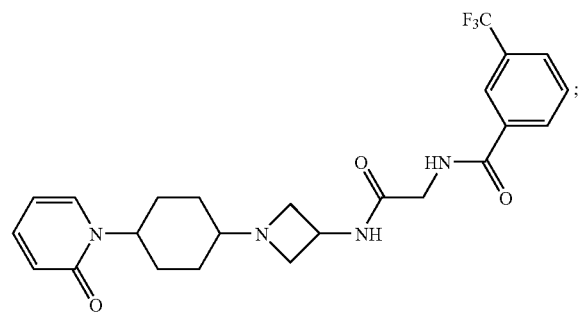
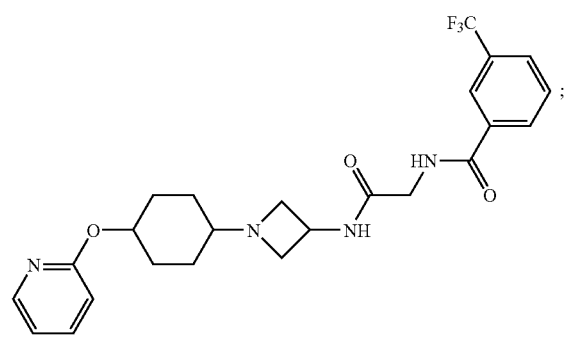
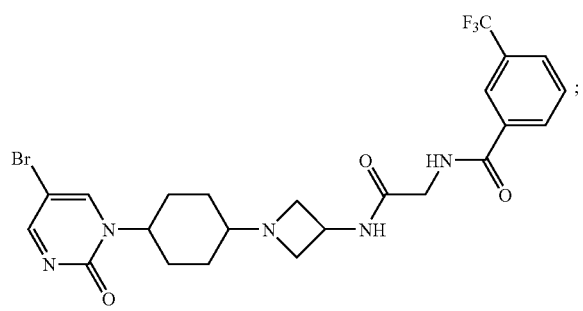
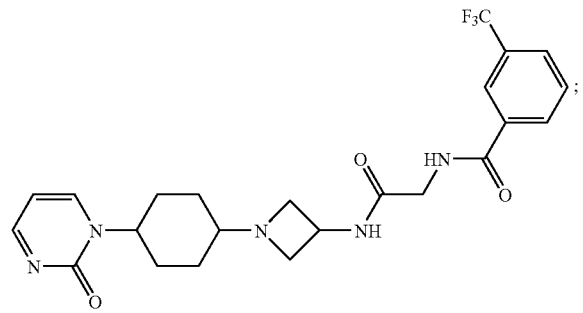
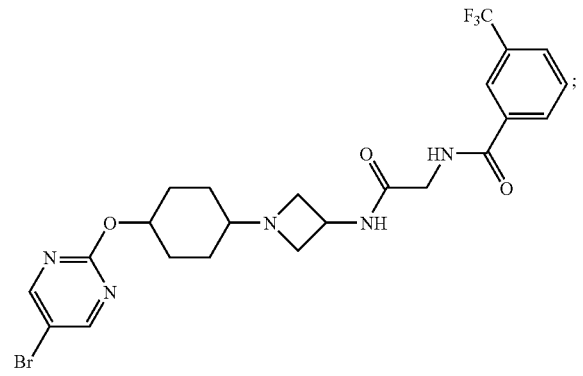
-continued
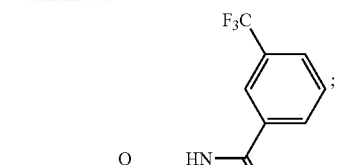
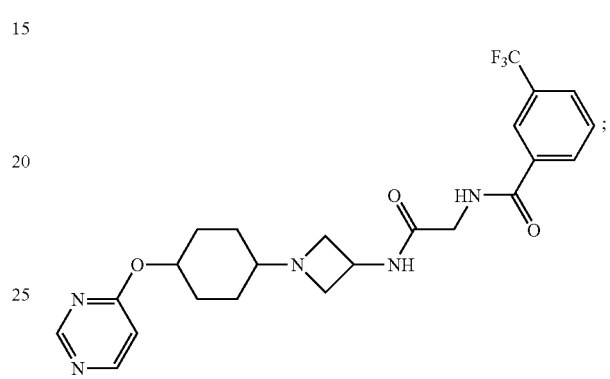
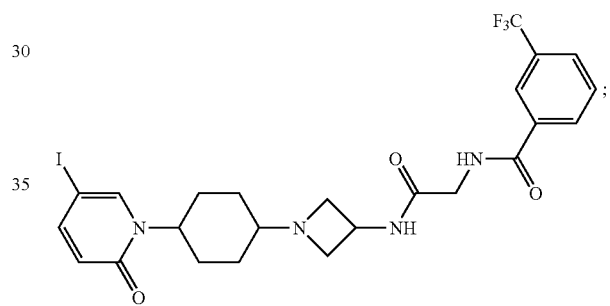
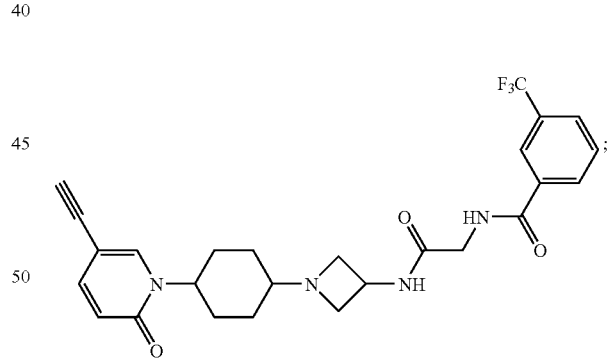
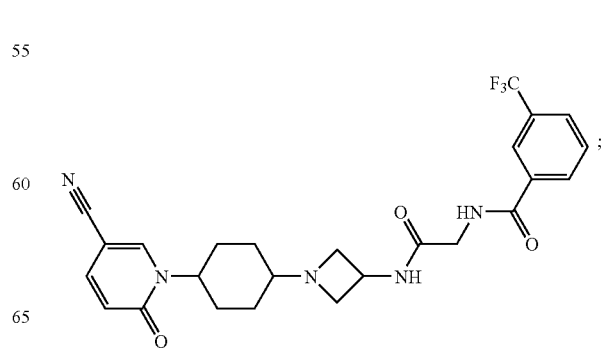

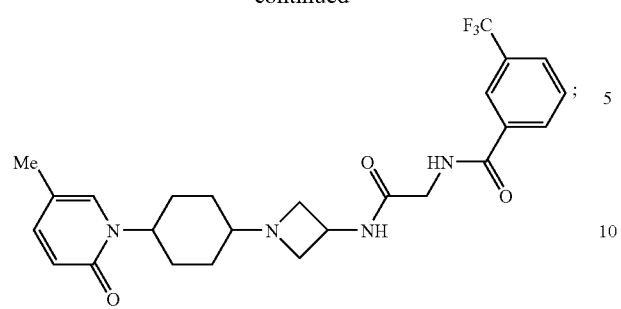
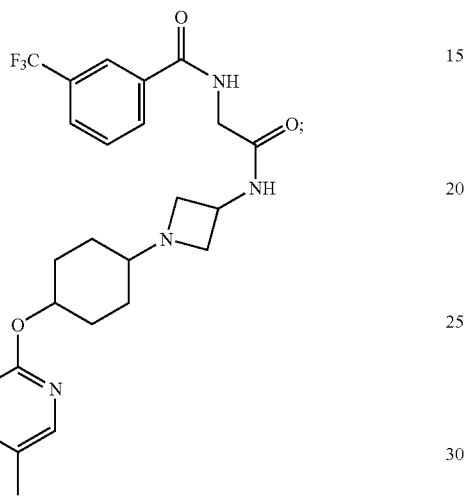
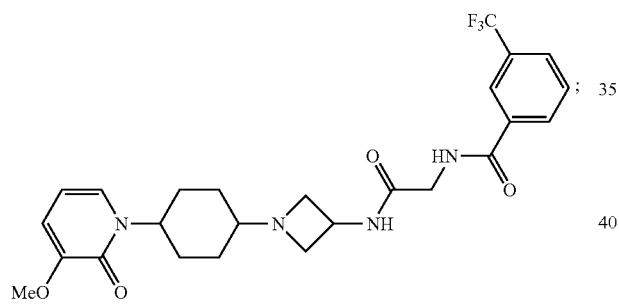
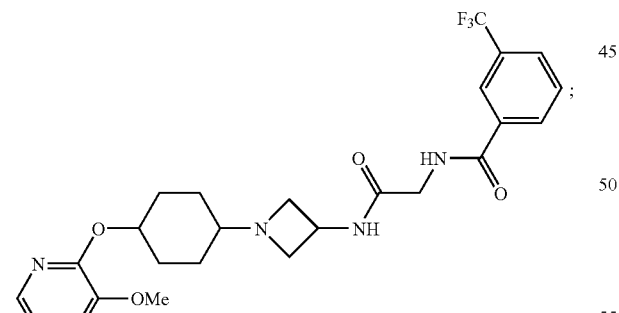
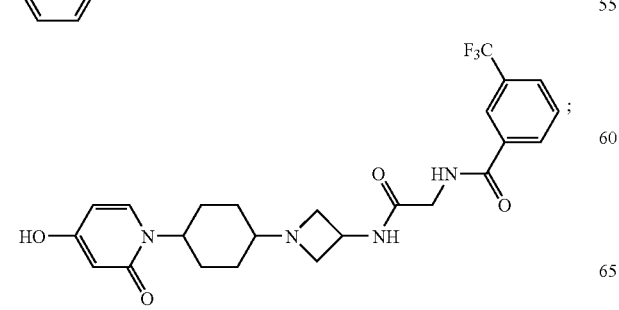
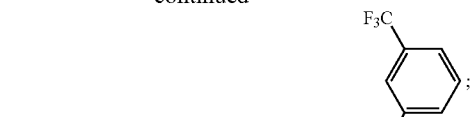
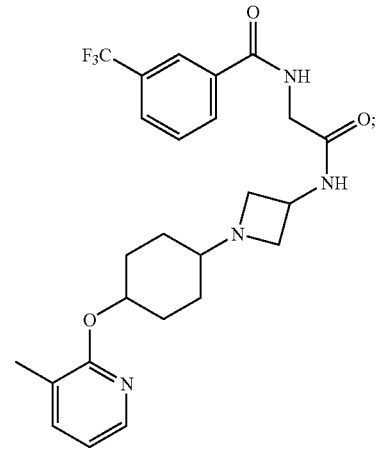
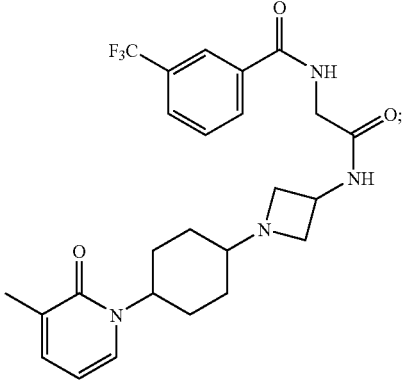
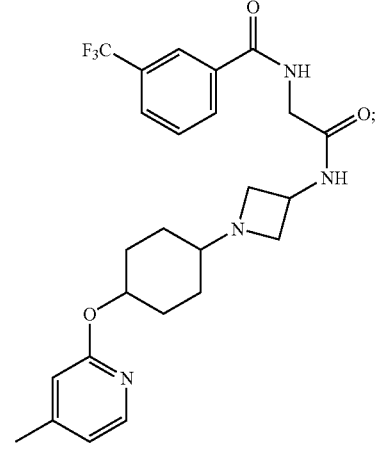

111
-continued
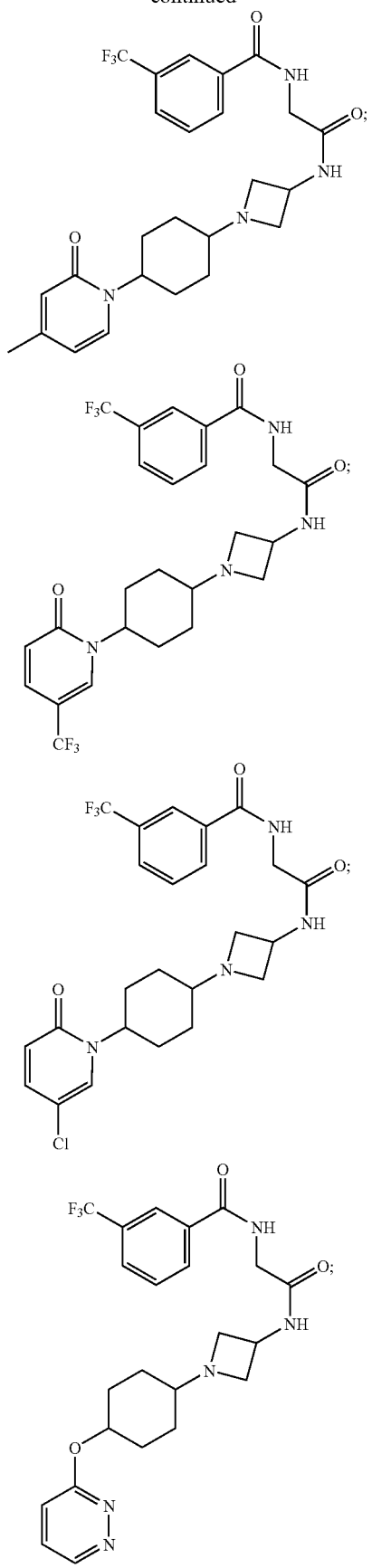
112
-continued
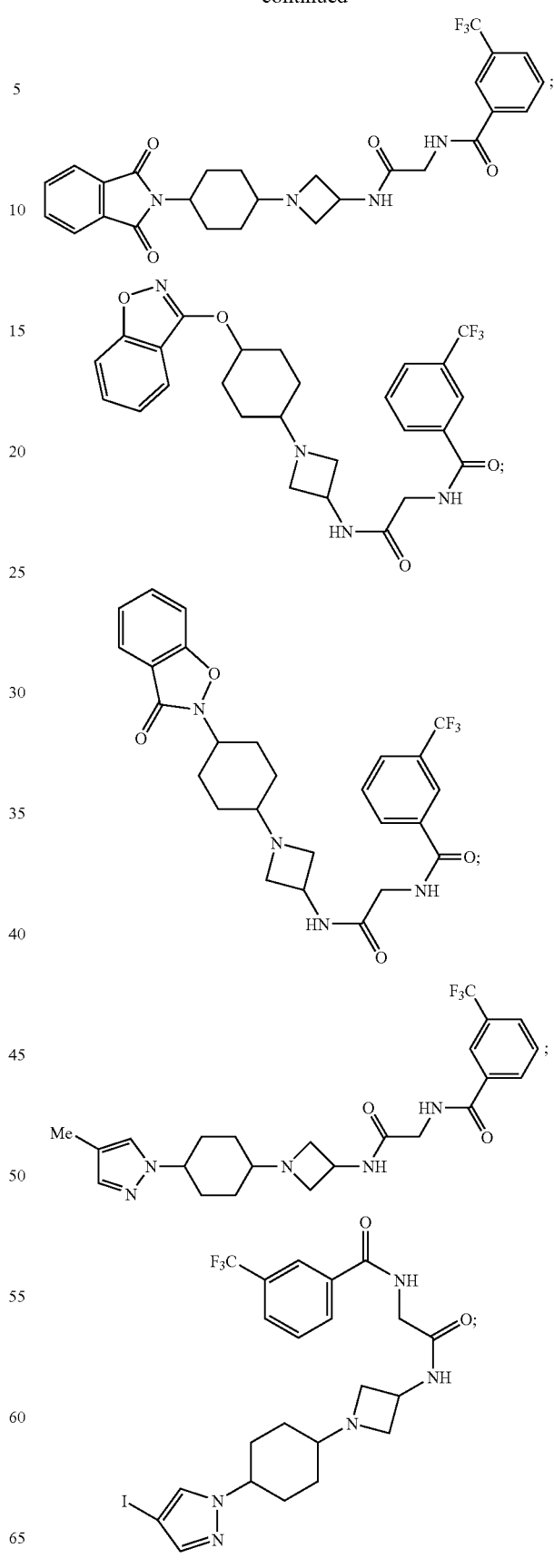

113
-continued
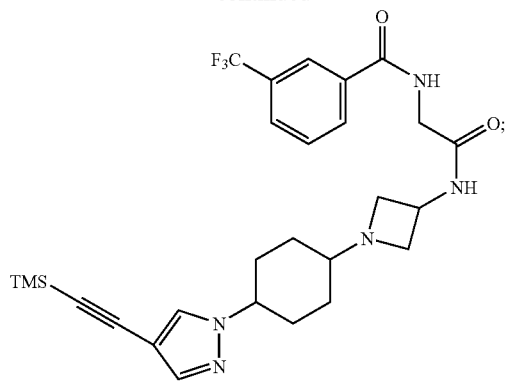
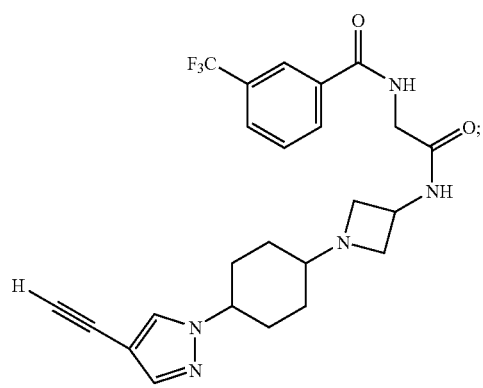
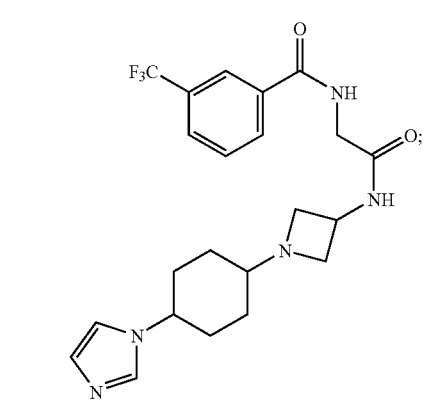
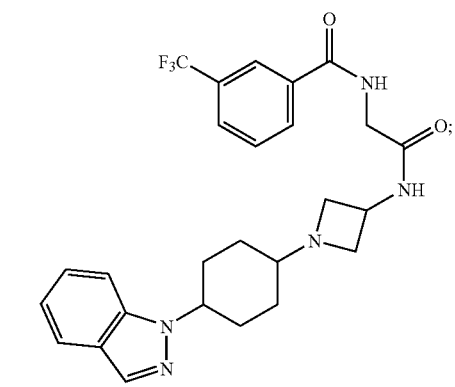
114
-continued
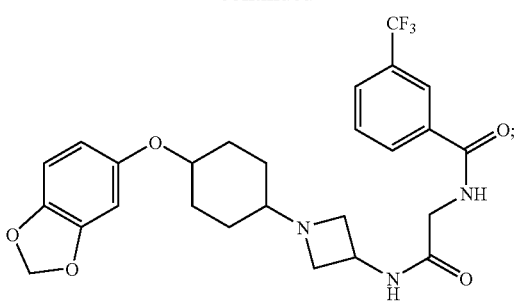
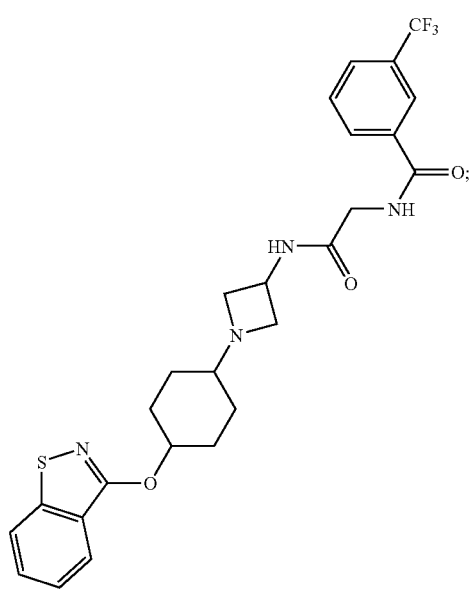
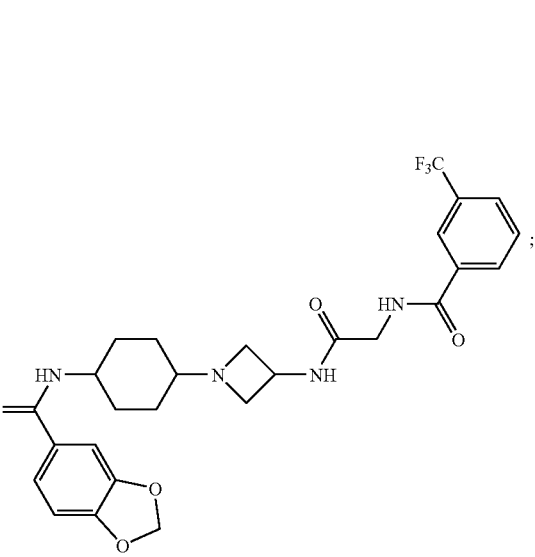

-continued
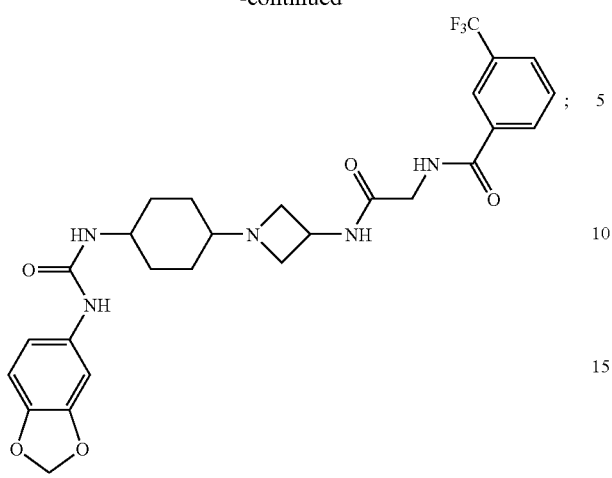
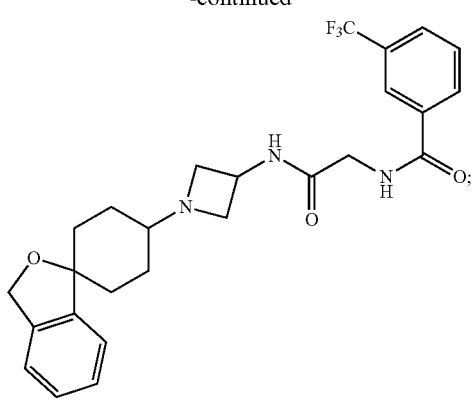
or tautomers, prodrugs, and pharmaceutically acceptable salts thereof.
7. A compound of claim 6 selected from the group consisting of:
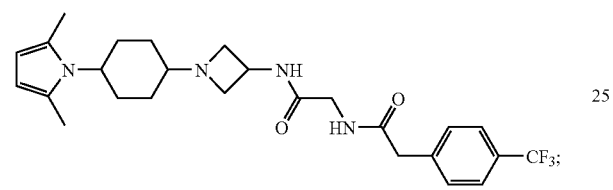
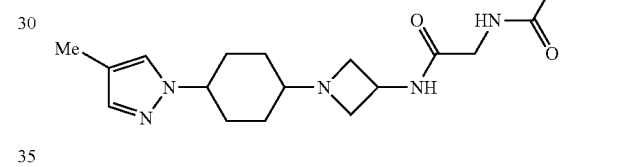
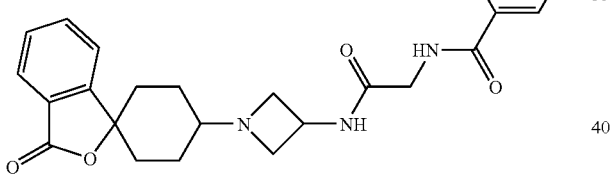
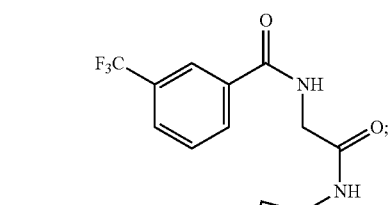
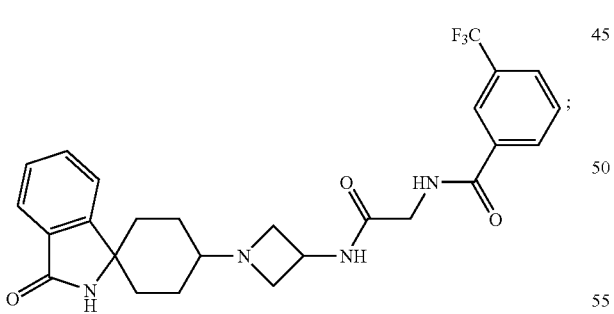
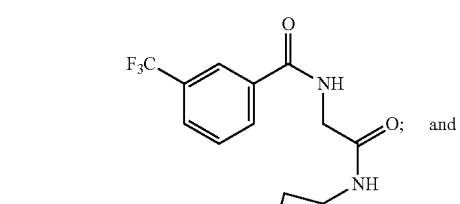
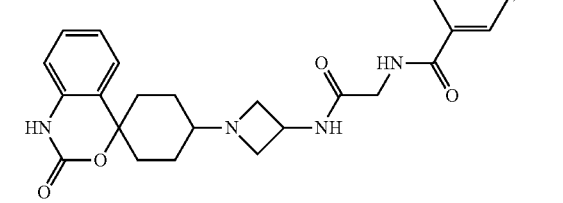
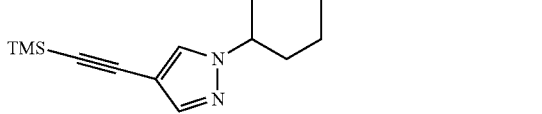

-continued

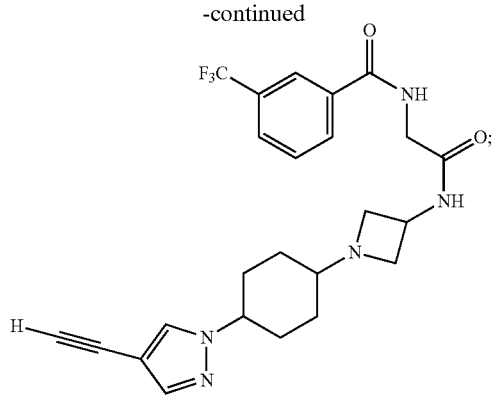

or tautomers, prodrugs, and pharmaceutically acceptable salts thereof.

8. A compound of claim 7, which is

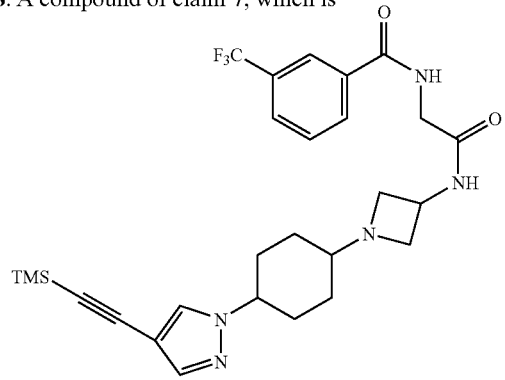

or tautomers, prodrugs, and pharmaceutically acceptable salts thereof.

9. A pharmaceutical composition, comprising a compound of claim 1 and a pharmaceutically acceptable carrier.

10. A pharmaceutical composition, comprising a compound of claim 1 and a pharmaceutically acceptable carrier, made by mixing a compound of claim 1 and a pharmaceutically acceptable carrier.

11. A process for making a pharmaceutical composition, comprising a compound of claim 1 and a pharmaceutically acceptable carrier, which comprises mixing a compound of claim 1 and a pharmaceutically acceptable carrier.

12. A process for the preparation of a compound of Formula (I) of claim 1, comprising reacting a compound of Formula (V)

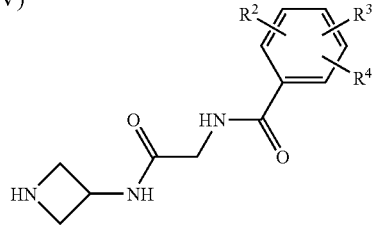

with a compound of Formula (VI)

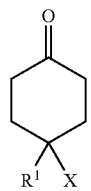

in the presence of a reducing agent to provide the compound of Formula (I).

13. A product of formula (I) made by the process of claim 12.

14. A process for the preparation of a compound of Formula (I) of claim 1, comprising reacting a compound of Formula (XIII)

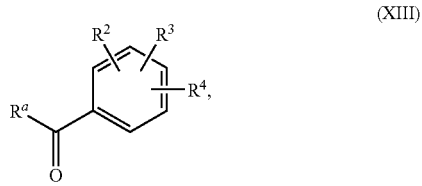

where $R_a$ is OH or Cl, with

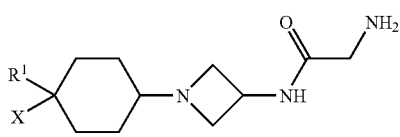

in the presence of HOBt/EDCI or $Et_3N$ to provide the compound of Formula (I).

15. A product of formula (I) made by the process of claim 14.

16. A method of treating a disorder selected from the group consisting of type II diabetes, obesity and asthma comprising administering to a subject in need thereof a therapeutically effective amount of a compound of claim 1.

* * * * *